US006846809B2

(12) United States Patent
Cristiano et al.

(10) Patent No.: US 6,846,809 B2
(45) Date of Patent: Jan. 25, 2005

(54) PEI: DNA VECTOR FORMULATIONS FOR IN VITRO AND IN VIVO GENE DELIVERY

(75) Inventors: Richard J. Cristiano, Pearland, TX (US); Motoyuki Yamashita, Kochi (JP)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/962,922

(22) Filed: Sep. 25, 2001

(65) Prior Publication Data

US 2002/0151060 A1 Oct. 17, 2002

Related U.S. Application Data

(60) Provisional application No. 60/235,237, filed on Sep. 25, 2000, and provisional application No. 60/235,635, filed on Sep. 26, 2000.

(51) Int. Cl.$^7$ .............................................. A61K 48/00
(52) U.S. Cl. ...................... 514/44; 435/320.1; 435/455; 424/482
(58) Field of Search ........................ 514/44; 435/320.1, 435/455, 91.1, 458; 424/482

(56) References Cited

U.S. PATENT DOCUMENTS

| | | | |
|---|---|---|---|
| 5,260,002 A | 11/1993 | Wang | 264/4.1 |
| 5,354,844 A | 10/1994 | Beug et al. | 530/345 |
| 5,462,866 A | 10/1995 | Wang | 435/174 |
| 5,494,682 A | 2/1996 | Cohen et al. | 424/489 |
| 5,641,656 A * | 6/1997 | Sekellick et al. | 435/69.51 |
| 5,656,611 A | 8/1997 | Kabanov et al. | 514/44 |
| 5,792,645 A | 8/1998 | Beug et al. | 435/240.2 |
| 5,824,654 A | 10/1998 | Lavie et al. | 514/44 |
| 5,871,982 A | 2/1999 | Wilson et al. | 435/172.3 |
| 5,908,777 A | 6/1999 | Lee et al. | 435/320.1 |
| 5,972,600 A | 10/1999 | Szoka, Jr. et al. | 435/6 |
| 6,071,533 A | 6/2000 | Papahadjopoulos et al. | 424/450 |
| 6,071,741 A | 6/2000 | Wong et al. | 435/320.1 |
| 6,083,741 A | 7/2000 | Hart et al. | 435/320.1 |
| 6,113,946 A | 9/2000 | Szoka, Jr. et al. | 424/486 |
| 6,313,285 B1 * | 11/2001 | Butler et al. | 536/25.4 |
| 6,506,890 B1 * | 1/2003 | Cooper et al. | 536/23.1 |
| 2001/0005717 A1 * | 6/2001 | Wagner | 514/44 |
| 2001/0006817 A1 * | 7/2001 | Pack | 435/440 |
| 2003/0026841 A1 * | 2/2003 | Trubetskoy et al. | 424/486 |

FOREIGN PATENT DOCUMENTS

WO    WO 96/11671    *    4/1996

OTHER PUBLICATIONS

Kircheis, Advanced Drug Delivery Reviews, 53, 341–358, 2001.*
Schatzlein, Anti–Cancer Drugs, 12, pp. 275–304, 2001.*
Mendiratta, Human Gene Therapy, 11:1851–1862, 2000.*
Horn, Human Gene Therapy, 6:565–573, 1995.*
Monteiro, Biotechnol Bioeng 66:189–194, 1999.*
Gomez–Navarro et al., Eropean J of Cancer, vol. 35, No. 6, pp. 867–885, 1999.*
Meng et al. (Gene Therapy of Cancer, Chapter I, pp. 3–20, 1999).*
Plenat (Molecular Medicine Today, vol. 1, 3, 1996, pp. 250–257).*
Anderson (Nature, vol. 292, 25–30, 1998).*
Verma et al. (Nature, vol. 389, pp. 239–242, 1997).*
Blessing et al., "Different strategies for formation of PEGylated EGF–conjugated PEI/DNA complexes for targeted gene delivery," *Bioconjugate Chem.*, 12:529–537, 2001.
Hart, "Synthetic vectors for gene therapy," *Expert Opinion on Therapeutic Patents*, 10(2):199–208, 2000.
Bendas et al., "Targetability of novel immunoliposomes prepared by a new antibody conjugation technique," *Int. J. Pharm.*, 181:79–93, 1999.
Boletta et al., "Nonviral gene delivery to the rat kidney with polyethylenimine," *Human Gene Therapy*, 8:1243–1251, 1997.
Bousiff et al., "A versatile vector for gene and oligonucleotide transfer into cells in culture and in vivo: Polyethylenimine," *Proc. Natl. Acad. Sci. USA*, 92:7297–7301, 1995.
Boussif et al., "Optimized galenics improve in vitro gene transfer with cationic molecules up to 1000–fold," *Gene Therapy*, 3:1074–1080, 1996.
Chen et al., "Enhancement of DNA vaccine potency by linkage of antigen gene to an HSP70 gene," *Cancer Research*, 60(4):1035–1042, 2000.
Coll et al., "In vivo delivery to tumors of DNA complexed with linear polyethylenimine," *Human Gene Therapy*, 10(10):1659–1666, 1999.
Cristiano and Roth, "Epidermal growth factor mediated DNA delivery into lung cancer cells via the epidermal growth factor receptor," *Cancer Gene Therapy*, 3:4–10, 1996.
Cristiano and Roth, "Molecular conjugates: a targeted gene delivery vector for molecular medicine," *J. Mol. Med.*, 73:479–486,1995.
Densmore et al., "Aerosol delivery of robust polyethylenimine–DNA complexes for gene therapy and genetic immunization," *Molecular Therapy*, 1:180–188, 2000.
Fraley et al., "Entrapment of a bacterial plasmid in phospholipid vesicles: potential for gene transfer," *Proc. Natl. Acad. Sci. USA*, 76:3348–3352, 1979.
Fronsdal et al., "Efficient DNA–mediated gene transfer into prostate cancer cell line LNCaP,"*Prostate*, 43(2):111–117, 2000.
Gao et al., "Direct in vivo gene transfer to airway epithelium employing adenovirus–polylysine–DNA complexes," *Human Gene Therapy*, 4:17–23, 1993.

(List continued on next page.)

*Primary Examiner*—Dave T. Nguyen
(74) *Attorney, Agent, or Firm*—Fulbright & Jaworski L.L.P.

(57) ABSTRACT

The present invention relates generally to the fields of nucleic acid transfection. More particularly, it concerns novel polycation:nucleic acid compositions, methods of preparation of such compositions and methods of transfecting cells with such compositions.

103 Claims, 31 Drawing Sheets

OTHER PUBLICATIONS

Goula et al., "Polyethylenimine–based intravenous delivery of transgenes to mouse lung," *Gene Therapy*, 5(9):1291–1295,1998.

Kircheis et al., "Coupling of cell binding ligands to polyethylenimine for targeted gene delivery," *Gene Therapy*, 4:409–418, 1997.

Li et al., "Assesment of recombinant adenoviral vectors for hepatic gene therapy," *Hum Gene Ther.*, 4:403–409, 1993.

Li, et al., "Synthesis and evaluation of water–soluble polyethylene glycol paclitaxel conjugate as a paclitaxel prodrug," *Anti–Cancer Drugs*, 7:642–648, 1996.

Marshall, "Clinical trails—Gene therapy death prompts reviews of adenovirus vector," *Science*, 286(5448): 2244–2245, 1999.

Nicolau and Sene, "Liposome–mediated DNA transfer in eukaryotic cells. Dependence of the transfer efficiency upon the type of liposomes used and the host cell cycle stage," *Biochim Biophys. Acta*, 721:185–190, 1982.

Nicolau et al., "Liposomes as carriers for in vivo gene transfer and expression," *Methods Enzymol.*, 149:157–176, 1987.

Plum et al., "Condensation of DNA by trivalent cations. 2. Effects of cation structure," *Biopolymers*, 30: 631:643, 1990.

Rosenberg et al., "Human gene marker/therapy clinical protocols," *Human Gene Therapy*, 11(6):919–979, 2000.

Rudolph et al., "In vivo gene delivery to the lung using polyethylenimine and fractured polyamidoamine dendrimers," *J. Gene Med.*, 2(4):269–278, 2000.

Smyth Templeton et al., "Improved DNA: liposome complexes for increased systemic delivery and gene expression," *Nature Biotech.*, 15(7):647–652, 1997.

Tomalia et al., "Starburst dendrimers: molecular–level control of size, shape, surface chemistry, topology, and flexibility from atoms to macroscopic matter," *Angew. Chem. Int. Ed. Engl.*, 29:138–175, 1990.

Xu et al., "The contribution of poly–L–lysine, streptavidin, and epidermal growth factor to EGF/PLL/DNA polyplex formation," *Gene Therapy*, 5:1235–1243, 1998.

* cited by examiner

PEI: DNA VECTOR FORMULATIONS FOR IN VITRO AND IN VIVO GENE DELIVERY

This application claims the priority of U.S. Provisional Patent Application Ser. No. 60/235,237, filed Sep. 25, 2000 and U.S. Provisional Patent Application Ser. No. 60/235,635, filed Sep. 26, 2000, both of which disclosures are specifically incorporated herein by reference in their entirety.

The government owns rights in the present invention pursuant to grant number CA66037-05 from the National Institutes of Health.

BACKGROUND OF THE INVENTION

1. Field of the Invention

The present invention relates generally to the fields of nucleic acid transfection. More particularly, it concerns novel polycation:nucleic acid compositions, methods of preparation of such compositions and methods of transfecting cells with such compositions.

2. Description of Related Art

Gene therapy, which involves the delivery and expression of a therapeutic nucleic acid construct to either promote a new gene function, replace a lost gene function, or inhibit current gene function, has evolved into a powerful alternative to many commonly used therapeutics, particularly in the field of cancer therapy (Roth and Cristiano, 1997). The general basis for gene therapy is to transport, deliver, and express a therapeutic nucleic acid construct in a cell to correct abnormal gene function. In cancer gene therapy, while the basis may be the same, a more specific goal often is to mediate cell death in all tumor cells in order to prevent reoccurrence of tumor growth. Unfortunately, the continued development of gene therapy has been slowed not by the ability to identify therapeutic nucleic acid sequences, but by limitations of the delivery composition (Marshall, 1999). The difficulties in obtaining safe and efficient nucleic acid delivery with current nucleci acid vectors has become the single most limiting factor for advancing gene therapy.

The function of the delivery composition is to transport the nucleic acid to the target cell, ensure passage across the target cell membrane, and deliver the nucleic acid into the nucleus for transgene expression. Typically the delivery composition is composed of non-viral or viral components that are used to mediate nucleic acid delivery. In the case of viral components, it is usually replication incompetent or attenuated viruses that are used. Replication defective adenovirus based on serotype 5 is the most commonly used virus in many ongoing cancer gene therapy trials (Rosenberg et al., 2000). This is based on the high transduction efficiency of the delivery composition/vector irrelevant of the cell's replication cycle status. To produce this delivery composition/vector, deletions are typically made in the E1 region of the viral genome (Li et al., 1993). This modification serves two purposes: the delivery composition/vector can then accommodate therapeutic nucleic acid insertion of a limited size, and this renders the virus replication defective.

Unfortunately, the viral genome is still capable of low level expression of viral proteins such as the major hexon coat protein (Yang et al., 1994). This expression occurs at sufficient levels to induce an immune response, which has resulted in continued problems with immunogenicity as well as toxicity (Yang et al., 1994). It has also become apparent that the vector itself is immunogenic and that this immune response may never be overcome in developing future gene therapy delivery compositions based on this virus (Kafri et al., 1998). In addition, the limited size of the inserted nucleic acid has led to problems with utilizing the virus to deliver large or multiple therapeutic nucleic acids. Of greater importance is the fact that this virus is not capable of targeting specific cells, since the expression of the coxackie-adenovirus receptor occurs on many different cell types including both tumor and normal cells (Roelvink et al., 1999). This may even contribute to the virus having a tropism for liver transduction, which can result in hepatotoxicity, particularly if the virus is administered intravenously. Overall, it has become apparent that this delivery composition/vector is immunogenic, difficult to produce economically in large quantities, has a limited therapeutic nucleic acid carrying capacity, a continued dependance upon helper cell lines for production, a lack of targeting, and is still plagued by questions related to safety and toxicity (Marshall, 1999). These issues were recently brought to light when a patient in a clinical trial for ornithine transcarbamylase deficiency died from adenovirus vector related problems (Marshall, 1999).

In contrast to viral delivery compositions, most non-viral delivery compositions are based completely on non-viral components. The three most commonly investigated non-viral delivery composition components are based on formulations involving lipids (e.g., liposomes) (Bendas et al., 1999), polycations (Xu et al., 1998), or simple naked DNA (Chen et al., 2000). Unfortunately, delivery compositions containing these components have had recurrent problems of low transduction efficiency particularly in vivo; naked DNA exhibits the lowest and liposomes exhibit the highest (Bendas et al., 1999; Xu et al., 1998; Chen et al., 2000). In theory, these delivery compositions should also be simple to produce, but there also is a range in ease of delivery composition production; naked DNA requires simple DNA isolation and lipids require complex and extravagant chemical synthesis and formulation (Bendas et al., 1999; Xu et al., 1998; Chen et al., 2000).

Polycations lie in the middle of properties regarding ease of delivery composition production and formulation. Polycations have a self-assembling property when mixed with nucleic acids due to ionic interactions. There have been many studies utilizing the synthetic polycation polyethylenimine (PEI) as a component to deliver nucleic acids to cultured cells as well as to cells in vivo (Bousiff et al., 1995; Boussif et al., 1996; Densmore et al., 2000; Fronsdal et al., 2000; Boletta et al., 1997; Goula et al., 1998; Coll et al., 1999; Kircheis et al., 1997; Hart, 2000; Rudolph et al., 2000). The delivery of plasmids or oligonucleotides has been demonstrated to the brain and kidney (Bousiff et al, 1995; Boletta et al., 1997), and delivery has been demonstrated to the lung (Goula et al., 1998). In addition, this molecule has been used to mediate targeted nucleic acid delivery using proteins such as transferrin that have been chemically coupled to the polycation (Kircheis et al., 1997).

Unfortunately, there are limitations associated with all of these approaches. First, while efficient nucleic acid delivery has been obtained to cultured cells, a survey of the literature shows that a wide range of amine(PEI):phosphate(DNA) ratios are needed to obtain efficient nucleic acid delivery. Second, it has been demonstrated that the direct addition of a targeting ligand to PEI results in targeted, but reduced, nucleic acid delivery (Kircheis et al., 1997). The third and most important limitation is related to toxicity, as high concentrations (amine:phosphate (a:p) ratios of approximately 9:1) of PEI are typically required to obtain high level nucleic acid delivery, but this is at the expense of high level toxicity. When lower amine:phosphate ratios are used, toxicity does drop, but transduction typically drops precipitously when amine:phosphate ratios fall below 6:1.

The utilization of polycations for nucleic acid delivery has led to many different applications for these molecules. One group in particular has been termed, "molecular conjugates" (Cristiano and Roth, 1995). Molecular conjugates are composed of cell and delivery composition specific proteins that have been attached too positively charged polycations. These conjugates bind DNA to form a protein:DNA complex or polyplex (based on the use of polycations) that can target DNA to a specific cell type depending upon the components used. As a result, this delivery composition can consist of at least four types of components that are required for efficient, targeted nucleic acid delivery: a targeting ligand, a polycation for nucleic acid binding:protein attachment, the nucleic acid for RNA and/or protein expression, and an endosomal lysis agent. One drawback of this approach is the large number of components that must be combined to produce an efficient delivery composition. While some components such as the targeting ligand are not absolutely crucial for general nucleic acid delivery, it has been vital for targeted nucleic acid delivery. However, if used, the ligand is attached to DNA using a polycation such as poly-L-lysine (Xu et al., 1998). The ligand and polycation are covalently linked together by one of several different chemicals and is then capable of binding DNA (a polyanion) of any size in a non-damaging, ionic interaction (Xu et al., 1998; Cristiano and Roth, 1995). Unfortunately, problems with low in vivo transduction and high toxicity has limited the use of this vector.

The focus of the work over the past 10 years has been to develop molecular conjugates as efficient, targeted, non-viral delivery compositions for use in gene therapy (Cristiano and Roth, 1995). At least 9 different ligands have been used in molecular conjugates ranging from high molecular weight proteins such as asialoorosomucoid to target hepatocytes, to low molecular weight peptides such epidermal growth factor (EGF) to target lung cancer cells (Xu et al., 1998; Cristiano and Roth, 1995; Cristiano and Roth, 1996). Unfortunately, high level in vitro transduction cannot be obtained with just a targeting ligand, polycation and DNA. It appears to be absolutely crucial that an endosome or vesicle lysis component is incorporated into the delivery composition, especially when receptor-mediated endocytosis or other uptake pathway that results in vesicle formation is utilized for nucleic acid delivery.

Replication defective adenovirus has been used as such an endosome lysis agent.

When targeting with different ligands, high level nucleic acid delivery could only be obtained when the delivery composition was combined with the virus, which is used specifically as an endosome lysis agent, to overcome endosome entrapment of delivery composition (Xu et al., 1998; Cristiano and Roth, 1995; Cristiano and Roth, 1996). Unfortunately, inclusion of the virus causes increased delivery composition related toxicity, size, and immunogenicity, but does not usually increase transduction in vivo (Gao et al., 1993). As a result, the utilization of a molecular conjugate in a delivery composition continues to suffer from three major problems: an inherent degree of complexity based on the number of components required for efficient nucleic acid delivery, the identification of non-viral endosome lysis agents as dependence upon adenovirus for endosome lysis defeats the purpose of developing a non-viral delivery composition, and a lack of efficient in vivo nucleic acid delivery.

Thus, there is still a clear need for nucleic acid delivery compositions that have one or more properties such as low toxicity, high cell transfection efficiency, ease in small or larger scale preparations, and most importantly in cancer gene therapy, the capability of targeting nucleic acid delivery to tumor cells and not normal cells.

SUMMARY OF THE INVENTION

The present invention overcomes the deficiencies in the art by providing novel polycation based nucleic acid delivery compositions that are simple to construct, well suited for scale-up, easily manipulated for targeting, and do not contain viruses/viral components to enhance nucleic acid delivery. This genetic delivery composition and methods of preparation of such delivery compositions also overcomes the deficiencies in the art by providing efficient cell transfection with genetic constructs in formulations having low or reduced toxicity.

The most exciting, novel and innovative aspect of the delivery compositions and formulations disclosed herein lie in the in vitro and in vivo transduction efficiency. A common paradigm for non-viral delivery compositions (e.g. polycation based delivery compositions) is that most are only capable of low level transduction efficiencies with accompanied high toxicity. However, the delivery compositions and methods of formulations described herein can reproducibly produce high level transduction with low level toxicity. A review of the literature shows that no other current single PEI/DNA formulation can obtain the levels of transduction described herein. In addition, most if not all viral and non-viral delivery compositions cannot obtain the level of transduction that was obtained with the novel formulations described herein in the cell lines such as leukemia cell lines.

For example, PEI:DNA in formulations and ratios described herein can produce low-toxicity transduction as high as 90% in bladder, breast, leukemia, lung, prostate, and renal based cancer cell lines. Not only can efficient nucleic acid delivery to many types of cells be obtained with this "generic" form of the delivery composition, but targeted nucleic acid delivery can be mediated by the addition of targeting agents, such as, for example, attaching epidermal growth factor (EGF) to the delivery composition to target EGF receptor overexpressing cells. More importantly, direct injection of the example PEI:DNA delivery composition into subcutaneous tumors produces expression from the transfected nucleic acids >$10^7$ relative light units (RLU)/g tissue and a greater than 50% reduction in tumor size when a therapeutic nucleic acid encoding the tumor suppressor p53 is used.

Therefore, one aspect of the invention provides a method of preparing a liquid transfection composition, comprising (a) providing a liquid medium comprising a polycation; (b) providing a solution comprising a purified nucleic acid; and (c) combining said liquid medium and said solution to produce a liquid transfection composition comprising a polycation and a nucleic acid, wherein said solution comprises a larger volume than said liquid medium or wherein said liquid medium comprises a larger volume than said solution. In one embodiment of the invention, the larger volume comprises a ratio greater than 1:1.2 of said liquid medium to said solution or said solution to said liquid medium, and may also comprise a ration of about 1:1.2 to about 1:1,000,000, including about 1:3, about 1:5, about 1:6, about 1:7, about 1:9, and about 1:10. In further embodiments of the invention, the liquid transfection composition may comprise a molar ratio of polycation moeities to anionic moeities of from about 1:1 to 1,000,000:1, including from about 1:1 to about 6:1, from about 2.4:1 to 2.7:1, from about 1.5:1 to 6:1, and about 2.7:1. The polycation moeities may be amines and the anionic moeities may be phosphates. The liquid transfection composition may further comprise PEG. In certain embodiments of the invention, the liquid transfection composition comprises from about 1% to about 10% or more PEG, including about 1%, 2%, 3%, 4%, 5%, 6%, 7%, 8%, 9% and 10%. The PEG may be added at any time, including following said combining. The combining may comprise a drop-wise addition of said liquid medium to said solution, and may comprise substantially simultaneous addition of said liquid medium to said solution.

The nucleic acid used in the method may be purified by a RNA removal, protein removal or a combination thereof. The RNA removal may comprise lithium chloride purification, RNAse digestion or a combination thereof. The protein removal may comprise protease digestion, organic solvent extraction or a combination thereof. The proteinase digestion may comprise digestion with proteinase K. In certain embodiments of the invention, the polycation may be polyethylenimine, may be branched or linear, and may bind DNA. The polycation can be attached to a ligand, including a targeting or other agent. In certain embodiments, the polycation is an endosome lysis agent. The polycation may also comprises a plurality of amine groups, including primary amines, secondary amines, tertiary amines or a combination thereof. Such amines may be in a 1:2:1 ratio of primary:secondary:tertiary amines.

The method of preparing the vector may further comprise admixing said liquid transfection composition. The admixing may comprise vortexing, tapping or a combination thereof, including allowing the vector to incubate, wherein no additional agitation is necessary. Admixing may be carried out for any time sufficient for mixing, such as about 0.5 second to about 10 minutes, including about 30 seconds. In one embodiment the admixing comprises incubating the composition at room temperature for about 2 to about 5 minutes, and may also be up to about 30 minutes or longer, including about 15 minutes, 25 minutes and 45 minutes. The liquid transfection composition may further comprise any additional desired ingredients, including, for example, glucose, a buffer, a lipid, an additional nucleic acid, an additional polycation, a proteinaceous composition, a linker/coupling agent, an endosome agent, a targeting agent, an anti-cancer agent, a vaccine component, a pharmaceutical carrier or a combination thereof.

In another aspect, the invention provides a method of preparing a liquid transfection composition, comprising: (a) providing a liquid medium comprising a polycation; (b) providing a solution comprising a purified nucleic acid, wherein the nucleic acid is isolated by a method comprising lithium chloride purification; and (c) combining said liquid medium and said solution comprising a purified nucleic acid to produce a liquid transfection composition comprising a polycation and a nucleic acid. In particular embodiments of the invention, the nucleic acid may be isolated by a method comprising RNAse digestion, RNA removal or protein removal or any combinations thereof. In further embodiments of the invention, the protein removal may comprise protease digestion, organic solvent extraction or a combination thereof. The proteinase digestion may comprise digestion with proteinase K. In further embodiments of the invention, the solution may comprise a larger volume than said liquid medium or the liquid medium may comprise a larger volume than said solution. The larger volume may comprise a ratio greater than 1:1.2 of said liquid medium to said solution or said solution to said liquid medium, including from about 1:1.2 to about 1:1,000,000, about 1:3, about 1:5, about 1:6, about 1:7, about 1:9, and about 1:10. In further embodiments of the invention, the molar ratio of polycation moeities to anionic moeities in the solution is from about 1:1 to 1,000,000:1, including from about 1:1 to about 6:1, from about 2.4:1 to 2.7:1, from about 1.5:1 to 6:1, and about 2.7:1.

The polycation moeities may be amines and the anionic moeities may be phosphates. The liquid transfection composition may further comprise PEG. In certain embodiments of the invention, the liquid transfection composition comprises from about 1% to about 10% or more PEG, including about 1%, 2%, 3%, 4%, 5%, 6%, 7%, 8%, 9% and 10%. The PEG may be added at any time, including following said combining. The combining may comprise a drop-wise addition of said liquid medium to said solution, and may comprise substantially simultaneous addition of said liquid medium to said solution.

The liquid transfection composition may further comprise any additional desired ingredients, including, for example, glucose, a buffer, a lipid, an additional nucleic acid, an additional polycation, a proteinaceous composition, a linker/coupling agent, an endosome agent, a targeting agent, an anti-cancer agent, a vaccine component, a pharmaceutical carrier or a combination thereof.

In yet another aspect, the invention provides a method of transfecting a cell comprising the steps of (a) providing a liquid medium comprising a polycation; (b) providing a solution comprising a purified nucleic acid; (c) combining said liquid medium and said solution comprising a nucleic acid, wherein said solution comprises a larger volume than said liquid medium or wherein said liquid medium comprises a larger volume than said solution, to produce a liquid transfection composition comprising a polycation and a nucleic acid; and (d) contacting a cell with said liquid transfection composition. In the method, the transduction efficiency may be greater than about 30%, 50%, 70%, 80%, 90% and about 99%. The transfection composition may further comprise additional ingredients including PEG, glucose, a buffer, a lipid, an additional nucleic acid, an additional polycation, a proteinaceous composition, a linker/coupling agent, a nucleic acid binding agent, a nucleic acid compacting agent, an endosome agent, a targeting agent, an anti-cancer agent, a vaccine component, a pharmaceutical carrier or a combination thereof. The lipid may be, for example, cholesterol, a cholesterol derivative or a combination thereof.

The polycation moeities may be amines and the anionic moeities may be phosphates. The liquid transfection composition may further comprise PEG. In certain embodiments of the invention, the liquid transfection composition comprises from about 1% to about 10% or more PEG, including about 1%, 2%, 3%, 4%, 5%, 6%, 7%, 8%, 9% and 10%. The PEG may be added at any time, including following said combining. The combining may comprise a drop-wise addition of said liquid medium to said solution, and may comprise substantially simultaneous addition of said liquid medium to said solution.

The contacting may produce expression of a RNA encoded by the nucleic acid. However, any nucleic acid could potentially be delivered with the invention, whether a coding sequence or not. Potentially any polypeptide or combination of peptides could be encoded by the nucleic acid. It will be understood to those of skill in the art that the nucleic acid may comprise a collection of different coding or other nucleic acid sequences, or may comprise a single or small number of nucleic acid sequences. Multiple coding sequences may be comprised on the same length of nucleic acid or could be admixed with other coding sequences. Alternatively, multiple vector formulations could be delivered either sequentially, simultaneously or at different times.

The vector may also comprise a coding sequence for a proteinaceous sequence that is translated from an RNA encoded by the nucleic acid. The proteinaceous sequence may having any desired characteristics, and may possess anti-tumor activity. In certain embodiments of the invention, the proteinaceous sequence comprises a sequence of a tumor suppressor gene or reporter gene. The toxicity may kill less than about 20% of contacted cells or not reduce cell number beyond 24 hrs after administration of a nucleic acid delivery composition. Any cell could be targeted, including a rapidly dividing cell and a tumor cell. The cell may be comprised in an organism, including a mammal such as a human. The vector formulation may also be targeted to the cell.

In still yet another aspect, the invention provides a method of reducing the growth of cancer cells, comprising the steps of: (a) providing a liquid medium comprising a polycation; (b) providing a solution comprising a purified nucleic acid, wherein said nucleic acid encodes an anti-cancer nucleic acid or proteinaceous sequence; (c) combining said liquid medium and said solution, wherein said solution comprises a larger volume than said liquid medium, to produce a liquid transfection composition comprising a polycation and a nucleic acid; and (d) contacting cancer cells with said liquid transfection composition.

In still yet another aspect, the invention provides a transfection composition, comprising a polycation and a nucleic acid, prepared by the steps of: (a) providing a liquid medium comprising a polycation; (b) providing a solution comprising a purified nucleic acid; and (c) adding said liquid medium to a solution comprising a nucleic acid, wherein said solution comprises a larger volume than said liquid medium, to produce a liquid transfection composition.

In still yet another aspect, the invention provides a transfection composition comprising a polycation and a nucleic acid, wherein said transfection composition has a transduction efficiency of greater than 30% upon contact with a cell, said composition comprising a cationic moeity:anionic moeity ratio of less than about 3:1. In one embodiment, the cationic moeity comprises an amine, and the anionic moeity comprises a phosphate. In certain embodiments, the composition comprises a polycation to nucleic acid ratio of less than 3:1.

In still yet another aspect, the invention provides a transfection composition comprising polyethylenimine and nucleic acid, wherein said transfection composition comprises an amine to phosphate ratio of less than 8:1. In further embodiments of the invention, the composition comprises an amine to phosphate ratio of from about 1:3 to about 7:1, about 1:1 to about 6:1, about 1.5:1 to about 5:1, about 2:1 to about 4:1, about 2.3:1 to about 3.5:1, about 2.5:1 to about 3:1 and about 2.7:1. In certain embodiments of the invention, the transfection composition comprises from about 1% to about 10% or more PEG, including about 1%, 2%, 3%, 4%, 5%, 6%, 7%, 8%, 9% and 10%. The PEG may be added at any time, including following said combining. The combining may comprise a drop-wise addition of said liquid medium to said solution, and may comprise substantially simultaneous addition of said liquid medium to said solution.

The transfection composition may further comprise additional ingredients including glucose, a buffer, a lipid, an additional nucleic acid, an additional polycation, a proteinaceous composition, a linker/coupling agent, a nucleic acid binding agent, a nucleic acid compacting agent, an endosome agent, a targeting agent, an anti-cancer agent, a vaccine component, a pharmaceutical carrier or a combination thereof. The lipid may be, for example, cholesterol, a cholesterol derivative or a combination thereof.

In certain embodiments of the invention, the nucleic acid comprises a coding sequence, including a tumor suppressor coding sequence, or an other coding sequence with anti-tumor activity. An exemplary coding sequences are p53 and thymidine kinase. However, any coding or non-coding sequence may be used. The composition may be targeted, for example, using EGF.

The nucleic acid used in the composition may be purified by a RNA removal, protein removal or a combination thereof. The RNA removal may comprise lithium chloride purification, RNAse digestion or a combination thereof. The protein removal may comprise protease digestion, organic solvent extraction or a combination thereof. The proteinase digestion may comprise digestion with proteinase K.

In still yet another aspect, the invention provides a method of delivering at least a first selected nucleic acid to a cell comprising the steps of: (a) obtaining a transfection composition comprising polyethylenimine and a selected nucleic acid, wherein said transfection composition comprises an amine to phosphate ratio of less than 8:1; and (b) contacting at least a first cell with said transfection composition.

The transfection composition may further comprise additional ingredients including glucose, a buffer, a lipid, an additional nucleic acid, an additional polycation, a proteinaceous composition, a linker/coupling agent, a nucleic acid binding agent, a nucleic acid compacting agent, an endosome agent, a targeting agent, an anti-cancer agent, a vaccine component, a pharmaceutical carrier or a combination thereof. The lipid may be, for example, cholesterol, a cholesterol derivative or a combination thereof.

In certain embodiments of the invention, the transfection composition comprises from about 1% to about 10% or more PEG, including about 1%, 2%, 3%, 4%, 5%, 6%, 7%, 8%, 9% and 10%. The PEG may be added at any time, including following said combining. The combining may comprise a drop-wise addition of said liquid medium to said solution, and may comprise substantially simultaneous addition of said liquid medium to said solution.

In certain embodiments of the invention, the nucleic acid comprises a coding sequence, including a tumor suppressor coding sequence, or an other coding sequence with anti-tumor activity. An exemplary coding sequences are p53 and thymidine kinase. However, any coding or non-coding sequence may be used. The composition may be targeted, for example, using EGF.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13A shows transduction analysis of H1299 and HTB9 cells. FIG. 13B shows quantitation of β-gal gene expression in each cell line.

Antibiotin-B-PEI/DNA vector, 4) EGF/Antibiotin-B-PEI/DNA vector, EGF/Antibiotin-B-PEI/DNA vector+100-Fold EGF. B=Biotin.

Figure 25:
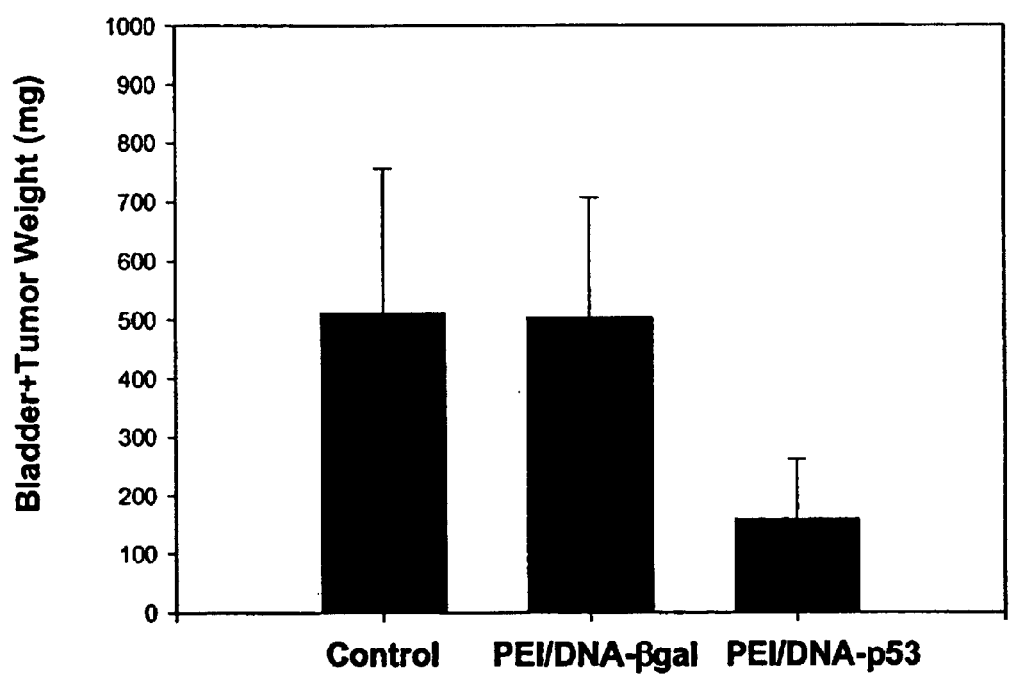

FIG. 25. Growth analysis of UC3 orthotopic bladder tumors following intravenous injection of either HEPES Buffer (HB) or PEI/DNA vector carrying either the p53 or β-gal gene. Samples were injected every three days for three weeks. Animals were then euthanized and bladder+tumor weight compared between each group. p>0.003, PEI/DNA-p53 injected group vs. PEI/DNA-β-gal injected group.

Figure 26:
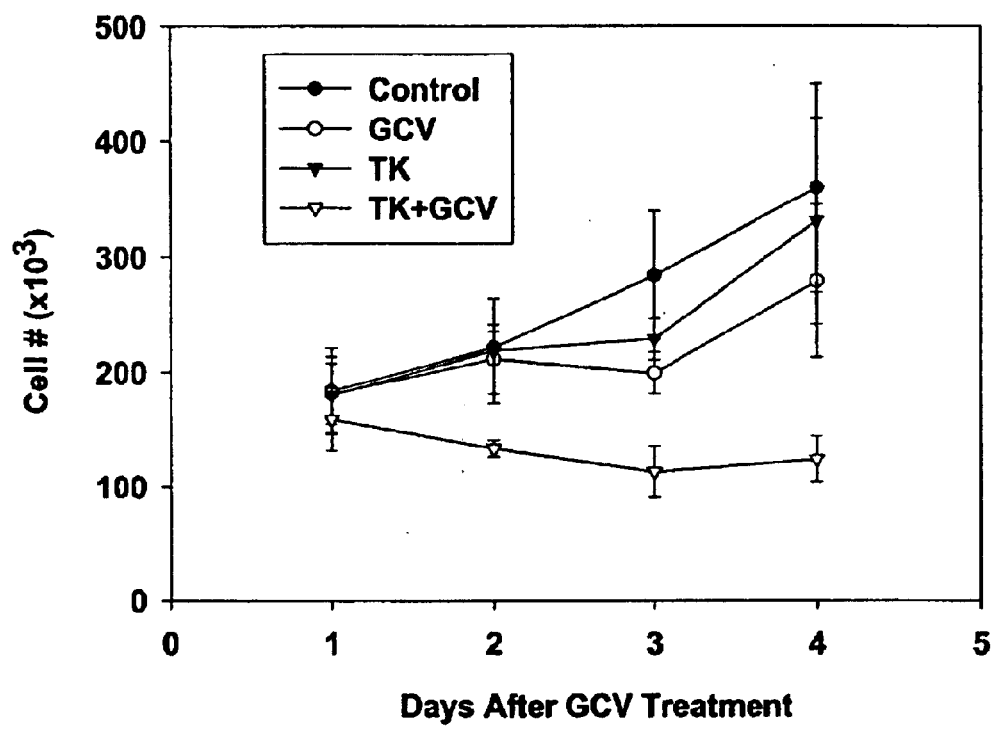

FIG. 26. Delivery of the HSV-TK gene by the PEI/DNA vector. Control (MCF-7 cells only), GCV (15 µM GCV only), TK (PEI/DNA vector containing the HSV-TK gene), and TK-GCV (PEI/DNA vector containing the HSV-TK gene+GCV, 15 µM).

Figure 27:
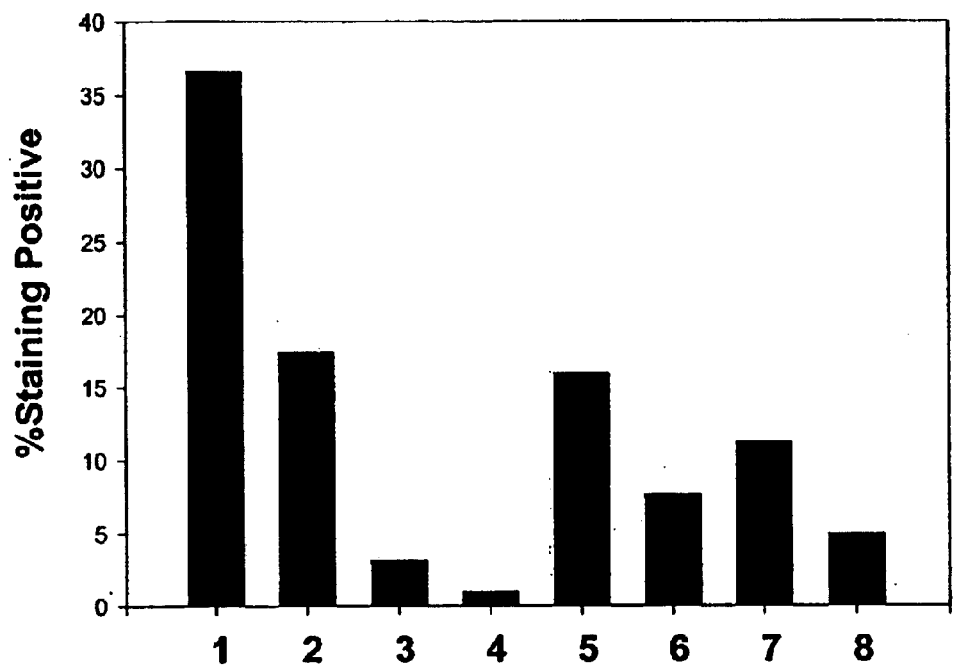

FIG. 27. Analysis of the affect of vector formation volume on vector formation efficiency (based on transduction). Samples (represented as volumes of PEI:DNA:HEPES Buffer in µl; 1) 10:60:0, 2) 10:60:490, 3) 10:270:280, 4) 10:550:0, 5) 40:240:280, 6) 80:480:0, 7)140:140:280, and 8) 280:280:0. Only reaction 1 was added onto cells in a volume of 30 µl, while all others were added in 280 µl.

Figure 28:
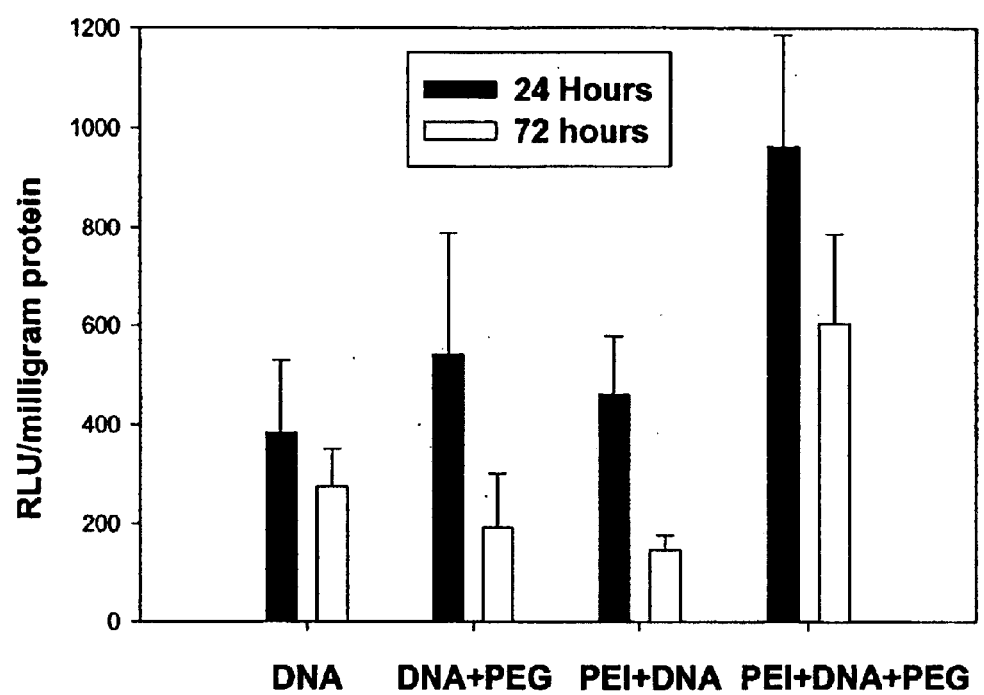

FIG. 28. Analysis of the affect of PEG on PEI/DNA vector mediated gene delivery in vivo following an intravenous administration.

DESCRIPTION OF ILLUSTRATIVE EMBODIMENTS

The development of non-viral nucleic acid delivery compositions based on molecular conjugates and protein:DNA polyplexes has created the ability to target therapeutic nucleic acids to specific cell types through the receptor-mediated pathway. Unfortunately, this results in endosome entrapment of delivery composition unless an agent is used to mediate endosome release. Replication defective adenovirus was first used in this role, which resulted in efficient endosome release, but this component also contributes to toxicity, increases delivery composition complexity, and causes problems with immunogenicity.

As a result, studies have been conducted focusing on using synthetic agents that can replace the function of adenovirus while decreasing delivery composition complexity. Polyethylenimine is a branched chain polycation that is capable of mediating endosome release as well as acting as both a DNA-binding agent and a point of ligand attachment. Studies have demonstrated that the highest amount of transduction that could be obtained was at an amine to phosphate ratio of 8:1, resulting in variable transduction efficiencies as high as 30% to 40%. However, this transduction efficiency was coupled with high toxicity, such as a undesirably high level of cell death (Goula et al., 1998).

To overcome these and other deficiencies in the art, novel polycation:nucleic acid delivery composition formulation methods and compositions are described herein. These delivery composition formulations were obtained by a combination of variables that produced a surprising and unexpected ability to transfect and express the genetic construct in cells, while maintaining low toxicity to the cells. As used herein, low toxicity may mean a reduction in cell number of cells that are desired to survive of less than about 20% and/or a reduction in cell number of cells that are desired to survive that does not continue beyond 24 hrs after administration of a nucleic acid delivery vehicle and/or additional agent. These variables comprise using DNA isolated from a specific DNA isolation method in combination with a specific method of combining the polycation with DNA.

The specific examples described herein demonstrate the preparation of a preferred polycation, PEI, with DNA. The resulting novel PEI:DNA delivery composition formulations described herein achieves reproducible transduction levels as high as 90% in cultured bladder, brain, breast, kidney, lung, and prostate cancer cell lines. More surprisingly, transduction efficiencies as high as 99% could be achieved in cultured leukemia cell lines which are usually very difficult to transduce with most viral and non-viral delivery compositions. This level of transduction also demonstrated very low toxicity as amine:phosphate ratios of 3:1 or less, including 2.7:1, were utilized.

Efficient transduction also was obtained in vivo. An intralesional injection of just 6 to 12 micrograms of delivery composition into a subcutaneous tumor generated $10^8$ RLU/gram tissue. In addition, a similar dose of delivery composition given 7 times over a 14-day period resulted in a >50% reduction in tumor size when the tumor suppressor p53 gene was delivered. The novel formulations can also be targeted to specific cells as the addition of a targeting agent, such as, for example, EGF, to the delivery composition. The addition of the EGF targeting agent resulted in at least a 2-fold increase in nucleic acid delivery efficiency.

Such high nucleic acid delivery in addition to the ability to being targeted are rare. It is contemplated that the formulations described herein will be useful in therapeutic applications such as gene therapy. More importantly, the simplicity of the delivery composition allows the use of any type or size of therapeutic genetic constructs to be complexed and delivered, thus removing the need for packaging cell lines.

These delivery composition formulations also allow improving delivery composition mediated transduction, including but not limited to improved the ability of the plasmid to express the delivered nucleic acid, combining the delivery composition with other common therapies such as, for example, irradiation or chemotherapy to improve therapeutic efficacy, and improving the delivery composition through targeting. It is contemplated that these formulations may have all such utilities in transfecting organelles, cells, tissues, organs and organisms, such as humans. Thus, it is particularly contemplated that the compositions and methods of the present invention may have such applicability in therapy of human patients.

These novel delivery composition formulations may be used for the treatment of all forms of cancer that can be treated by gene therapy. Extended transfection of tumor suppressor and therapeutic nucleic acid constructs may now be done without a concern of viral gene expression may now be done. This formulation technique provide a safe, simple, cost effective, and efficient method with which to deliver DNA to tumor cells in vitro and in vivo. The compositions and methods of the present invention may enhance the bioavailability of nucleic acids administered to organism at particular tissue or cell cites (e.g., tumor sites) by improving their pharmacokinetic properties.

It is further contemplated that the biodistribution of delivery compositions of the present invention, may be altered by changing various aspects of the delivery composition, including but not limited to size, charge or composition components. In certain embodiments, it is contemplated that biodistribution may be altered by the conjugation of targeting ligands to one or more components of the delivery composition, described herein. Such ligands may allow cell, tissue and/or organ specific accumulation of the delivery composition.

In other embodiments, it is contemplated that improved toxicity profiles and/or therapeutic efficacy of a nucleic acid, delivery composition component and/or delivery composition may be produced by the methods of the present invention. Such aspects can be determined by procedures in cell cultures or experimental animals known to those of ordinary skill in the art or described herein. For example, one measure of drug effectiveness, cell toxicity, and safety of a compound is its therapeutic index: $LD_{50}/ED_{50}$. $LD_{50}$ is the median lethal dose, i.e., the dose lethal to 50% of the population, and $ED_{50}$ is the median effective dose, i.e., the dose required to achieve a specific effect in 50% of the population (e.g., anti-tumor activity). As would be understood by one of ordinary skill in the art, compositions having the highest therapeutic index ($LD_{50}/ED_{50}$) are desirable in clinical settings. In certain aspects, the therapeutic index should be greater than 2, preferably at least 10, more preferably at least 50. It is also contemplated that other pharmacokinetic or pharmacodynamic parameters (e.g., clearance, volume of distribution, half-life, drug release profiles) of the delivery compositions of present invention may be superior to other preparations of polycations and nucleic acids. Such parameters are well known in the art (see, for example, Goodman and Gilman's "The Pharmacological Basis of Therapeutics", pp. 18–32, 43–61, 66–78, Eighth Edition, 1990, incorporated herein by reference in relevant part).

A. Nucleic Acid Delivery Compositions

In certain embodiments, the nucleic acid delivery compositions of the present invention comprise at least one polycation and at least one nucleic acid. In further embodiments, the delivery composition further comprises at least one additional agent, including, but not limited to a targeting agent (e.g., a targeting ligand), an endosome lysis agent, a linker/coupling agent, a proteinaceous compound, a lipid, a drug, an anti-cancer agent, a vaccine component, a pharmaceutically acceptable carrier or any combination thereof such agents. In a non-limiting example, a composition of the present invention may comprise a polycation attached to a linker/coupling agent, which is attached to a targeting agent. In another non-limiting example, a composition of the present invention may comprise a polycation and a nucleic acid in a liposome which comprises a targeting agent. Of course, other combinations of nucleic acid delivery composition components are described herein, and additional combinations will be readily apparent to one of skill in the art from the disclosures herein, and are thus encompassed by the present invention. The various components of a nucleic acid delivery composition may be associated to each other by means including, but not limited to, covalent bonds, ionic interactions, hydrophobic interactions or combinations thereof.

In particularly preferred embodiments, the polycation, nucleic acid, and any additional agent are prepared by the methods described herein. For example, it is particularly preferred that a nucleic acid is prepared in accordance with the methods of the present invention. In other embodiments, it is particularly preferred that a polycation is combined with a nucleic acid by the methods described herein.

1. Polycations

Polycations have the advantages of self-assemble when combined with a nucleic acid (e.g., DNA, RNA, PNA or combinations thereof), making them simple to use, and are commercially available, inexpensive and do not require difficult synthesis strategies. It is contemplated that any polycation described herein or as would be known to one of ordinary skill in the art may be used in the compositions and methods described herein.

Polycations also possess the advantages of the ability to serve as a point of a binding ligand and/or chemical moeity attachment, such as through, for example, a covalent bond. Most importantly, some polycations possess an ability to function in the role of an endosome lysis agent, and thus can increase the passage of DNA into the cells cytoplasm. The high number of cationic chemical moeities (e.g., amines) allows the molecule to act as a "proton sponge", using its cationic moeities to absorb hydrogen ions during the acidification of the endosome which leads to endosome lysis. Polycations that can serve as endosome lysis agents are preferred in certain embodiments of the present invention.

In certain embodiments, a polycation may condense a nucleic acid by electrostatic charge-charge interactions (Plum et al., 1990). For example, the neutralization and condensation of DNA by polycations, such as polylysines, into small (ca 100 nm) toroid-like structures, promotes the endocytosis of the nucleic acid into cells in vitro (U.S. Pat. No. 5,972,600, incorporated herein by reference). The neutralization of a nucleic acid's negative charge may aid transfections, as cells surfaces are often negatively charged (Stevenson et al., 1989; Lemaitre et al., 1987). Additionally, polycations, such as, for example, polylysines also destabilize cell membranes, and may be used as a site for the attachment of additional agents. (U.S. Pat. No. 6,071,533, incorporated herein by reference).

In certain embodiments, the number of monomers in an individual polycation chain can be of from 3 to about 1000 monomers, and any integer derivable therein and any range derivable therein. Of course, in various aspects mixtures of polycation chains of different lengths can be used. In other embodiments, the number of cationic moeities on a particular polycation chain may comprise of from 3 to about 1000 monomers, and any integer derivable therein and any range derivable therein. In specific aspects, the number of cationic moeities or charges is matched to, or approximates the number of anionic moeities or charges in a nucleic acid, proteinaceous composition, or composition of the present invention.

In certain embodiments, the polycation is a polyamine, such as, for example, spermidine, spermine, polyammonium molecules such as, for example, polybrene (hexadimethrine bromide), basic polyamino acids (e.g., polylysine), basic proteins or a combination thereof. Other polycations include, but are not limited to, those described in U.S. Pat. Nos. 5,656,611, 5,354,844, 5,462,866, 5,462,866 and 5,494,682, each incorporated herein by reference.

In other embodiments, the polycation is a protamine, histone, heterologous polypeptide, non-peptide cations such as polyethyleneimines, or a combination thereof (U.S. Pat. No. 5,792,645, incorporated herein by reference).

In other embodiments, a polycation may comprise, for example, a cationized albumin, DEAE-dextran, a histone, polybrene, polyornithine, protamine, spermine, a cascade amidoamine "dentritic" polymer, gramicidin S cyclic peptide, spermidine, polylysine, such as, for example, the (bromide salt, mol. wt. 25,600; Sigma Chemical Corporation St. Louis, Mo.), a short, synthetic cationic peptide, or combinations thereof (U.S. Pat. No. 5,908,777; Haensler and Szoka, 1993, each incorporated herein by reference).

U.S. Pat. No. 5,260,002 describes various polymers. In is contemplated that the cationic members of these polymers (e.g., gelatin), as would be understood by one of ordinary skill in the art, may be used as a polycation of the present invention. Such polymers include NIH Approved Implantable materials, including, polyacids such as polyacrylates (e.g., sodium), polymethacrylates and olefinmMaleic anhydride copolymers; polyesters, such as polyglycolic acid, poly lactic acid, poly caprolactane and copolymers of these polyesters; polyorthoesters, such as polydioxyalkyltetrahydrofuran and poly 3,9-bismethylene-2,4,8,10 tetra aspiro 5,5 undecane-co-1,6 hexanediol; hydrogels, such as, hydroxyethylmethacrylate, polyethyleneglycol, monomethyacrylate and gelatin crosslinked with formaldehyde; polysaccharides such as cellulose and dextran; polypeptides, such as, polyglutamic acid, glutamic acid leucine copolymers, polyaminotriazole/alkyleneaminotriazole copolymers and albumin beads (i.e, albumin crosslinked with glutaraldehyde); amino acid polymers, such as poly D- or L-lysine HCL, poly D- or L-ornithine HCL and poly D- or L-arginine; and combinations thereof. Other polymers described included water soluble polymers such as polysaccharides (−): starch, gums, carrageenans, dextran, xanthan, sulfated algal polysaccharide (−), alginate (−), hyaluronic acid films (−), heparin (−), chondroitin sulfates (−), polygalacturonic acid (−), alginic acid (−), sodium carboxymethylcellulose (−), sodium carboxymethylcellulose-diethylaminoethyldextran copolymer (−), agar, hyaluronate (−), sulfated hyaluronic acid (−), sulfated deacetylated hyaluronic acid (−), heparin (−), polyguluronate (normal or acetylated) (−), polymannuronate (−), chondroitin sulphate (−), ascopyllan (−), pectin (made of 1,4 polyglacteronic acid) (−), dextran sulfate (−), fucoidan (−), oxdized cellulose (−), polypeptides and proteins such as hydrophobic (e.g., polyphenylalanine), polar (e.g., serine), acidic (−) (e.g., asparatic acid, chondroitin-6-sulfate, heparin, human serum albumin, basic (+) (e.g., lysine, 1-argine, collagen); polynucleic acids (RNA, DNA) (nonionic), pullan (nonionic), cellulose (nonionic), algal pectin, modified celuloses such as hydroxypropylcellulose (nonionic, forms a thin film), hydroxypropylcellulose (nonionic), carboxymethylcellulose (nonionic); forms a gel/film, diethylaminohydroxypropylcellulose (+), diethylaminoethylcellulose (+) and chitosan (+). Other polymers disclosed include synthetic polymers, such as the nonionic polymers polyacrylamide, polymethacrylamide, polyvinyl alcohol films; the anionic polymers poly sodium acrylate, polystyrene sodium sulphate, polyvinyl sulphonic acid salts, polyvinyl benzoic acid salts, polyvinyloxypropanesulphonic acid salts, poly 4-vinylphenol salts, polyvinylsucciniumidum acid salts, sodium-2-sulfoxyethyl methacrylate, sodium-2-acrylamido-2-methylpropane sulphate and sodium-3-acrylamido-3-methyl butanoate; and cationic polymers dimethylaminoethyl methacrylate, dimethylaminoethyl acrylate, diethylaminoethyl methacrylate, diallydimethylammonium chloride, metharylryloxyethyltrimethyl ammonium sulfate, metharylryloxyethyltrimethyl ammoniumchloride, 3-methacrylamidepropyltrimethyl ammonium chloride, polyvinyl pyridine (Blood plasma substitute), quaternerized polyvinylpyridine, polyethyleneimin, linear, polymethylene-N,N-dimethyl piperdinium, polyvinyl 4-alkyl pyridinium, polyvinylbenzenetrimethyl ammonium chloride, 2-acrylamido-2-methylpropanedimethylammonium chloride and 1,3 sulfopropyl-2-vinyl pyridinium.

a. Polyethylamine

In certain embodiments, branched chain polycations are preferred. A particularly preferred branched chain polycation is the synthetic polycation polyethylenimine (PEI). In one embodiment of the invention, PEI with a molecular weight of 25,000 is used. PEI possesses a high number of amine groups which are arranged in a 1:2:1 ratio of primary:secondary:tertiary amines, which is thought to contribute to its function as a proton sponge and endosome lysis agent. Non-limiting example, novel PEI:DNA delivery composition formulations that are capable of highly efficient in vitro and in vivo nucleic acid delivery are described herein.

b. Dendrimer Polycations

In certain embodiments, the polycation comprises a dendrimer polycation. Dendrimer polycations and methods of preparing them are described in Tomalia et al., 1990; PCT/US83/02052; U.S. Pat. Nos. 6,113,946, 4,507,466, 4,558,120, 4,568,737, 4,587,329, 4,631,337, 4,694,064, 4,713,975, 4,737,550, 4,871,779 and 4,857,599, each incorporated herein by reference. Dendrimer polycations generally comprise oligomeric and/or polymeric compounds attached to a core molecule. As used herein "attached" may include, but is not limited to, such attachment means as a covalent bond.

Examples of oligomers and polymers for use in dendrimer polycations include, but are not limited to, polyamidoamines, including but not limited to, methyl acrylate, ethylenediamine or combinations thereof. In certain embodiments the oligomers or polymers are cationic (i.e., capable of being positively charged). In other embodiments, a cationic moiety is attached to the oligomer or polymer. Such cationic moieties include, but are not limited to, guanidinium; azoles, including primary, secondary, tertiary, or quaternary aliphatic or aromatic azoles, and/or S, O, guanidinium or combinations thereof substituted azoles; amides, including primary, secondary, tertiary, or quaternary aliphatic or aromatic amines, and/or S, O, guanidinium or combinations thereof substituted amides; and combinations of guanidinium, azoles and/or amides. The oligomers or polymers may comprise reactive moeities other than cationic moeities. Such reactive moeities include, but are not limited to, hydroxyl, cyano, carboxyl, sulfhydryl, amide, thioether or combinations thereof. The cationic or reactive moeities may comprise or be attached to about 1% to about 100%, and any integer derivable therein, and any range derivable therein, of the oligomer or polymers, or monomers that comprise the oligomers or polymers.

Core molecules include, but are not limited to, ammonia, ethylenediamine, lysine, ornithine, pentaerythritol, tris-(2-aminoethyl)amine or combinations thereof. Core molecules generally comprise at least two reactive moeities that attach the oligomeric and/or polymeric compounds. Such reactive moeities including but not limited to, amino, carboxyhalide maleimide, carboxyl, dethiopyridyl, ester, halide, hydroxyl, imido, imino, sulfhydryl or combinations thereof. Pharmaceutically acceptable core molecules, oligomers and/or polymers are preferred in certain embodiments.

Typical dendrimer polycations are about 2,000 to about 1,000,000 average MW, and any integer derivable therein, and any range derivable therein. Typical dendrimer polycations have a hydrodynamic radius of about 11 to about 60 ANG., and any integer derivable therein, and any range derivable therein.

c. Proteinaceous Polycations

In certain embodiments, the polycation comprises a cationic proteinaceous sequence. Such cationic proteinaceous sequences will preferably comprise one or more cationic amino acid residues or one or more cationic moieties attached to the cationic proteinaceous sequence.

As used herein, the term "cationic proteinaceous sequence" include, but is not limited to, mixtures of cationic residues, in d and/or l conformation, and/or attached cationic moeities. In certain preferred embodiments, the term "cationic proteinaceous sequence" include amino acid chains comprising one or more arginine, histidine and/or lysine, of either d and/or l isomer conformation. Cationic proteinaceous sequences may also comprise any natural, modified, or unusual amino acid described herein, as long as the majority of residues, i.e., greater than 50%, comprise cationic residues and/or cationic moeities attached to residues of the cationic proteinaceous sequence. A polycationic proteinaceous sequence that comprises more than one different type of amino acid residue is sometimes referred to herein as a "co-polymer."

Preferred cationic proteinaceous sequences include, but are not limited to poly(1-arginine acid), poly(d-arginine acid), poly(dl-arginine acid), poly(1-histidine acid), poly(d-histidine acid), poly(dl-histidine acid), poly(-lysine), poly(d-lysine), poly(dl-lysine), copolymers of the above listed polyamino acids with polyethylene glycol, polycaprolactone, polyglycolic acid and polylactic acid, as well as poly(2-hydroxyethyl 1-glutamine), chitosan, carboxymethyl dextran, hyaluronic acid, human serum albumin, and/or alginic acid. In certain embodiments, the cationic proteinaceous sequences of the present invention have a molecular weight of about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000 about 28,000, about 29,000, about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, about 50,000, about 51,000, about 52,000, about 53,000, about 54,000, about 55,000, about 56,000, about 57,000, about 58,000, about 59,000, about 60,000, about 61,000, about 62,000, about 63,000, about 64,000, about 65,000, about 66,000, about 67,000, about 68,000, about 69,000, about 70,000, about 71,000, about 72,000, about 73,000, about 74,000, about 75,000, about 76,000, about 77,000, about 78,000, about 79,000, about 80,000, about 81,000, about 82,000, about 83,000, about 84,000, about 85,000, about 86,000, about 87,000, about 88,000, about 89,000, about 90,000, about 91,000, about 92,000, about 93,000, about 94,000, about 95,000, about 96,000, about 97,000, about 98,000, about 99,000, to about 100,000 kd, and any integer derivable therein, and any range derivable therein.

In certain embodiments, various substitutions of naturally occurring, unusual, or chemically modified amino acids may be made in the amino acid composition of the cationic proteinaceous sequences, to obtain molecules having like or otherwise desirable characteristics. For example, a polyamino acid such as poly-arginine, poly-histidine, poly-lysine, or cationic proteinaceous sequences comprising a mixture of arginine, histidine, and/or lysine, may have about 1, about 2, about 3, about 4, about 5, about 6, about 7, about 8, about 9, about 10, about 12, about 13, about 14, about 15, about 16, about 17, about 18, about 19, about 20, about 21, about 22, about 23, about 24, or about 25 or so, and any range derivable therein, of arginine, histidine or lysine, residues, respectively, substituted by any of the naturally occurring, modified, or unusual amino acids described herein. In other aspects of the invention, a cationic proteinaceous sequence such as poly-arginine, poly-histidine, poly-lysine, or a amino acid chain comprising a mixture of some or all of these three amino acids may have about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, to about 50% or so, and any range derivable therein, of the arginine, histidine or lysine residues, respectively, substituted by any of the naturally occurring, modified, or unusual amino acids described herein, as long as the majority of residues comprise histidine, arginine and/or lysine, or attached cationic moeities.

Such substitutions of non-cationic residues and/or moeities to a polyamino acid may provide a convenient chemical moeity for attachment of additional agents, such as, for example, a targeting agent (e.g., a targeting ligand), an endosome lysis agent, a linker/coupling agent, a drug, an anticancer agent or combinations thereof. In a non-limiting example, a glutamic acid residue comprises s side chain carboxyl functional group that can be used to covalently attach agents such as, for example, a drug. Of course, cationic residuce may also serve as points of attachment for one or more additional agents. Such methods of chemical attachment are described herein, and well known to those of ordinary skill in the art (see for example, Li et al., 1996; Greenwald et al., 1996; Van Heeswijk et al., 1985; Hoes et al., 1985; Hirano et al., 1979; Kato et al., 1984; Morimoto et al., 1984; and U.S. Pat. No. 5,362,831, each incorporated herein by reference). In certain aspects the attachment of one or more nucleic acid delivery composition components may be by a covalent bond directly attaching the agents. In other aspects, the attachment may be by a linker/coupling agent.

2. Linkers/Coupling Agents

If desired, the nucleic acid delivery composition component(s) of interest may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

In certain embodiments, polyethylene glycol (PEG) is contemplated as a linker/coupling agent. It is contemplated that polyethylene glycol may coat the polycation/nucleic acid combination, as well as serve as a point of attachment for additional agents such as, for example, targeting ligands. In certain embodiments, for example, the PEG may be attached to the other nucleic acid delivery components by charge (e.g., ionic interactions) and/or covalent bonds. For example, heterobifunctional PEG comprising one or more coupling groups (e.g., a coupling group at each end the PEG molecule) may be covalently bonded to, for example, a polycation and a targeting agent.

In other embodiments, it is contemplated that bispecific antibodies may be used as a linker/couping agent. For example, a bispecific antibody may bind one or more components of the nucleic acid delivery composition, and foster binding to another agent. An example of this is described in Example 11.

Additionally, while numerous types of disulfide-bond containing linkers are known which can successfully be employed to conjugate moeities, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moeity prior to binding at the site of action.

Cross-linking reagents are used to form molecular bridges that tie together functional groups of two different molecules, e.g., a stablizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another

TABLE 2

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one proteinaceous compound (e.g., a selected antibody or fragment) and through the thiol reactive group, the cross-linker, already tied up to the first proteinaceous compound, reacts with the cysteine residue (free sulfhydryl group) of the other proteinaceous compound (e.g., another agent agent).

It is preferred that a cross-linker having reasonable stability in blood will be employed. Numerous types of disulfide-bond containing linkers are known that can be successfully employed to conjugate various agents. Linkers that contain a disulfide bond that is sterically hindered may prove to give greater stability in vivo, preventing release of an agent, such as, for example, a targeting agent, prior to reaching the site of action. These linkers are thus one group of linking agents.

possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteinaceous compounds, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of an agent. Preferred uses include adding a free amino or free sulfhydryl group to a proteinaceous molecule, such as, for example, an antibody or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

3. Proteinaceous Components

In certain embodiments, the present invention concerns novel nucleic acid delivery compositions comprising at least one proteinaceous molecule. As used herein, a "proteinaceous molecule", "proteinaceous composition", "proteinaceous compound", "proteinaceous chain", "proteinaceous sequence" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500, about 2750, about 3000, about 3250, about 3500, about 3750, about 4000, about 4250, about 4500, about 4750, about 5000, about 6000, about 7000, about 8000, about 9000, about 10000 or greater amino molecule residues, and any integer derivable therein, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moeities. In particular embodiments, the sequence of residues of the proteinaceous molecule may be interrupted by one or more non-amino molecule moeities.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | Ahyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Organisms include, but are not limited to, Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. It is contemplated that antibodies to specific tissues may bind the tissue(s) and foster tighter adhesion of the glue to the tissues after welding. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred in certain embodiments that the proteinaceous material is biocompatible and/or pharmaceutically acceptable. Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. The "autologous protein, polypeptide or peptide" may then be used as a component of a composition intended for application to the selected animal or human subject. In certain aspects, the autologous proteins or peptides are prepared, for example from a biological sample from a selected donor.

4. Endosome Lysis Agents

In some embodiments, the compositions of the present invention comprise an agent that improves endosomal uptake of the composition and/or reduces endosomal degradation. Such agents include, but are not limited to, an agent that acts as a base or buffer, such as, for example, chloroquine or ammonium chloride, an agent that disrupts endosome membranes, such as, for example, fusogenic peptides, or combinations thereof such agents. Fusogenic peptide include, but are not limited to, those derived from the N-terminus of the IIA influenza virus protein or inactivated adenovirus capsids (U.S. Pat. Nos. 6,083,741 and 5,908,777, each incorporated herein by reference).

In certain embodiments, an endosome lysis agent may comprise all or part of the amino acid sequences of transferrin, asialoorosomucoid, insulin or a combination thereof (U.S. Pat. Nos. 5,792,645 and 5,972,600, incorporated herein by reference).

5. Targeting Agents

In certain embodiments, nucleic acid delivery compositions described herein may comprise at least one targeting agent to an organelle, cell, tissue, organ or organism. It is contemplated that any targeting agent described herein or known to one of ordinary skill in the art may be used in the compositions and methods of the present invention, either alone in combination with other targeting agents. In specific embodiments, the targeting agent may be attached to, for example, a polycation, nucleic acid, and/or other composition component.

Various agents for targeting molecules to specific cells, tissue, organs and organisms are known to those of ordinary skill in the art, and may be used in the methods and compositions of the present invention. In certain embodiments, for example, targeting agents may include, but are not limited to, EGF, transferrin, an anti-prostate specific membrane antigen antibody, endothelial specific peptides and bone specific ligands.

In another non-limiting example, a targeting agent may comprise an antibody, cytokine, growth factor, hormone, lymphokine, receptor protein, such as, for example CD4, CD8 or soluble fragments thereof, a nucleic acid which bind corresponding nucleic acids through base pair complementarity, or a combination thereof (U.S. Pat. No. 6,071,533, incorporated herein by reference). In other embodiments, the targeting ligand may comprise a cellular receptor-targeting ligand, a fusogenic ligand, a nucleus targeting ligand, or a combination thereof (U.S. Pat. No. 5,908,777, incorporated herein by reference). In another non-limiting example, the targeting ligand may comprise an integrin receptor ligand, described in U.S. Pat. No. 6,083,741, incorporated herein by reference.

Still further, a nucleic acid delivery composition may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated nucleic acid targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated nucleic acid transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

6. Lipid Components

In certain embodiments, the novel nucleic acid delivery compositions of the present invention may comprise one or more lipids. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

a. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moeity, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Vitamin D is another example of a sterol, and is involved in calcium absorption from the intestine.

Cholesterol is another example of a steroid, and generally serves structural rather than regulatory functions. In certain embodiments, is preferred that cholesterol and/or its derivatives comprises a nucleic acid delivery composition. It is contemplated that cholesterol and/or its derivatives may enhance vector mediated nucleic acid delivery, stability and/or decrease interaction with blood or lymph components, particularly in embodiments wherein the composition is administered to animal.

A terpene is a lipid comprising one or more five carbon isoprene groups. Terpenes have various biological functions, and include, for example, vitamin A, coenyzme Q and carotenoids (e.g., lycopene and β-carotene).

b. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

c. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

d. Lipid Composition Structures

In a preferred embodiment of the invention, a nucleic acid delivery composition may be associated with a lipid. A nucleic acid delivery composition associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid associated composition of the present invention is not limited to any particular structure. For example, the lipids may also simply be interspersed in a solution, possibly forming aggregates which are not uniform in either size or shape. In another example, the lipids may be present in a bilayer structure, as micelles, or with a "collapsed" structure. In another non-limiting example, a lipofectamine(Gibco BRL)-nucleic acid delivery composition or Superfect (Qiagen)-nucleic acid delivery composition complex is also contemplated.

In certain embodiments, a lipid component of a nucleic acid delivery composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type. In a non-limiting example, a lipid component of a nucleic acid delivery composition may comprise about 10% to about 20% neutral lipids, and about 33% to about 34% of a cerebroside, and about 1% cholesterol. In another non-limiting example, a liposome component of a nucleic acid delivery composition may comprise about 4% to about 12% terpenes, wherein about 1% of the micelle is specifically lycopene, leaving about 3% to about 11% of the liposome as comprising other terpenes; and about 10%to about 35% phosphatidyl choline, and about 1% of a drug. Thus, it is contemplated that lipid components of a nucleic acid delivery composition of the present invention may comprise any of the lipids, lipid types or other components in any combination or percentage range.

i. Emulsions

A nucleic acid delivery composition may be comprised in an emulsion. A lipid emulsion is a substantially permanent heterogeneous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

ii. Micelles

A nucleic acid delivery composition may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

iii. Liposomes

In a further embodiment, a nucleic acid delivery composition of the present invention may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1.

In certain embodiments, a delivery vehicle may comprise a liposome that comprises a targeting agent. In other embodiments, a nucleic acid delivery vehicle component of a may comprise a targeting agent (e.g., a specific binding ligand) in combination with a liposome. The nucleic acid(s) to be delivered are housed within the liposome and the targeting agent is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, a targeting agent of a nucleic acid delivery composition may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

B. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

The present invention utilizes, in one aspect, a DNA purification protocol based on a variation of the alkaline lysis procedure disclosed by Sambrook et al., (1989), modified to include a 2 hour proteinase K digestion step immediately after RNase A digestion (Smyth Templeton et al., 1997).

It is contemplated that one or more steps of this protocol may be combined with other nucleic acid purification techniques to improve the purity and/or quality of the nucleic acids, thereby making them more suitable for use in the nucleic acid delivery compositions and methods of the present invention. In a non-limiting example, it is contemplated that the Terrific Broth growth step increases the yield of DNA. It is contemplated that the lithium chloride precipitation step removes undesired RNA. It is also contemplated that the RNAse step also removes undesired RNA. It is contemplated that the proteinase K step removes undesired proteins, polypeptides and peptides. It is also contemplated that one or more steps may be removed from this protocol, or other protocols, and nucleic acids suitable for use in the nucleic acid delivery compositions and methods of the present invention. Additionally, certain steps used in other protocols are less preferred in the nucleic acid purification methods of the present invention. For example, it is contemplated that the lack of a column binding step may enhance DNA yield by not binding the DNA to a solid substrate. It is contemplated that a lack of a column binding step may enhance DNA quality or suitability in the methods and compositions of the present invention, possibly by not altering DNA conformation upon binding a column. It is contemplated that not using an endotoxin removal step may not detrimentally affect the suitability of the DNA produced for the methods and compositions of the present invention. An endotoxin removal step may be needed if DNA is always contaminated with endotoxin. Of course, one of skill in the art will understand that like materials may be substituted in the methods and compositions of the present invention and like results may be obtained, and are thus encompassed by the present invention. In a non-limiting example, it is contemplate that in addition to or as a substitute for proteinase K, other proteases or protease digestion steps may be used. In another non-limiting example, it is contemplated that other RNA removing steps and/or RNAses may similarly be used and/or substituted. The specific protocol is described below.

Using freshly transformed of host cell bacteria (e.g., DHα5, HB101), a single colony is grown in 7 ml of media (e.g., Terrific Broth+antibiotic) for six hours. Terrific Broth (GIBCO BRL, #22711–022) is prepared by adding 47.0 gms in 1000 ml distilled $H_2O$, adding 4 ml/R glycerol and autoclaving the solution.

Taking 7 ml of the culture above in a tube, the tube is vortexed and 1 ml is used to inoculate 200 ml of Terrific Broth+antibiotic. This culture is grown overnight. The culture is then centrifuged in bottles at 5000 rpm for 10 min at 4° C. or room temperature.

The pellet is gently resuspended in 10 ml of Solution 3 (50 mM dextrose, 25 mM Tris-HCl pH 8, 10 mM EDTA pH 8, in sterile endotoxin-free $H_2O$, stored 4° C.). Add 20 ml of freshly prepared Solution 4 at room temperature (Solution 4=0.2 NaOH, 1% SDS). Gently roll bottles on ice until mixed and the solution turns translucent (approximately 15 to 45 min). Let solution sit at room temperature for 5 minutes.

One then adds 10 ml of Solution 5 (600 ml of 5M potassium acetate, 115.2 ml glacial acetic acid, diluted to 1000 ml with sterile, endotoxin-free $H_2O$. Gently swirl the solution by hand on ice and store on ice for 10 min until a white precipitate appears. Centrifuge at 8000 rpm for 15 at 4° C. Transfer supernatant to a centrifuge bottle. If precipitates are present, transfer using gauze or miracloth on a funnel.

Optional—for endotoxin removal—Cool the supernatant on ice for 15 minutes, add 6 milliliters of cold endotoxin remover (Sigma product no. E4274). Incubate on ice and mix by inversion every two minutes until a clear homogenous solution is obtained (approximately 10 minutes). Incubate solution at 37° C. until phases separate (20–30 minutes). Centrifuge the solution at 4000 rpm for 5 minutes at room temperature. Transfer the upper phase (aqueous phase) to a centrifuge tube/bottle. The lower phase looks like a loose pellet. Proceed with next step.

Next, add 25 ml of room temperature isopropanol, mix well and let sit at room temperature for at least 10 min. Then, the bottle is centrifuged at 5000 rpm for 10 min. The supernatant is aspirated, and the pellet is dissolved in 3 ml of 10 mM Tri-HCl pH 8, dissolved by swirling, and transferred to 500 ml centrifuge tubes. An equal volume (about 3 ml) cold 5 M LiCl (dissolve 42.39 g of LiCl in 150 ml, sterile, endotoxin-free $H_2O$, then add 200 ml more sterile, endotoxin-free $H_2O$ and store at –20° C.) is added, followed by mixing by hand. The tubes are centrifuged at 8000 rpm for 10 min at room temperature.

Transfer the supernatant to a fresh 500 ml centrifuge tube, add an equal volume (about 6 ml) isopropanol, mix well by hand and centrifuge at 5000 rpm for 10 min at room temperature. Aspirate the supernatant, air-dry the pellets for 15 min, and dissolve in 500 $\mu$l of 10 mM Tris-HCl pH 8. Transfer to eppendorf tubes. Ten to 15 $\mu$l of pancreatic RNase A (60 mg/ml stock, stored at –20° C.) is added and incubated at 37° C. for 1 hr. Next, proteinase K is added and incubated at 56° C. for 1 hr (For 515 $\mu$l of sample plus RNase A, add 60 $\mu$l of 1% SDS and 30 $\mu$l of stock proteinase K, to a final concentration of 100 $\mu$g/ml proteinase K/0.1% SDS).

Following incubations, 2×phenol chloroform extraction are performed. For phenol extraction add 600 $\mu$l phenol, vortex 30 sec, spin 13K rpm in microfuge at RT for 3 min, remove top layer and repeat; for chloroform extractions using Tris-saturated chloroform add 600 $\mu$l, vortex for 1 min, spin at 13K rpm in microfuge at RT for 2 min, remove top layer and repeat). Add 3 M sodium acetate, pH 5.2 (adjusted with glacial acetic acid) to produce 0.3 M final concentration (add about 50 μl of 3M sodium acetate). Add two volumes of about 1 ml of ice cold 100% EtOH (stored at −20° C.), mix by inversion and chill at −20° C. for 1 hr or overnight.

Centrifuge the DNA at 13K rpm for 10 min at room temperature in microfuge. Aspriate supernatant and wash the pellet twice with 500 μl of 70% EtOH (stored at 4° C.). Centrifuge at 13K rpm for 5 min at room temperature in microfuge and aspirate the EtOH, then repeat. Let the pellet air dry for 30 minutes to 3 hr; do not use speed vacuum. Dissolve pellet in 250 μl of 10 mM Tris-HCl pH 8. The final concentration of DNA must be about 10 mg/ml.

C. Combining Polycations and Nucleic Acids

It is a surprising discovery of the present invention that combining a liquid medium comprising a polycation and a solution comprising a nucleic acid, wherein ratio of liquid medium volume to solution is greater than about 1.4:1 produces nucleic acid delivery compositions with superior transduction efficiencies.

In certain embodiments, it is contemplated that as long as either one of the polycation or nucleic acid is of a different concentration than the other (either higher concentration or lower concentration), desirable compositions may be produced by an adaptation of the methods described herein. A higher concentration of polycation being combined with a lower concentration of nucleic acid are particularly preferred. In other embodiments, it is contemplated that a lower concentration of polycation may be combined with a higher concentration of nucleic acid.

Thus, for example, a liquid medium comprising a high concentration of polycation in a relatively small volume may be combined with a lower concentration of nucleic acids in a larger volume. In another non-limiting example, a higher concentration of nucleic acids in a smaller volume may be combined with a lower concentration of polycation in a large volume. In another non-limiting example, a lower concentration of nucleic acids in a larger volume may be combined with a higher concentration of polycation in a smaller volume. In a further non-limiting example, a lower concentration of a polycation in a larger volume may be combined to a higher concentration of nucleic acid in a smaller volume.

Thus, in certain embodiments of the present invention, a ratio of concentrations of a polycation or a nucleic acid combined with the other may be about 1:1, about 1.1:1, about 1.2:1, about 1.3:1, about 1.4:1, about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, about 3.5:1, about 3.6:1, about 3.7:1, about 3.8:1, about 3.9:1, about 4.0:1, about 4.1:1, about 4.2:1, about 4.3:1, about 4.4:1, about 4.5:1, about 4.6:1, about 4.7:1, about 4.8:1, about 4.9:1, about 5.0:1, about 5.1:1, about 5.2:1, about 5.3:1, about 5.4:1, about 5.5:1, about 5.6:1, about 5.7:1, about 5.8:1, about 5.9:1, about 6.0:1, about 6.1:1, about 6.2:1, about 6.3:1, about 6.4:1, about 6.5:1, about 6.6:1, about 6.7:1, about 6.8:1, about 6.9:1, about 7.0:1, about 7.1:1, about 7.2:1, about 7.3:1, about 7.4:1, about 7.5:1, about 7.6:1, about 7.7:1, about 7.8:1, about 7.9:1, about 8.0:1, about 8.1:1, about 8.2:1, about 8.3:1, about 8.4:1, about 8.5:1, about 8.6:1, about 8.7:1, about 8.8:1, about 8.9:1, about 9.0:1, about 9.1:1, about 9.2:1, about 9.3:1, about 9.4:1, about 9.5:1, about 9.6:1, about 9.7:1, about 9.8:1, about 9.9:1, about 10.0:1, about 10.1:1, about 10.2:1, about 10.3:1, about 10.4:1, about 10.5:1, about 10.6:1, about 10.7:1, about 10.8:1, about 10.9:1, about 11.0:1, about 11.1:1, about 11.2:1, about 11.3:1, about 11.4:1, about 11.5:1, about 11.6:1, about 11.:1, about 11.8:1, about 11.9:1, about 12.0:1, about 12.2:1, about 12.3:1, about 12.4:1, about 12.5:1, about 12.6:1, about 12.7:1, about 12.8:1, about 12.9:1, about 13.0:1, about 13.1:1, about 13.2:1, about 13.3:1, about 13.4:1, about 13.5:1, about 13.6:1, about 13.7:1, about 13.8:1, about 13.9:1, about 14.0:1, about 14.1:1, about 14.2:1, about 14.3:1, about 14.4:1, about 14.5:1, about 14.6:1, about 14.7:1, about 14.8:1, about 14.9:1, about 15.0:1, about 15.1:1, about 15.2:1, about 15.3:1, about 15.4:1, about 15.5:1, about 15.6:1, about 15.7:1, about 15.8:1, about 15.9:1, about 16.0:1, about 16.1:1, about 16.2:1, about 16.3:1, about 16.4:1, about 16.5:1, about 16.6:1, about 16.7:1, about 16.8:1, about 16.9:1, about 17.0:1, about 17.1:1, about 17.2:1, about 17.3:1, about 17.4:1, about 17.5:1, about 17.6:1, about 17.7:1, about 17.8:1, about 17.9:1, about 18.0:1, about 18.1:1, about 18.2:1, about 18.3:1, about 18.4:1, about 18.5:1, about 18.6:1, about 18.7:1, about 18.8:1, about 18.9:1, about 19.0:1, about 19.1:1, about 19.2:1, about 19.3:1, about 19.4:1, about 19.5:1, about 19.6:1, about 19.7:1, about 19.8:1, about 19.9:1, about 20.0:1, about 50:1, about 100:1, about 500:1, about 1,000:1, about 5,000:1, about 10,000:1, about 100,000:1, about 1,000,000:1 or greater, and any integer derivable therein, and any range derivable therein. In a non-limiting example of such a derivable range, the concentration of polycation to a nucleic acid may be less than about 6.0:1. In a non-limiting example of such a derivable range, the concentration of polycation to a nucleic acid may be less than about 1:6.0. In another non-limiting example of such a derivable range, the concentration of polycation to a nucleic acid may be less than about 1.4:1 to about 6.0:1. In another non-limiting example of such a derivable range, the concentration of polycation to a nucleic acid may be less than about 1.4:1 to about 5.0:1. In another non-limiting example of such a derivable range, the concentration of polycation to a nucleic acid may be less than about 4.0:1. In another non-limiting example of such a derivable range, the concentration of polycation to a nucleic acid may be less than about 1.4:1 to about 3.5:1. In another non-limiting example of such a derivable range, the concentration of polycation to a nucleic acid may be less than about 1.4:1 to about 3.0:1. In another non-limiting example of such a derivable range, the concentration of polycation to a nucleic acid may be less than about 2:1 to about 3.0:1. In another non-limiting example of such a derivable range, the concentration of polycation to a nucleic acid may be less than about 5.0:1. In another non-limiting example of such a derivable range, the concentration of polycation to a nucleic acid may be less than about 4.0:1. In another non-limiting example of such a derivable range, the concentration of polycation to a nucleic acid may be less than about 3.5:1. In another non-limiting example of such a derivable range, the concentration of polycation to a nucleic acid may be less than about 3.0:1.

In other embodiments, it is contemplated that either one or more nucleic acid delivery composition components (e.g., a polycation, a nucleic acid, etc.) may be prepared as in a dry or substantially non-liquid form and added to a liquid medium or solution comprising one or more other components of a nucleic acid delivery composition. For example, in a non-limiting example, a dry or substantially non-liquid form of a nucleic acid delivery composition is added. In a specific non-limiting example, a dry or substantially non-liquid form of a polycation is added. In another particular non-limiting example, a dry or substantially non-liquid form of a nucleic acid is added. In one non-limiting example, a dry or substantially non-liquid form of a polycation and a nucleic acid is added. In other embodiments, a dry or substantially non-liquid form of a nucleic acid delivery composition is reconstituted into a liquid medium, then added.

Thus, in certain embodiments of the present invention, a ratio of volumes of a liquid composition (e.g., solution, emulsion, suspension, etc.) comprising either one of a polycation or a nucleic acid combined with another liquid medium comprising the other component may be about 1.4:1, about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, about 3.5:1, about 3.6:1, about 3.7:1, about 3.8:1, about 3.9:1, about 4.0:1, about 4.1:1, about 4.2:1, about 4.3:1, about 4.4:1, about 4.5:1, about 4.6:1, about 4.7:1, about 4.8:1, about 4.9:1, about 5.0:1, about 5.1:1, about 5.2:1, about 5.3:1, about 5.4:1, about 5.5:1, about 5.6:1, about 5.7:1, about 5.8:1, about 5.9:1, about 6.0:1, about 6.1:1, about 6.2:1, about 6.3:1, about 6.4:1, about 6.5:1, about 6.6:1, about 6.7:1, about 6.8:1, about 6.9:1, about 7.0:1, about 7.1:1, about 7.2:1, about 7.3:1, about 7.4:1, about 7.5:1, about 7.6:1, about 7.7:1, about 7.8:1, about 7.9:1, about 8.0:1, about 8.1:1, about 8.2:1, about 8.3:1, about 8.4:1, about 8.5:1, about 8.6:1, about 8.7:1, about 8.8:1, about 8.9:1, about 9.0:1, about 9.1:1, about 9.2:1, about 9.3:1, about 9.4:1, about 9.5:1, about 9.6:1, about 9.7:1, about 9.8:1, about 9.9:1, about 10.0:1, about 10.1:1, about 10.2:1, about 10:3:1, about 10.4:1, about 10.5:1, about 10.6:1, about 10.7:1, about 10.8:1, about 10.9:1, about 11.0:1, about 11.1:1, about 11.2:1, about 11.3:1, about 11.4:1, about 11.5:1, about 11.6:1, about 11.:1, about 11.8:1, about 11.9:1, about 12.0:1, about 12.2:1, about 12.3:1, about 12.4:1, about 12.5:1, about 12.6:1, about 12.7:1, about 12.8:1, about 12.9:1, about 13.0:1, about 13.1:1, about 13.2:1, about 13.3:1, about 13.4:1, about 13.5:1, about 13.6:1, about 13.7:1, about 13.8:1, about 13.9:1, about 14.0:1, about 14.1:1, about 14.2:1, about 14.3:1, about 14.4:1, about 14.5:1, about 14.6:1, about 14.7:1, about 14.8:1, about 14.9:1, about 15.0:1, about 15.1:1, about 15.2:1, about 15.3:1, about 15.4:1, about 15.5:1, about 15.6:1, about 15.7:1, about 15.8:1, about 15.9:1, about 16.0:1, about 16.1:1, about 16.2:1, about 16.3:1, about 16.4:1, about 16.5:1, about 16.6:1, about 16.7:1, about 16.8:1, about 16.9:1, about 17.0:1, about 17.1:1, about 17.2:1, about 17.3:1, about 17.4:1, about 17.5:1, about 17.6:1, about 17.7:1, about 17.8:1, about 17.9:1, about 18.0:1, about 18.1:1, about 18.2:1, about 18.3:1, about 18.4:1, about 18.5:1, about 18.6:1, about 18.7:1, about 18.8:1, about 18.9:1, about 19.0:1, about 19.1:1, about 19.2:1, about 19.3:1, about 19.4:1, about 19.5:1, about 19.6:1, about 19.7:1, about 19.8:1, about 19.9:1, about 20.0:1, about 50:1, about 100:1, about 500:1, about 1,000:1, about 5,000:1, about 10,000:1, about 100,000:1, about 1,000,000:1 or greater, and any integer derivable therein, and any range derivable therein. In a non-limiting example of such a derivable range, the volume of liquid medium comprising polycation to liquid medium comprising a nucleic acid may be less than about 6.0:1. In a non-limiting example of such a derivable range, the volume of liquid medium comprising polycation to liquid medium comprising a nucleic acid may be less than about 1:6.0. In another non-limiting example, the volume of liquid medium comprising polycation to solution comprising a nucleic acid may be between about 1.4:1 to about 6.0:1. In another non-limiting example, the volume of liquid medium comprising polycation to solution comprising a nucleic acid may be between about 1.4:1 to about 5.0:1. In another non-limiting example, the volume of liquid medium comprising polycation to solution comprising a nucleic acid may be between about 1.4:1 to about 4.0:1. In another non-limiting example, the volume of liquid medium comprising polycation to solution comprising a nucleic acid may be between about 1.4:1 to about 3.5:1. In another non-limiting example, the volume of liquid medium comprising polycation to solution comprising a nucleic acid may be between about 1.4:1 to about 3.0:1. In another non-limiting example, the volume of liquid medium comprising polycation to solution comprising a nucleic acid may be between about 2:1 to about 3.0:1. In another non-limiting example, the volume of liquid medium comprising polycation to solution comprising a nucleic acid may be less than about 5.0:1. In another non-limiting example, the volume of liquid medium comprising polycation to solution comprising a nucleic acid may be less than about 4.0:1. In another non-limiting example, the volume of liquid medium comprising polycation to solution comprising a nucleic acid may be less than about 3.5:1. In another non-limiting example, the volume of liquid medium comprising polycation to solution comprising a nucleic acid may be less than about 3.0:1.

In other embodiments of the present invention, a ratio of cationic moeities or residues of the polycation(s) combined with anionic moeities of the nucleic acid(s), or visa verce is about 1:1, about 1.1:, about 1.2:1, about 1.3:1, about 1.4:1, about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, about 3.0:1, about 3.1:1, about 3.2:1, about 3.3:1, about 3.4:1, about 3.5:1, about 3.6:1, about 3.7:1, about 3.8:1, about 3.9:1, about 4.0:1, about 4.1:1, about 4.2:1, about 4.3:1, about 4.4:1, about 4.5:1, about 4.6:1, about 4.7:1, about 4.8:1, about 4.9:1, about 5.0:1, about 5.1:1, about 5.2:1, about 5.3:1, about 5.4:1, about 5.5:1, about 5.6:1, about 5.7:1, about 5.8:1, about 5.9:1, about 6.0:1, about 6.1:1, about 6.2:1, about 6.3:1, about 6.4:1, about 6.5:1, about 6.6:1, about 6.7:1, about 6.8:1, about 6.9:1, about 7.0:1, about 7.1:1, about 7.2:1, about 7.3:1, about 7.4:1, about 7.5:1, about 7.6:1, about 7.7:1, about 7.8:1, about 7.9:1, about 8.0:1, about 8.1:1, about 8.2:1, about 8.3:1, about 8.4:1, about 8.5:1, about 8.6:1, about 8.7:1, about 8.8:1, about 8.9:1, about 9.0:1, about 9.1:1, about 9.2:1, about 9.3:1, about 9.4:1, about 9.5:1, about 9.6:1, about 9.7:1, about 9.8:1, about 9.9:1, about 10.0:1, about 10.1:1, about 10.2:1, about 10:3:1, about 10.4:1, about 10.5:1, about 10.6:1, about 10.7:1, about 10.8:1, about 10.9:1, about 11.0:1, about 11.1:1, about 11.2:1, about 11.3:1, about 11.4:1, about 11.5:1, about 11.6:1, about 11.:1, about 11.8:1, about 11.9:1, about 12.0:1, about 12.2:1, about 12.3:1, about 12.4:1, about 12.5:1, about 12.6:1, about 12.7:1, about 12.8:1, about 12.9:1, about 13.0:1, about 13.1:1, about 13.2:1, about 13.3:1, about 13.4:1, about 13.5:1, about 13.6:1, about 13.7:1, about 13.8:1, about 13.9:1, about 14.0:1, about 14.1:1, about 14.2:1, about 14.3:1, about 14.4:1, about 14.5:1, about 14.6:1, about 14.7:1, about 14.8:1, about 14.9:1, about 15.0:1, about 15.1:1, about 15.2:1, about 15.3:1, about 15.4:1, about 15.5:1, about 15.6:1, about 15.7:1, about 15.8:1, about 15.9:1, about 16.0:1, about 16.1:1, about 16.2:1, about 16.3:1, about 16.4:1, about 16.5:1, about 16.6:1, about 16.7:1, about 16.8:1, about 16.9:1, about 17.0:1, about 17.1:1, about 17.2:1, about 17.3:1, about 17.4:1, about 17.5:1, about 17.6:1, about 17.7:1, about 17.8:1, about 17.9:1, about 18.0:1, about 18.1:1, about 18.2:1, about 18.3:1, about 18.4:1, about 18.5:1, about 18.6:1, about 18.7:1, about 18.8:1, about 18.9:1, about 19.0:1, about 19.1:1, about 19.2:1, about 19.3:1, about 19.4:1, about 19.5:1, about 19.6:1, about 19.7:1, about 19.8:1, about 19.9:1, about 20.0:1, about 50:1, about 100:1, about 500:1, about 1,000:1, about 5,000:1, about 10,000:1, about 100,000:1, about 1,000,000:1 or greater, and any integer derivable therein, and any range derivable therein. In a non-limiting example of a range of cationic moeities to anionic moeities, the number of cationic moeities to anionic moeities may be less than about 6.0:1. In another non-limiting example, the number of cationic moeities to anionic moeities may be less than about 1.4:1 to about 6.0:1. In another non-limiting example, the number of cationic moeities to anionic moeities may be less than about 1.4:1 to about 5.0:1. In another non-limiting example, the number of cationic moeities to anionic moeities may be less than about 1.4:1 to about 4.0:1. In another non-limiting example, the number of cationic moeities to anionic moeities may be less than about 1.4:1 to about 3.5:1. In another non-limiting example, the number of cationic moeities to anionic moeities may be less than about 1.4:1 to about 3.0:1. In another non-limiting example, the number of cationic moeities to anionic moeities may be less than about 2:1 to about 3.0:1. In another non-limiting example, the number of cationic moeities to anionic moeities may be less than about 5.0:1. In another non-limiting example, the number of cationic moeities to anionic moeities may be less than about 4.0:1. In another non-limiting example, the number of cationic moeities to anionic moeities may be less than about 3.5:1. In another non-limiting example, the number of cationic moeities to anionic moeities may be less than about 3.0:1. In a further non-limiting example, the number of cationic to anionic moeities are about 2.4:1 to about 2.7:1. In an additional non-limiting example, the number of cationic moeities to anionic moeities is from about 1.5:1 to about 6:1.

The compositions comprising the polycation(s) and nucleic acid(s) may be combined by any method described herein or as would be known to one of ordinary skill in the art. For example, the composition comprising a polycation may be added to a composition comprising a nucleic acid, composition comprising a nucleic acid may be added to a composition comprising a polycation, and/or both compositions may be added to each other. Other non-limiting examples of adding various nucleic acid delivery composition components are described herein.

D. Nucleic Acid Compositions

Certain embodiments of the present invention concern a purified nucleic acid. In certain aspects, a purified nucleic acid comprises a wild-type or a mutant nucleic acid. In particular aspects, a nucleic acid encodes for or comprises a transcribed nucleic acid. In particular aspects, a nucleic acid encodes a protein, polypeptide, peptide.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. A table non-limiting, purine and pyrimidine derivatives and analogs is also provided herein below.

TABLE 1

Purine and Pyrmidine Derivatives or Analogs

| Abbr. | Modified base description | Abbr. | Modified base description |
|---|---|---|---|
| Ac4c | 4-acetylcytidine | Mam5s2u | 5-methoxyaminomethyl-2-thiouridine |
| Chm5u | 5-(carboxyhydroxylmethyl)uridine | Man q | Beta,D-mannosylqueosine |

TABLE 1-continued

Purine and Pyrmidine Derivatives or Analogs

| Abbr. | Modified base description | Abbr. | Modified base description |
|---|---|---|---|
| Cm | 2'-O-methylcytidine | Mcm5s2u | 5-methoxycarbonylmethyl-2-thiouridine |
| Cmnm5s2u | 5-carboxymethylaminomethyl-2-thioridine | Mcm5u | 5-methoxycarbonylmethyluridine |
| Cmnm5u | 5-carboxymethylaminomethyluridine | Mo5u | 5-methoxyuridine |
| D | Dihydrouridine | Ms2i6a | 2-methylthio-N6-isopentenyladenosine |
| Fm | 2'-O-methylpseudouridine | Ms2t6a | N-((9-beta-D-ribofuranosyl-2-methylthiopurine-6-yl)carbamoyl)threonine |
| Gal q | Beta,D-galactosylqueosine | Mt6a | N-((9-beta-D-ribofuranosylpurine-6-yl)N-methyl-carbamoyl)threonine |
| Gm | 2'-O-methylguanosine | Mv | Uridine-5-oxyacetic acid methylester |
| I | Inosine | o5u | Uridine-5-oxyacetic acid (v) |
| I6a | N6-isopentenyladenosine | Osyw | Wybutoxosine |
| m1a | 1-methyladenosine | P | Pseudouridine |
| m1f | 1-methyipseudouridine | Q | Queosine |
| m1g | 1-methylguanosine | s2c | 2-thiocytidine |
| m1I | 1-methylinosine | s2t | 5-methyl-2-thiouridine |
| m22g | 2,2-dimethylguanosine | s2u | 2-thiouridine |
| m2a | 2-methyladenosine | s4u | 4-thiouridine |
| m2g | 2-methylguanosine | T | 5-methyluridine |
| m3c | 3-methylcytidine | t6a | N-((9-beta-D-ribofuranosylpurine-6-yl)carbamoyl)threonine |
| m5c | 5-methylcytidine | Tm | 2'-O-methyl-5-methyluridine |
| m6a | N6-methyladenosine | Um | 2'-O-methyluridine |
| m7g | 7-methylguanosine | Yw | Wybutosine |
| Mam5u | 5-methylaminomethyluridine | X | 3-(3-amino-3-carboxypropyl)uridine, (acp3)u |

A nucleobase may be comprised in a nucleside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moeity. A non-limiting example of a "nucleobase linker moeity" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moeity are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moeity". A backbone moeity generally covalently attaches a nucleotide to another molecule comprising a nucleotide, or to another nucleotide to form a nucleic acid. The "backbone moeity" in naturally occurring nucleotides typically comprises a phosphorus moeity, which is covalently attached to a 5-carbon sugar. The attachment of the backbone moeity typically occurs at either the 3'- or 5'-position of the 5-carbon sugar. However, other types of attachments are known in the art, particularly when a nucleotide comprises derivatives or analogs of a naturally occurring 5-carbon sugar or phosphorus moeity.

4. Nucleic Acid Analogs

A nucleic acid may comprise, or be composed entirely of, a derivative or analog of a nucleobase, a nucleobase linker moeity and/or backbone moeity that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moeity, but possesses similar functions. As used herein, a "moeity" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

A non-limiting example of a nucleic acid analog is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moeity, a nucleobase linker moeity that is not a 5-carbon sugar, and/or a backbone moeity that is not a phosphate backbone moeity. Examples of nucleobase linker moeities described for PNAs include aza nitrogen atoms, amido and/or ureido tethers (see for example, U.S. Pat. No. 5,539,082). Examples of backbone moeities described for PNAs include an aminoethylglycine, polyamide, polyethyl, polythioamide, polysulfinamide or polysulfonamide backbone moeity.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed by the invention. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. Examples of this is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

5. Preparation of Nucleic Acids

A nucleic acid may be made by any technique known to one of ordinary skill in the art, such as for example, chemical synthesis or recombinant production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 1989, incorporated herein by reference).

E. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment.

Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 2 lists non-limiting examples of elements/promoters that may be employed, in the context of the present invention, to regulate the expression of a RNA. Table 3 provides non-limiting examples of inducible elements, which are regions of a nucleic acid sequence that can be activated in response to a specific stimulus.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985;Atchinson et al., 1986, 1987; Imler et al., 1987;Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al.,1986; Herr et al., 1986; |

TABLE 2-continued

Promoter and/or Enhancer

| Promoter/Enhancer | References |
| --- | --- |
| Polyoma | Imbra et al., 1986; Kadesch et al., 1986; Wang et al., 1986; Ondek et al.,1987; Kuhl et al., 1987; Schaffner et al., 1988 Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al.,1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple nucleic acids can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor-mediated endocytosis, and to integrate into host cell genome and express viral genes stably and efficiently have made them candidates for the transfer of foreign nucleic acids into cells (e.g., mammalian cells). Vector components of the present invention may be a viral vector that encode one or more transcribed nucleic acids. Non-limiting examples of virus vectors that may be used in the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of nucleic acid transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the nucleic acid delivery compositions of the present invention as it has a high frequency of integration and it can infect nondividing cells, thus making it useful for delivery of nucleic acids into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have promise as nucleic acid delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted (e.g., ligated) into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for nucleic acid transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo nucleic acid transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another nucleic acid which encodes the ligand for a receptor on a specific target cell, for example, the vector is now target-specific.

d. Other Viral Vectors

Other viral vectors may be employed as vector constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moeities may be used to specifically transfect APC types.

F. Nucleic Acid Delivery and Cell Transformation

Suitable methods for contacting a nucleic acid delivery composition with a cell, for transformation of an organelle, a cell, a tissue or an organism, for use with the current invention are believed to include virtually any method by which a nucleic acid (e.g., DNA) can be introduced into an organelle, a cell, a tissue or an organism, as described herein or as would be known to one of ordinary skill in the art. Such methods can be adapted to use nucleic acid delivery compositions of the present invention to substitute for other nucleic acid compositions previously used in such methods.

G. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous nucleic acid encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org).

1. Tissues

A tissue may comprise a host cell or cells to be transformed or contacted with a nucleic acid delivery composition and/or and additional agent. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

2. Organisms

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

a. Eubacteria

In certain embodiments, the organism is an eubacteria. In particular embodiments, the eubacteria may be, but is not limited to, an aquificales; a thermotogales; a thermodesulfobacterium; a member of the thermus-deinococcus group; a chloroflecales; a cyanobacteria; a firmicutes; a member of the leptospirillum group; a synergistes; a member of the chlorobium-flavobacteria group; a member of the chlamydia-verrucomicrobia group, including but not limited to a verrucomicrobia or a chlamydia; a planctomycetales; a flexistipes; a member of the fibrobacter group; a spirochetes; a proteobacteria, including but not limited to an alpha proteobacteria, a beta proteobacteria, a delta & epsilon proteobacteria or a gamma proteobacteria. In certain aspects, an organelle derived from eubacteria are contemplated, including a mitochondria or a chloroplast.

b. Archaea

In certain embodiments, the organism is an archaea (a.k.a. archaebacteria; e.g., a methanogens, a halophiles, a sulfolobus). In particular embodiments, the archaea may be, but is not limited to, a korarchaeota; a crenarchaeota, including but not limited to, a thermofilum, a pyrobaculum, a thermoproteus, a sulfolobus, a metallosphaera, an acidianus, a thermodiscus, a igneococcus, a thermosphaera, a desulfurococcus, a staphylothermus, a pyrolobus, a hyperthermus or a pyrodictium; or an euryarchaeota, including but not limited to a halobacteriales, methanomicrobiales, a methanobacteriales, a methanococcales, a methanopyrales, an archeoglobales, a thermoplasmales or a thermococcales.

c. Eukaryotes

In certain embodiments, the organism is an eukaryote (e.g., a protist, a plant, a fungi, an animal). In particular embodiments, the eukaryote may be, but is not limited to, a microsporidia, a diplomonad, an oxymonad, a retortamonad, a parabasalid, a pelobiont, an entamoebae or a mitochondrial eukaryote (e.g., an animal, a plant, a fungi, a stramenopiles).

In certain embodiments, the mitochondrial eukaryote may be, but is not limited to, a metazoa (e.g., an animal), a myxozoa, a choanoflagellate, a fungi (e.g., a mushroom, a mold, a yeast, a chytrid), a green plant (e.g., a green algae, a land plant), a cryptomonad, an ancyromona, plasmodiophorid, a rhodophyta, a centrohelid heliozoa, a cyanophorid, an alveolate (e.g., a dinoflagellate, a sporozoan, a ciliate), a stramenopile (e.g., a brown algae, a diatoms, an oomycete, a chrysophyte), an acantharea, a vampyrellid, a thaumatomonad, a telonema, a sticholonche, a spongomonad, a ramicristate, a pseudospora, a pseudodendromonad, a phalansterium, a phaeodarean radiolaria, a paramyxea, a luffisphaera, a leucodictyon, a kathablepharid, a histiona, a haptophyte, an ebriid, a discocelis, a diphylleia, a eesmothoracid, a cryothecomona, a copromyxid, a chlorarachnion, a cercomonad, a caecitellus, an apusomonad, an actinophryid or an acanthamoebae.

In particular aspects, the eukaryote is a metazoa (e.g., an animal). In certain aspects, the metazoa may be, but is not limited to, a porifera (e.g., a sponge), a cnidaria (e.g., a jellyfish, an anemone, a coral), a ctenophora (e.g., a comb-jelly), an arthropoda (e.g., an insect, a spider, a crab), an annelida (e.g., a segmented worm), a pogonophora, a vestimentifera, an echiura, a mollusca (e.g., a snail, a clam, a squid), a sipuncula, a nemertea (e.g., a ribbon worm), a platyhelminthes (e.g., a flatworm), a chordata (e.g., a vertebrate), a hemichordata, a lophophorates, a chaetognatha, an echinodermata (e.g., a starfish, a urchin, a sea cucumber), a pseudocoelomates, a placozoa, a monoblastozoa, rhomobozoa, an orthonectida. In particular facets the vertebrate may be a terrestrial vertebrate (e.g., a frog, a salamander, a caecilian, a reptile, a mammal, a bird) or a non-terrestrial vertebrate (e.g., a sharks, a ray, a sawfish, a chimera, a ray-finned fish, a lobe-finned fish). In additional facets, the mammal may be a monotremata (e.g., a platypus, an echidna), a multituberculata, a marsupialia (e.g., an opossum, a kangaroo), a palaeoryctoids or an eutheria (e.g., a placental mammal).

In particular facets the eutheria may be, but is not limited to, an edentata (e.g., an anteater, a sloth, an armadillo), a pholidota (e.g., a pangolin), a lagomorpha (e.g., a rabbits), a glires, a rodentia (e.g., a mouse, a rat, a squirrel, a gopher, a porcupine, a beaver), a macroscelidea (e.g., an elephant shrew), a primates (e.g., a monkey, a lemur, a gorilla, a chimp, a human), a scandentia (e.g., a tree shrew), a chiroptera (e.g., a bat), a dermoptera (e.g., a colugo, a flying lemur), an insectivora (e.g., a shrew, a mole, a hedgehog), a creodonta, a carnivora (e.g., a dog, a cat, a bear, a raccon, a weasel, a mongoose, a hyena), a condylarthra, an artiodactyla (e.g., a pig, a deer, a cattle, a goat, a sheep, a hippopotamus, a camel), a cetacea (e.g, a whale, a dolphin, a porpoise), a tubulidentata (e.g., an aardvark), a perissodactyla (e.g., a horse, a tapir, a rhinoceros), a hyracoidea (e.g., a hyrax, a dassy), a sirenia (e.g., a manatee, a dugong, a sea cow), a desmostylia, an embrythopoda, or a proboscidea (e.g., an elephant).

In particular embodiments, eukaryote is a fungi. A fungi may be, but is not limited to, a chytridiomycota (e.g., a water mold, an allomyces), a zygomycota (e.g., a bread mold, a rhizopus, a mucor), a basidiomycota (e.g., a mushroom, a rust, a smut) or an ascomycota (e.g., a sac fungi, a yeast, a penicillium).

In certain embodiments, the eukaryote is a green plant. A green plant may be, but is not limited to, a prasinophytes, a chlorophyceae, a trebouxiophyceae, a ulvophyceae, a chlorokybales, a klebsormidiales, a zygnematales, a streptophyta, a charales, a coleochaetales or an embryophytes (e.g., a land plant). In particular facets, the embryophytes may be, but is not limited to, a marchantiomorpha (e.g., a liverwort), an Anthoceromorpha (e.g., a hornwort), a bryopsida (e.g., a moss), a lycopsida (e.g., a lycophyte), an equisetopsida (e.g., a horsetail, a sphenophyte), a filicopsida (e.g., a fern), a spermatopsida (e.g., a seed plant: a flowering plant, a conifer). In particular aspects, the spermatopsida may be, but is not limited to an angiosperm. An angiosperm may include, but is not limited to, a ceratophyllaceae, a nymphaeales, a piperales, an aristolochiales, a monocotyledons, an eudicots, a laurales, a chloranthaceae, a winterales or a magnoliales.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

H. Genetic Therapy Agents

Gene therapy now is becoming a viable alternative to various conventional therapies, especially in the area of cancer treatment. Limitations such as long term expression of transgenes and immuno-destruction of target cells through the expression of vector products, which have been said to limit the implementation of genetic therapies, are not concerns in cancer therapies, where destruction of cancer cells is desired.

A tumor cell resistance to agents, such as chemotherapeutic and radiotherapeutic agents, represents a major problem in clinical oncology. It is important in gene transfer therapies, especially those involving treatment of cancer, to kill as many of the cells as quickly as possible. One goal of current cancer research is to find ways to improve the efficacy of one or more anti-cancer agents by combining such an agent with gene therapy. Thus, the use of "combination" therapies may be favored. Such combinations may include gene therapy and radiotherapy or chemotherapy. For example, Roth et al., (1996) have demonstrated that a combination of DNA damaging agents and p53 gene therapy provides increased killing of tumor cells in vivo. In another example, the herpes simplex-thymidine kinase (HS-tK)

gene, when delivered to brain tumors by a retroviral vector system, successfully induced susceptibility to the antiviral agent ganciclovir (Culver, et al., 1992). In the context of the present invention, it is contemplated that gene therapy could be used similarly in conjunction with the nucleic acid delivery composition and/or other agents.

Yet another type of combination therapy involves the use of multi-gene therapy. In this situation, more than one therapeutic gene would be transferred into a target cell. The genes could be from the same functional group (e.g., both tumor suppressors, both cytokines, etc.) or from different functional groups (e.g., a tumor suppressor and a cytokine). By presenting particular combinations of therapeutic genes to a target cell, it may be possible to augment the overall effect of either or both genes on the physiology of the target cell.

1. Inducers of Cellular Proliferation

In one embodiment of the present invention, it is contemplated that anti-sense mRNA directed to a particular inducer of cellular proliferation is used to prevent expression of the inducer of cellular proliferation. The proteins that induce cellular proliferation further fall into various categories dependent on function. The commonality of all of these proteins is their ability to regulate cellular proliferation. A table listing non-limiting examples of oncogenes that may be targeted by the methods and compositions of the present invention is shown below.

TABLE 4

Oncogenes

| Gene | Source | Human Disease | Function |
|---|---|---|---|
| Growth Factors[1] | | | FGF family member |
| HST/KS | Transfection | | |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases[1,2] | | | |
| ERBB/HER | Avian erythroblastosis Virus; ALV promoter Insertion; amplified Human tumors | Amplified, deleted Squamous cell Cancer; glioblastoma | EGF/TGF-α/ amphiregulin/ hetacellulin receptor |
| ERBB-2/NEU/HER-2 | Transfected from rat Glioblatoms | Amplified breast, Ovarian, gastric cancers | Regulated by NDF/ heregulin and EGF- related factors |
| FMS | SM feline sarcoma virus | | CSF-1 receptor |
| KIT | HZ feline sarcoma virus | | MGF/Steel receptor hematopoieis |
| TRK | Transfection from Human colon cancer | | NGF (nerve growth factor) receptor |
| MET | Transfection from Human osteosarcoma | | Scatter factor/HGF receptor |
| RET | Translocations and point mutations | Sporadic thyroid cancer; Familial medullary Thyroid cancer; multiple endocrine neoplasias 2A and 2B | Orphan receptor Tyr kinase |
| ROS | URII avian sarcoma Virus | | Orphan receptor Tyr kinase |
| PDGF receptor | Translocation | Chronic Myclomonocytic Leukemia | TEL(ETS-like transcription factor)/ PDGF receptor gene fusion |
| TGF-βreceptor | | Colon carcinoma Mismatch mutation Target | |
| NONRECEPTOR TYROSINE KINASES[1] | | | |
| ABI. | Abelson Mul.V | Chronic myelogenous Leukemia translocation With BCR | Interact with RB, RNA polymerase, CRK, CBL |

TABLE 4-continued

| Oncogenes | | | |
|---|---|---|---|
| Gene | Source | Human Disease | Function |
| FPS/FES | Avian Fujinami SV;GA FeSV | | |
| LCK | Mul.V (murine leukemia Virus) promoter Insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES[1] | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophilia homology | Nevoid basal cell cancer Syndrome (Gorline Syndrome) | 12 transmembrane domain; signals through Gli homogue CI to antagonize hedgehog pathway |
| TAN-1 Notch homologue | Translocation | T-ALL | Signaling? |
| MISCELLANEOUS SIGNALING[1,3] | | | |
| BCL-2 | Translocation | B-cell lymphoma | Apoptosis |
| CBL | Mu Cas NS-1 V | | Tyrosine-phosphorylated RING finger interact Abl |
| CRK | CT1010 ASV | | Adapted SH2/SH3 interact Abl |
| DPC4 | Tumor suppressor | Pancreatic cancer | TGF-β-related signaling pathway |
| MAS | Transfection and Tumorigenicity | | Possible angiotensin receptor |
| NCK | | | Adaptor SH2/SH3 |
| GUANINE NUCLEOTIDE EXCHANGERS AND BINDING PROTEINS[3,4] | | | |
| BCR | | Translocated with ABL in CML | Exchanger; protein kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |

TABLE 4-continued

Oncogenes

| Gene | Source | Human Disease | Function |
| --- | --- | --- | --- |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS[1,5–9] | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGI /LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX+ ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau Syndrome | Negative regulator or elongin; transcriptional elongation complex |
| WT-1 | | Wilm's tumor | Transcription factor |

TABLE 4-continued

Oncogenes

| Gene | Source | Human Disease | Function |
| --- | --- | --- | --- |
| CELL CYCLE/DNA DAMAGE RESPONSE[10-21] | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition Leukemia | |
| FHIT | Fragile site 3p14.2 | Lung carcinoma | Histidine triad-related diadenosine 5',3'''- $P^1.p^4$ tetraphosphate asymmetric hydrolase |
| HMLI/MutL | | HNPCC | Mismatch repair; MutL homologue |
| HMSH2/MutS | | HNPCC | Mismatch repair; MutS homologue |
| HPMS1 | | HNPCC | Mismatch repair; MutL homologue |
| HPMS2 | | HNPCC | Mismatch repair; MutL homologue |
| INK4/MTS1 | Adjacent INK-4B at 9p21; CDK complexes | Candidate MTS1 Suppressor and MLM Melanoma gene | P16 CDK inhibitor |
| INK4B/MTS2 | | Candidate suppressor | P15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; Osteosarcoma; breast cancer; other sporadic cancers | Interact cyclin/cdk; regulate E2F transcription factor |
| XPA | | Xeroderma Pigmentosum; skin cancer predisposition | Excision repair; photo-product recognition; zinc finger |

For example, a form of PDGF, the sis oncogene, is a secreted growth factor. Oncogenes rarely arise from genes encoding growth factors, and at the present, sis is the only known naturally-occurring oncogenic growth factor.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

Other proteins such as Jun, Fos and Myc are proteins that directly exert their effects on nuclear functions as transcription factors.

2. Inhibitors of Cellular Proliferation

In certain embodiment, the restoration of the activity of an inhibitor of cellular proliferation through a genetic construct is contemplated. Tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Okamoto et al., 1994; Nobori et al., 1995; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf; erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

In certain embodiments, it is contemplated that genetic constructs that stimulate apoptosis will be used to promote the death of diseased or undesired tissue. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

I. Cancer Treatments

In order to increase the effectiveness of a therapeutic nucleic acid delivered to a cell, tissue or organism for the treatment of cancer, it may be desirable to combine the compositions and methods of the present invention with an agent effective in the treatment of hyperproliferative disease, such as, for example, an anti-cancer agent. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

More generally, such an agent would be provided in a combined amount with a therapeutic nucleic acid delivery composition effective to kill or inhibit proliferation of a cancer cell. This process may involve contacting the cell(s) with an agent(s) and the nucleic acid delivery composition at the same time. This may be achieved by contacting the cell, tissue or organism with a single composition or pharmacological formulation that includes both a nucleic acid delivery composition and one or more agents, or by contacting the cell with two or more distinct compositions or formulations, at the same time, wherein one composition includes a nucleic acid delivery composition and the other includes one or more agents.

The terms "contacted" and "exposed," when applied to a cell, tissue or organism, are used herein to describe the process by which a therapeutic nucleic acid delivery composition of the present invention and/or another agent, such as for example a chemotherapeutic or radiotherapeutic agent, are delivered to a target cell, tissue or organism or are placed in direct juxtaposition with the target cell, tissue or organism. To achieve cell killing or stasis, the nucleic acid delivery composition and/or additional agent(s) are delivered to one or more cells in a combined amount effective to kill the cell(s) or prevent them from dividing.

The administration of the nucleic acid delivery composition may precede, be co-current with and/or follow the other agent(s) by intervals ranging from minutes to weeks. In embodiments where the nucleic acid delivery composition and other agent(s) are applied separately to a cell, tissue or organism, one would generally ensure that a significant period of time did not expire between the time of each delivery, such that the nucleic acid delivery composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the nucleic acid delivery composition. In other aspects, one or more agents may be administered within of from about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the nucleic acid delivery composition. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the nucleic acid delivery composition. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combination regimens of the nucleic acid delivery composition and one or more agents may be employed. Non-limiting examples of such combinations are shown below, wherein a nucleic acid delivery composition is "A" and an agent is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | | B/B/A/A | |
| B/A/B/A | B/A/A/B | A/A/A/B | B/A/A/A | A/B/A/A | | A/A/B/A | |

Administration of the nucleic acid delivery composition to a cell, tissue or organism may follow general protocols for the administration of chemotherapeutics, taking into account the toxicity, if any. It is expected that the treatment cycles would be repeated as necessary. In particular embodiments, it is contemplated that various additional agents may be applied in any combination with the present invention.

1. Chemotherapeutic Agents

The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

a. Alkylating Agents

Alkylating agents are drugs that directly interact with genomic DNA to prevent the cancer cell from proliferating.

This category of chemotherapeutic drugs represents agents that affect all phases of the cell cycle, that is, they are not phase-specific. Alkylating agents can be implemented to treat, for example, chronic leukemia, non-Hodgkin's lymphoma, Hodgkin's disease, multiple myeloma, and particular cancers of the breast, lung, and ovary. An alkylating agent, may include, but is not limited to, a nitrogen mustard, an ethylenimene, a methylmelamine, an alkyl sulfonate, a nitrosourea or a triazines.

They include but are not limited to: busulfan, chlorambucil, cisplatin, cyclophosphamide (cytoxan), dacarbazine, ifosfamide, mechlorethamine (mustargen), and melphalan. In specific aspects, troglitazaone can be used to treat cancer in combination with any one or more of these alkylating agents, some of which are discussed below.

i. Nitrogen Mustards

A nitrogen mustard may be, but is not limited to, mechlorethamine ($HN_2$), which is used for Hodgkin's disease and non-Hodgkin's lymphomas; cyclophosphamide and/or ifosfamide, which are used in treating such cancers as acute or chronic lymphocytic leukemias, Hodgkin's disease, non-Hodgkin's lymphomas, multiple myeloma, neuroblastoma, breast, ovary, lung, Wilm's tumor, cervix testis and soft tissue sarcomas; melphalan (L-sarcolysin), which has been used to treat such cancers as multiple myeloma, breast and ovary; and chlorambucil, which has been used to treat diseases such as, for example, chronic lymphatic (lymphocytic) leukemia, malignant lymphomas including lymphosarcoma, giant follicular lymphoma, Hodgkin's disease and non-Hodgkin's lymphomas.

a. Chlorambucil

Chlorambucil (also known as leukeran) is a bifunctional alkylating agent of the nitrogen mustard type that has been found active against selected human neoplastic diseases. Chlorambucil is known chemically as 4-[bis(2-chlorethyl) amino] benzenebutanoic acid.

Chlorambucil is available in tablet form for oral administration. It is rapidly and completely absorbed from the gastrointestinal tract. For example, after a single oral doses of about 0.6 mg/kg to about 1.2 mg/kg, peak plasma chlorambucil levels are reached within one hour and the terminal half-life of the parent drug is estimated at about 1.5 hours. About 0.1 mg/kg/day to about 0.2 mg/kg/day or about 36 mg/m$^2$/day to about 6 mg/m$^2$/day or alternatively about 0.4 mg/kg may be used for antineoplastic treatment. Chlorambucil is not curative by itself but may produce clinically useful palliation.

b. Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [($ClCH_2CH_2)_2N$—$POCl_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable oral doses for adults include, for example, about 1 mg/kg/day to about 5 mg/kg/day (usually in combination), depending upon gastrointestinal tolerance; or about 1 mg/kg/day to about 2 mg/kg/day; intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. In some aspects, a dose of about 250 mg/kg/day may be administered as an antineoplastic. Because of gastrointestinal adverse effects, the intravenous route is preferred for loading. During maintenance, a leukocyte count of about 3000/mm$^3$ to 4000/mm$^3$ usually is desired. The drug also sometimes is administered intramuscularly, by infiltration or into body cavities. It is available in dosage forms for injection of about 100 mg, about 200 mg and about 500 mg, and tablets of about 25 mg and about 50 mg.

c. Melphalan

Melphalan, also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of about 2.1. Melphalan is available in tablet form for oral administration and has been used to treat multiple myeloma. Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of about 0.2 mg/kg daily for five days as a single course. Courses are repeated about every four to five weeks depending upon hematologic tolerance (Smith and Rutledge, 1975; Young et al., 1978). Alternatively in certain embodiments, the dose of melphalan used could be as low as about 0.05 mg/kg/day or as high as about 3 mg/kg/day or greater.

ii Ethylenimenes and Methymelamines

An ethylenimene and/or a methylmelamine include, but are not limited to, hexamethylmelamine, used to treat ovary cancer; and thiotepa, which has been used to treat bladder, breast and ovary cancer.

iii. Alkyl Sulfonates

An alkyl sulfonate includes but is not limited to such drugs as busulfan, which has been used to treat chronic granulocytic leukemia.

Busulfan (also known as myleran) is a bifunctional alkylating agent. Busulfan is known chemically as 1,4-butanediol dimethanesulfonate. Busulfan is available in tablet form for oral administration, wherein for example, each scored tablet contains about 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. Busulfan has been shown to be superior to splenic irradiation with respect to survival times and maintenance of hemoglobin levels, and to be equivalent to irradiation at controlling splenomegaly.

iv. Nitrosourea

Nitrosureas, like alkylating agents, inhibit DNA repair proteins. They are used to treat non-Hodgkin's lymphomas, multiple myeloma, malignant melanoma, in addition to brain tumors. A nitrosourea include but is not limited to a carmustine (BCNU), a lomustine (CCNU), a semustine (methyl-CCNU) or a streptozocin. Semustine has been used in such cancers as a primary brain tumor, a stomach or a colon cancer. Stroptozocin has been used to treat diseases such as a malignant pancreatic insulinoma or a malignalnt carcinoid. Streptozocin has beeen used to treat such cancers as a malignant melanoma, Hodgkin's disease and soft tissue sarcomas.

a. Carmustine

Carmustine (sterile carmustine) is one of the nitrosoureas used in the treatment of certain neoplastic diseases. It is 1,3 bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has been used in treating such cancers as a multiple myeloma or a malignant melanoma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

Sterile carmustine is commonly available in 100 mg single dose vials of lyophilized material. The recommended dose of carmustine as a single agent in previously untreated patients is about 150 mg/m$^2$ to about 200 mg/m$^2$ intravenously every 6 weeks. This may be given as a single dose or divided into daily injections such as about 75 mg/m$^2$ to about 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention, for example about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$ to about 100 mg/m$^2$.

b. Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (about 0.05 mg/mL) and in absolute alcohol (about 70 mg/mL). Lomustine is relatively insoluble in water (less than about 0.05 mg/mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from about 30 mg/m$^2$ to 100 mg/m$^2$, about half of the radioactivity given was excreted in the form of degradation products within 24 hours. The serum half-life of the metabolites ranges from about 16 hours to about 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. Lomustine has been used to treat such cancers as small-cell lung cancer. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is about 130 mg/m$^2$ as a single oral dose every 6 weeks. In individuals with compromised bone marrow function, the dose should be reduced to about 100 mg/m$^2$ every 6 weeks. When lomustine is used in combination with other myelosuppressive drugs, the doses should be adjusted accordingly. It is understood that other doses may be used for example, about 20 mg/m$^2$, about 30mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$ to about 120 mg/m$^2$.

c. Triazine

A triazine include but is not limited to such drugs as a dacabazine (DTIC; dimethyltriazenoimidazolecarboxamide), used in the treatment of such cancers as a malignant melanoma, Hodgkin's disease and a sof-tissue sarcoma.

b. Antimetabolites

Antimetabolites disrupt DNA and RNA synthesis. Unlike alkylating agents, they specifically influence the cell cycle during S phase. They have used to combat chronic leukemias in addition to tumors of breast, ovary and the gastrointestinal tract. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

i. Folic Acid Analogs

Folic acid analogs include but are not limited to compounds such as methotrexate (amethopterin), which has been used in the treatment of cancers such as acute lymphocytic leukemia, choriocarcinoma, mycosis fungoides, breast, head and neck, lung and osteogenic sarcoma.

ii. Pyrimidine Analogs

Pyrimidine analogs include such compounds as cytarabine (cytosine arabinoside), 5-fluorouracil (fluouracil; 5-FU) and floxuridine (fluorode-oxyuridine; FudR). Cytarabine has been used in the treatment of cancers such as acute granulocytic leukemia and acute lymphocytic leukemias. Floxuridine and 5-fluorouracil have been used in the treatment of cancers such as breast, colon, stomach, pancreas, ovary, head and neck, urinary bladder and topical premalignant skin lesions.

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

iii. Purine Analogs and Related Inhibitors

Purine analogs and related compounds include, but are not limited to, mercaptopurine (6-mercaptopurine; 6-MP), thioguanine (6-thioguanine; TG) and pentostatin (2-deoxycoformycin). Mercaptopurine has been used in acute lymphocytic, acute granulocytic and chronic granulocytic leukemias. Thrioguanine has been used in the treatment of such cancers as acute granulocytic leukemia, acute lymphocytic leukemia and chronic lymphocytic leukemia. Pentostatin has been used in such cancers as hairy cell leukemias, mycosis fungoides and chronic lymphocytic leukemia.

c. Natural Products

Natural products generally refer to compounds originally isolated from a natural source, and identified has having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

i. Mitotic Inhibitors

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

a. Epipodophyllotoxins

Epipodophyllotoxins include such compounds as teniposide and VP16. VP16 is also known as etoposide and is used primarily for treatment of testicular tumors, in combination with bleomycin and cisplatin, and in combination with cisplatin for small-cell carcinoma of the lung. Teniposide and VP16 are also active against cancers such as testis, other lung cancer, Hodgkin's disease, non-Hodgkin's lymphomas, acute granulocytic leukemia, acute nonlymphocytic leukemia, carcinoma of the breast, and Kaposi's sarcoma associated with acquired immunodeficiency syndrome (AIDS).

VP16 is available as a solution (e.g., 20 mg/ml) for intravenous administration and as 50 mg, liquid-filled capsules for oral use. For small-cell carcinoma of the lung, the intravenous dose (in combination therapy) is can be as much as about 100 mg/m or as little as about 2 mg/m$^2$, routinely about 35 mg/m$^2$, daily for about 4 days, to about 50 mg/m$^2$, daily for about 5 days have also been used. When given orally, the dose should be doubled. Hence the doses for small cell lung carcinoma may be as high as about 200 mg/m$^2$ to about 250 mg/m$^2$. The intravenous dose for testicular cancer (in combination therapy) is about 50 mg/m$^2$ to about 100 mg/m$^2$ daily for about 5 days, or about 100 mg/m$^2$ on alternate days, for three doses. Cycles of therapy are usually repeated about every 3 to 4 weeks. The drug should be administered slowly (e.g., about 30 minutes to about 60 minutes) as an infusion in order to avoid hypotension and bronchospasm, which are probably due to the solvents used in the formulation.

b. Taxoids

Taxoids are a class of related compounds isolated from the bark of the ash tree, *Taxus brevifolia*. Taxoids include but are not limited to compounds such as docetaxel and paclitaxel.

Paclitaxel binds to tubulin (at a site distinct from that used by the vinca alkaloids) and promotes the assembly of microtubules. Paclitaxel is being evaluated clinically; it has activity against malignant melanoma and carcinoma of the ovary. In certain aspects, maximal doses are about 30 mg/m$^2$ per day for about 5 days or about 210 mg/m$^2$ to about 250 mg/m$^2$ given once about every 3 weeks.

c. Vinca Alkaloids

Vinca alkaloids are a type of plant alkaloid identified to have pharmaceutical activity. They include such compounds as vinblastine (VLB) and vincristine.

1. Vinblastine

Vinblastine is an example of a plant alkaloid that can be used for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. When the drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in about 7 days to about 10 days. If a moderate level of leukopenia (approximately 3000 cells/mm$^3$) is not attained, the weekly dose may be increased gradually by increments of about 0.05 mg/kg of body weight. In regimens designed to cure testicular cancer, vinblastine is used in doses of about 0.3 mg/kg about every 3 weeks irrespective of blood cell counts or toxicity.

An important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, testis cancer, neuroblastoma, and Letterer-Siwe disease (histiocytosis X), as well as in carcinoma of the breast and choriocarcinoma in women.

Doses of about 0.1 mg/kg to about 0.3 mg/kg can be administered or about 1.5 mg/m$^2$ to about 2 mg/m$^2$ can also be administered. Alternatively, about 0.1 mg/m$^2$, about 0.12 mg/m$^2$, about 0.14 mg/m$^2$, about 0.15 mg/m$^2$, about 0.2 mg/m$^2$, about 0.25 mg/m$^2$, about 0.5 mg/m$^2$, about 1.0 mg/m$^2$, about 1.2 mg/m$^2$, about 1.4 mg/m$^2$, about 1.5 mg/m$^2$, about 2.0 mg/m$^2$, about 2.5 mg/m$^2$, about 5.0 mg/m$^2$, about 6 mg/m$^2$, about 8 mg/m$^2$, about 9 mg/m$^2$, about 10 mg/m$^2$, to about 20 mg/m$^2$, can be given.

2. Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is about 0.4 mM.

Vinblastine and vincristine bind to plasma proteins. They are extensively concentrated in platelets and to a lesser extent in leukocytes and erythrocytes. Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than about 3 mg/dl (about 50 mM).

Vincristine sulfate is available as a solution (e.g., 1 mg/ml) for intravenous injection. Vincristine used together with corticosteroids is presently the treatment of choice to induce remissions in childhood leukemia; the optimal dosages for these drugs appear to be vincristine, intravenously, about 2 mg/m$^2$ of body-surface area, weekly; and prednisone, orally, about 40 mg/m$^2$, daily. Adult patients with Hodgkin's disease or non-Hodgkin's lymphomas usually receive vincristine as a part of a complex protocol. When used in the MOPP regimen, the recommended dose of vincristine is about 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, small cell lung, and carcinomas of the breast, bladder, and the male and female reproductive systems.

Doses of vincristine include about 0.01 mg/kg to about 0.03 mg/kg or about 0.4 mg/m$^2$ to about 1.4 mg/m$^2$ can be administered or about 1.5 mg/m$^2$ to about 2 mg/m$^2$ can also be administered. Alternatively, in certain embodiments, about 0.02 mg/m$^2$, about 0.05 mg/m$^2$, about 0.06 mg/m$^2$, about 0.07 mg/m$^2$, about 0.08 mg/m$^2$, about 0.1 mg/m$^2$, about 0.12 mg/m$^2$, about 0.14 mg/m$^2$, about 0.15 mg/m$^2$, about 0.2 mg/m$^2$, about 0.25 mg/m$^2$ can be given as a constant intravenous infusion.

d. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include, but are not limited to, bleomycin, dactinomycin, daunorubicin, doxorubicin (Adriamycin), plicamycin (mithramycin) and idarubicin. Widely used in clinical setting for the treatment of neoplasms these compounds generally are administered through intravenous bolus injections or orally.

1. Doxorubicin

Doxorubicin hydrochloride, 5,12-Naphthacenedione, (8s-cis)-10-[(3-amino-2,3,6--trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of diseases including ovarian, endometrial and breast tumors, bronchogenic oat-cell carcinoma, non-small cell lung carcinoma, stomach, genitourinary, thyroid, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma, soft tissue sarcoma, Ewing's sarcoma, rhabdomyosarcoma and acute lymphocytic leukemia. It is an alternative drug for the treatment of other diseases such as islet cell, cervical, testicular and adrenocortical cancers. It is also an immunosuppressant.

Doxorubicin is absorbed poorly and is preferably administered intravenously. The pharmacokinetics are multicompartmental. Distribution phases have half-lives of 12 minutes and 3.3 hours. The elimination half-life is about 30 hours, with about 40% to about 50% secreted into the bile. Most of the remainder is metabolized in the liver, partly to an active metabolite (doxorubicinol), but a few percent is excreted into the urine. In the presence of liver impairment, the dose should be reduced.

In certain embodiments, appropriate intravenous doses are, adult, about 60 mg/m$^2$ to about 75 mg/m$^2$ at about 21-day intervals or about 25 mg/m$^2$ to about 30 mg/m$^2$ on each of 2 or 3 successive days repeated at about 3 week to about 4 week intervals or about 20 mg/m² once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by about 50% if the serum bilirubin lies between about 1.2 mg/dL and about 3 mg/dL and by about 75% if above about 3 mg/dL. The lifetime total dose should not exceed about 550 mg/M2 in patients with normal heart function and about 400 mg/m² in persons having received mediastinal irradiation. In certain embodiments, and alternative dose regiment may comprise about 30 mg/m² on each of 3 consecutive days, repeated about every 4 week. Exemplary doses may be about 10 mg/m², about 20 mg/m², about 30 mg/m², about 50 mg/m², about 100 mg/m², about 150 mg/m², about 175 mg/m², about 200 mg/m², about 225 mg/m², about 250 mg/m², about 275 mg/m², about 300 mg/m², about 350 mg/m², about 400 mg/m², about 425 mg/m², about 450 mg/m², about 475 mg/m², to about 500 mg/m².

2. Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin (daunomycin; rubidomycin) intercalates into DNA, blocks DAN-directed RNA polymerase and inhibits DNA synthesis. It can prevent cell division in doses that do not interfere with nucleic acid synthesis.

In combination with other drugs it is often included in the first-choice chemotherapy of diseases such as, for example, acute granulocytic leukemia, acute myelocytic leukemia in adults (for induction of remission), acute lymphocytic leukemia and the acute phase of chronic myelocytic leukemia. Oral absorption is poor, and it preferably given by other methods (e.g., intravenously). The half-life of distribution is 45 minutes and of elimination, about 19 hours. The half-life of its active metabolite, daunorubicinol, is about 27 hours. Daunorubicin is metabolized mostly in the liver and also secreted into the bile (about 40%). Dosage must be reduced in liver or renal insufficiencies.

Generally, suitable intravenous doses are (base equivalent): adult, younger than 60 years, about 45 mg/m²/day (about 30 mg/m² for patients older than 60 year.) for about 1 day, about 2 days or about 3 days about every 3 weeks or 4 weeks or about 0.8 mg/kg/day for about 3 days, about 4 days, about 5 days to about 6 days about every 3 weeks or about 4 weeks; no more than about 550 mg/m² should be given in a lifetime, except only about 450 mg/m² if there has been chest irradiation; children, about 25 mg/m² once a week unless the age is less than 2 years. or the body surface less than about 0.5 m, in which case the weight-based adult schedule is used. It is available in injectable dosage forms (base equivalent) of about 20 mg (as the base equivalent to about 21.4 mg of the hydrochloride). Exemplary doses may be about 10 mg/m², about 20 mg/m², about 30 mg/m², about 50 mg/m², about 100 mg/m², about 150 mg/m², about 175 mg/m², about 200 mg/m², about 225 mg/m², about 250 mg/m², about 275 mg/m², about 300 mg/m², about 350 mg/m², about 400 mg/m², about 425 mg/m², about 450 mg/m², about 475 mg/m², to about 500 mg/m².

3. Mitomycin

Mitomycin (also known as mutamycin and/or mitomycin-C) is an antibiotic isolated from the broth of Streptomyces caespitosus which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced crosslinking. At high concentrations of the drug, cellular RNA and protein synthesis are also suppressed. Mitomycin has been used in tumors such as stomach, cervix, colon, breast, pancreas, bladder and head and neck.

In humans, mitomycin is rapidly cleared from the serum after intravenous administration. Time required to reduce the serum concentration by about 50% after a 30 mg. bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

4. Actinomycin D

Actinomycin D (Dactinomycin) [50–76–0]; $C_{62}H_{86}N_{12}O_{16}$ (1255.43) is an antineoplastic drug that inhibits DNA-dependent RNA polymerase. It is often a component of first-choice combinations for treatment of diseases such as, for example, choriocarcinoma, embryonal rhabdomyosarcoma, testicular tumor, Kaposi's sarcoma and Wilms' tumor. Tumors that fail to respond to systemic treatment sometimes respond to local perfusion. Dactinomycin potentiates radiotherapy. It is a secondary (efferent) immunosuppressive.

In certain specific aspects, actinomycin D is used in combination with agents such as, for example, primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hours. The drug does not pass the blood-brain barrier. Actinomycin D is supplied as a lyophilized powder (0/5 mg in each vial). The usual daily dose is about 10 mg/kg to about 15 mg/kg; this is given intravenously for about 5 days; if no manifestations of toxicity are encountered, additional courses may be given at intervals of about 3 weeks to about 4 weeks. Daily injections of about 100 mg to about 400 mg have been given to children for about 10 days to about 14 days; in other regimens, about 3 mg/kg to about 6 mg/kg, for a total of about 125 mg/kg, and weekly maintenance doses of about 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be about 100 mg/m², about 150 mg/m², about 175 mg/m², about 200 mg/m², about 225 mg/m², about 250 mg/m², about 275 mg/m², about 300 mg/m², about 350 mg/m², about 400 mg/m², about 425 mg/m², about 450 mg/m², about 475 mg/m², to about 500 mg/m².

5. Bleomycin

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of greater than about 35 mL per minute, the serum or plasma terminal elimination half-life of bleomycin is approximately 115 minutes. In patients with a creatinine clearance of less than about 35 mL per minute, the plasma or serum terminal elimination half-life increases exponentially as the creatinine clearance decreases. In humans, about 60% to about 70% of an administered dose is recovered in the urine as active bleomycin. In specific embodiments, bleomycin may be given by the intramuscular, intravenous, or subcutaneous routes. It is freely soluble in water. Because of the possibility of an anaphylactoid reaction, lymphoma patients should be treated with two units or less for the first two doses. If no acute reaction occurs, then the regular dosage schedule may be followed.

In preferred aspects, bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), esophagus, lung and genitourinary tract, Hodgkin's disease, non-Hodgkin's lymphoma, skin, penis, cervix, and vulva. It has also been used in the treatment of lymphomas and testicular carcinoma.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

d. Hormones and Antagonists

Hormonal therapy may also be used in conjunction with the present invention and/or in combination with any other cancer therapy or agent(s). The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

1. Adrenocorticosteroids

Corticosteroid hormones are useful in treating some types of cancer (e.g., non-Hodgkin's lymphoma, acute and chronic lymphocytic leukemias, breast cancer, and multiple myeloma). Though these hormones have been used in the treatment of many non-cancer conditions, they are considered chemotherapy drugs when they are implemented to kill or slow the growth of cancer cells. Corticosteroid hormones can increase the effectiveness of other chemotherapy agents, and consequently, they are frequently used in combination treatments. Prednisone and dexamethasone are examples of corticosteroid hormones.

2. Other Hormones and Antagonists

Progestins such as hydroxyprogesterone caproate, medroxyprogesterone acetate, and megestrol acetate have been used in cancers of the endometrium and breast. Estrogens such as diethylstilbestrol and ethinyl estradiol have been used in cancers such as breast and prostate. Antiestrogens such as tamoxifen have been used in cancers such as breast. Androgens such as testosterone propionate and fluoxymesterone have also been used in treating breast cancer. Antiandrogens such as flutamide have been used in the treatment of prostate cancer. Gonadotropin-releasing hormone analogs such as leuprolide have been used in treating prostate cancer. U.S. Pat. No. 4,418,068, incorporated herein by reference, discloses antiestrogenic and antiandrogenic benzothiophenes, such as, for example, 6-hydroxy-2-(4-hydroxyphenyl)-3-[4-(2-piperidinoethoxy)benzoyl]benzo[b]thiophene, and esters, ethers, and salts thereof for the treatment of cancers such as prostate and breast cancer.

e. Miscellaneous Agents

Some chemotherapy agents do not qualify into the previous categories based on their activities. They include, but are not limited to, platinum coordination complexes, anthracenedione, substituted urea, methyl hydrazine derivative, adrenalcortical suppressant, amsacrine, L-asparaginase, and tretinoin. It is contemplated that they are included within the compositions and methods of the present invention for use in combination therapies.

i. Platinum Coordination Complexes

Platinum coordination complexes include such compounds as carboplatin and cisplatin (cis-DDP). Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes, such as for example, intravenous, subcutaneous, intratumoral or intraperitoneal injection. Cisplatin can be used alone or in combination with other agents, with efficacious doses used in clinical applications of about 15 mg/m² to about 20 mg/m² for 5 days every three weeks for a total of three courses being contemplated in certain embodiments. Doses may be, for example, about 0.50 mg/m², about 1.0 mg/m², about 1.50 mg/m², about 1.75 mg/m², about 2.0 mg/m², about 3.0 mg/m², about 4.0 mg/m², about 5.0 mg/m², to about 10 mg/m².

ii. Other Agents

An anthracenedione such as mitoxantrone has been used for treating acute granulocytic leukemia and breast cancer. A substituted urea such as hydroxyurea has been used in treating chronic granulocytic leukemia, polycythemia vera, essental thrombocytosis and malignant melanoma. A methyl hydrazine derivative such as procarbazine (N-methylhydrazine, MIH) has been used in the treatment of Hodgkin's disease. An adrenocortical suppressant such as mitotane has been used to treat adrenal cortex cancer, while aminoglutethimide has been used to treat Hodgkin's disease.

2. Radiotherapeutic Agents

Radiotherapeutic agents include radiation and waves that induce DNA damage for example, γ-irradiation, X-rays, proton beam irradiation, V-irradiation, microwaves, electronic emissions, radioisotopes, and the like. Therapy may be achieved by irradiating the localized tumor site with the above described forms of radiations. It is most likely that all of these agents effect a broad range of damage DNA, on the precursors of DNA, the replication and repair of DNA, and the assembly and maintenance of chromosomes.

Radiotherapeutic agents and methods of administration, dosages, etc. are well known to those of skill in the art, and may be combined with the invention in light of the disclosures herein. For example, dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

3. Surgery

Approximately 60% of persons with cancer will undergo surgery of some type, which includes, for example, preventative, diagnostic or staging, curative and palliative surgery. Surgery, and in particular a curative surgery, may be used in conjunction with other therapies, such as the present invention and one or more other agents.

Curative surgery includes resection in which all or part of cancerous tissue is physically removed, excised and/or destroyed. It is further contemplated that surgery may remove, excise or destroy superficial cancers, precancers, or incidental amounts of normal tissue. Treatment by surgery includes for example, tumor resection, laser surgery, cryosurgery, electrosurgery, and miscopically controlled surgery (Mohs' surgery). Tumor resection refers to physical removal of at least part of a tumor. Upon excision of part of all of cancerous cells, tissue, or tumor, a cavity may be formed in the body.

Further treatment of the tumor or area of surgery may be accomplished by perfusion, direct injection or local application of the area with an additional anti-cancer agent. Such treatment may be repeated, for example, about every 1, about every 2, about every 3, about every 4, about every 5, about every 6, or about every 7 days, or about every 1, about every 2, about every 3, about every 4, or about every 5 weeks or about every 1, about every 2, about every 3, about every 4, about every 5, about every 6, about every 7, about every 8, about every 9, about every 10, about every 11, or about every 12 months. These treatments may be of varying dosages as well.

4. Immunotherapeutic Agents

An immunotherapeutic agent generally relies on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (e.g., a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. No. 5,686,072, U.S. Pat. No. 5,578,706, U.S. Pat. No. 4,792,447, U.S. Pat. No. 5,045,451, U.S. Pat. No. 4,664,911, and U.S. Pat. No. 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

a. Immune Stimulators

In a specific aspect of immunotherapy is to use an immune stimulating molecule as an agent, or more preferably in conjunction with another agent, such as for example, a cytokines such as for example IL-2, IL-4, IL-12, GM-CSF, tumor necrosis factor; interferons alpha, beta, and gamma; F42K and other cytokine analogs; a chemokine such as for example MIP-1, MIP-1beta, MCP-1, RANTES, IL-8; or a growth factor such as for example FLT3 ligand.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anticancer activity.

Another cytokine specifically contemplate is interferon alpha. Interferon alpha has been used in treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

b. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. For example, human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers (Bajorin et al., 1988).

c. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

d. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

5. Other Biological Agents

It is contemplated that other agents may be used in combination with the present invention to improve the therapeutic efficacy of treatment. These additional agents include, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents such as for example, hyperthermia.

It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population.

In other embodiments, cytostatic or differentiation agents can be used in combination with the present invention to improve the anti-hyerproliferative efficacy of the treatments.

Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as, for example, the antibody c225, could be used in combination with the present invention to improve the treatment efficacy.

Another form of therapy for use in conjunction with the present invention and/or other agent(s) includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

K. Genetic Vaccines

In certain embodiments, an immune response may be promoted by transfecting or inoculating an animal with a nucleic acid encoding an antigen. One or more cells comprised within a target animal then expresses the sequences encoded by the nucleic acid after administration of the nucleic acid to the animal. Thus, the vaccine may comprise "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

For a nucleic acid delivery composition to be useful as a vaccine, an antigenic composition encoded by or comprised in the a nucleic acid delivery composition must induce an immune response to the antigen in a cell, tissue or animal (e.g., a human). As used herein, an "antigenic composition" may comprise an antigen (e.g., a peptide or polypepide), a nucleic acid encoding an antigen (e.g., an antigen expression vector), or a cell expressing or presenting an antigen. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

A vaccine of the present invention may vary in its composition of proteinaceous, nucleic acid and/or cellular components. In a non-limiting example, a nucleic encoding an antigen might also be formulated with a proteinaceous adjuvant. Of course, it will be understood that various compositions described herein may further comprise additional components. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

The nucleotide and protein, polypeptide and peptide encoding sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified, combined (e.g., ligated) with the sequences to produce nucleic acid vectors, described herein, administered to a cell, tissue, organ or organism and/or expressed using the techniques disclosed herein or by any technique that would be know to those of ordinary skill in the art (e.g., Sambrook et al., 1989). Though a nucleic acid may be expressed in an in vitro expression system, in preferred embodiments the nucleic acid comprises a vector for in vivo replication and/or expression.

1. Cellular Vaccine Antigens

In another embodiment, a vaccine may comprise a cell expressing the antigen. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

In particular embodiments, it is contemplated that nucleic acids encoding antigens of the present invention may be transfected into plants, particularly edible plants, and all or part of the plant material used to prepare a vaccine, such as for example, an oral vaccine. Such methods are described in U.S. Pat. Nos. 5,484,719, 5,612,487, 5,914,123, 5,977,438 and 6,034,298, each incorporated herein by reference.

2. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

a. Immunomodulators

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

1. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β--interferon, α-interferon, γ-interferon, angiostatin, thrombospondin, endostatin, GM-CSF, G-CSF, M-CSF, METH-1, METH-2, tumor necrosis factor, TGFβ, LT and combinations thereof.

ii. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

iii. Immunogenic Carrier Proteins

In certain embodiments, an antigenic composition's may be chemically coupled to a carrier or recombinantly expressed with a immunogenic carrier peptide or polypetide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

iv. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m$^2$) (Johnson/Mead, NJ), or a nucleic acid encoding a proteinaceous sequence involved in one or more immune helper functions, such as B-7.

b. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent such as alum used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cell(s) such as *C. parvum* or an endotoxin or a lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute also may be employed.

Some adjuvants, for example, are certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (*bacillus* Calmette-Guerin, an attenuated strain of *Mycobacterium*) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign nucleic acids into BCG (Jacobs et al., 1987; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE® BCG (Organon Inc., West Orange, N.J.).

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

One group of adjuvants preferred for use in some embodiments of the present invention are those that can be encoded by a nucleic acid (e.g., DNA or RNA). It is contemplated that such adjuvants may be encoded in a nucleic acid (e.g., an expression vector) encoding the antigen, or in a separate vector or other construct. These nucleic acids encoding the adjuvants can be delivered directly, such as for example with lipids or liposomes.

c. Excipients, Salts and Auxilary Substances

An antigenic composition of the present invention may be mixed with one or more additional components (e.g., excipients, salts, etc.) which are pharmaceutically acceptable and compatible with at least one active ingredient (e.g., antigen). Suitable excipients are, for example, water, saline, dextrose, glycerol, ethanol and combinations thereof.

An antigenic composition of the present invention may be formulated into the vaccine as a neutral or salt form. A pharmaceutically-acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2-ethylamino ethanol, histidine, procaine, and combinations thereof.

In addition, if desired, an antigenic composition may comprise minor amounts of one or more auxiliary substances such as for example wetting or emulsifying agents, pH buffering agents, etc. which enhance the effectiveness of the antigenic composition or vaccine.

3. Vaccine Component Purification

In any case, a vaccine component (e.g., a nucleic acid encoding a proteinaceous composition) may be isolated and/or purified from the chemical synthesis reagents, cell or cellular components. In a method of producing the vaccine component, purification is accomplished by any appropriate technique that is described herein or well-known to those of skill in the art (e.g., Sambrook et al., 1989). Although preferred for use in certain embodiments, there is no general requirement that an antigenic composition of the present invention or other vaccine component always be provided in their most purified state. Indeed, it is contemplated that less substantially purified vaccine component, which is nonetheless enriched in the desired compound, relative to the natural state, will have utility in certain embodiments, such as, for example, total recovery of protein product, or in maintaining the activity of an expressed protein. However, it is contemplate that inactive products also have utility in certain embodiments, such as, e.g., in determining antigenicity via antibody generation.

The present invention also provides purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally-obtainable state, e.g., relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al., 1989; and Freifelder, Physical Biochemistry, Second Edition, pages 238–246, incorporated herein by reference).

Given many DNA and proteins are known (see for example, the National Center for Biotechnology Information's Genbank and GenPept databases (http://www.ncbi.nlm.nih.gov/)), or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al., 1989, incorporated herein by reference). In further aspects, a purification of a proteinaceous sequence may be conducted by recombinately expressing the sequence as a fusion protein. Such purification methods are routine in the art. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

4. Vaccine Preparations

Once produced, synthesized and/or purified, an antigen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition as active ingredient(s), in light of the present disclosure. In preferred embodiments, the compositions of the present invention are prepared to be pharmacologically acceptable vaccines.

5. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularily, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 100 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the antigen can be performed, following immunization.

6. Enhancement of an Immune Response

The present invention includes a method of enhancing the immune response in a subject comprising the steps of contacting one or more lymphocytes with an antigenic composition. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g., a patient), then pulsed with composition comprising an antigenic composition. In a preferred embodiment, the lymphocyte(s) may be be administered to the same or different animal (e.g., same or different donors).

a. Cytotoxic T Lymphocytes

In certain embodiments, T-lymphocytes are specifically activated by contact with an antigenic composition of the present invention. In certain embodiments, T-lymphocytes are activated by contact with an antigen presenting cell that is or has been in contact with an antigenic composition of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cells that recognizes an antigen-MHC complex proliferates and differentiates into an effector cell called a cytotoxic T lymphocyte (CTL). CTLs eliminate cells of the body displaying antigen by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with DC infected with an adenovirus vector containing antigen using standard 4 h $^{51}$Cr release microtoxicity assays. In another fluorometric assay developed for detecting cell-mediated cytotoxicity, the fluorophore used is the non-toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}$Cr release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

b. Antigen Presenting Cells

In general, the term "antigen presenting cell" can be any cell that accomplishes the goal of the invention by aiding the enhancement of an immune response (i.e., from the T-cell or -B-cell arms of the immune system) against an antigen. Such cells can be defined by those of skill in the art, using methods disclosed herein and in the art. As is understood by one of ordinary skill in the art (see for example Kuby, 1993, incorporated herein by reference), and used herein certain embodiments, a cell that displays or presents an antigen normally or preferentially with a class II major histocompatability molecule or complex to an immune cell is an "antigen presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65–66, 71–74 1986; Campbell, pp. 75–83, 1984; Kohler and Milstein, 1975; Kohler and Milstein, 1976, Gefter et al., 1977, each incorporated herein by reference. In some cases, the immune cell to which an antigen presenting cell displays or presents an antigen to is a $CD4^+T_H$ cell. Additional molecules expressed on the APC or other immune cells may aid or improve the enhancement of an immune response. Secreted or soluble molecules, such as for example, immunomodulators and adjuvants, may also aid or enhance the immune response against an antigen. Such molecules are well known to one of skill in the art, and various examples are described herein.

L. Pharmaceutical Preparations

Pharmaceutical compositions of the present invention comprise an effective amount of one or more nucleic acid delivery compositions, a component of a nucleic acid delivery composition, or an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one component of a nucleic acid delivery composition, such a composition, or an additional agent will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

The nucleic acid delivery composition, a component of such a composition or an additional agent may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The nucleic acid delivery composition, component of such a composition or additional agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the nucleic acid delivery composition, component of such a composition or additional agent is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

M. Kits

Any of the compositions described herein may be comprised in a kit. In a non-limiting example, a nucleic acid delivery composition, a component of a nucleic acid delivery composition, and/or an additional agent, may be comprised in a kit. The kits will thus comprise, in suitable container means, a nucleic acid delivery composition, a component of a nucleic acid delivery composition, and/or an additional agent of the present invention.

The kits may comprise a suitably aliquoted a nucleic acid delivery composition, a component of a nucleic acid delivery composition, and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the a nucleic acid delivery composition, a component of a nucleic acid delivery composition, additional agent, and any other reagent containers in close confinement for commercial sale. Such containers may include injection or blow-molded plastic containers into which the desired vials are retained.

Therapeutic kits of the present invention are kits comprising a nucleic acid delivery composition, a component of a nucleic acid delivery composition and/or an additional agent. Such kits will generally contain, in suitable container means, a pharmaceutically acceptable formulation of a nucleic acid delivery composition, a component of a nucleic acid delivery composition and/or an additional agent in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The a nucleic acid delivery composition, a component of a nucleic acid delivery composition and/or an additional agent compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which a nucleic acid delivery composition, a component of a nucleic acid delivery composition and/or an additional agent formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/ administration and/or placement of the ultimate a nucleic acid delivery composition, a component of a nucleic acid delivery composition and/or an additional agent within the body of an animal. Such an instrument may be a syringe, pipette, forceps, and/or any such medically approved delivery vehicle.

N. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Transduction Analysis In Vitro Using Formula 1

Initially, studies utilizing PEI for nucleic acid delivery were designed to develope PEI as a backbone for targeted non-viral delivery composition formation using previous formulations (Bousiff et al., 1995; Boussif et al., 1996). This typically involved using equal volumes of PEI and DNA that are mixed together by either adding PEI to DNA or DNA to PEI. PEI (Sigma-Aldrich) was used and the plasmid DNA pCMV/β-gal, which comprises a cytomegalovirus enhancer/promoter driving E. coli β-galactosidase expression, was isolated using either Qiagen or Clontech endotoxin free DNA isolation kits. All DNA preparations were determined to be at less than 0.05 endotoxin units/µg DNA. The following mixing procedure termed "Formulation I" was used for the initial delivery composition formation:

Formulation I:

6 µg DNA in a volume of 30 µl of water was added to PEI in a volume of 30 µl of water, with continued vortexing. This method was used to produce concentrations comprising a final amine:phosphate ratio of 9:1, 7.5:1, 5.6:1, 4.3:1 and 2.7:1.

The reaction was then incubated at room temperature for 20 to 30 minutes and then 30 µl of the composition comprising 3 µg of DNA was added to cells and incubated for 1 to 3 hours in serum free media. The media containing the delivery composition was then removed and replaced with media containing the correct FCS concentration.

Twenty-four hours after the initial delivery composition incubation, the cells were stained histochemically for β-gal expression and then the percentage of positive staining cells determined 24 hours later.

Figure 1:
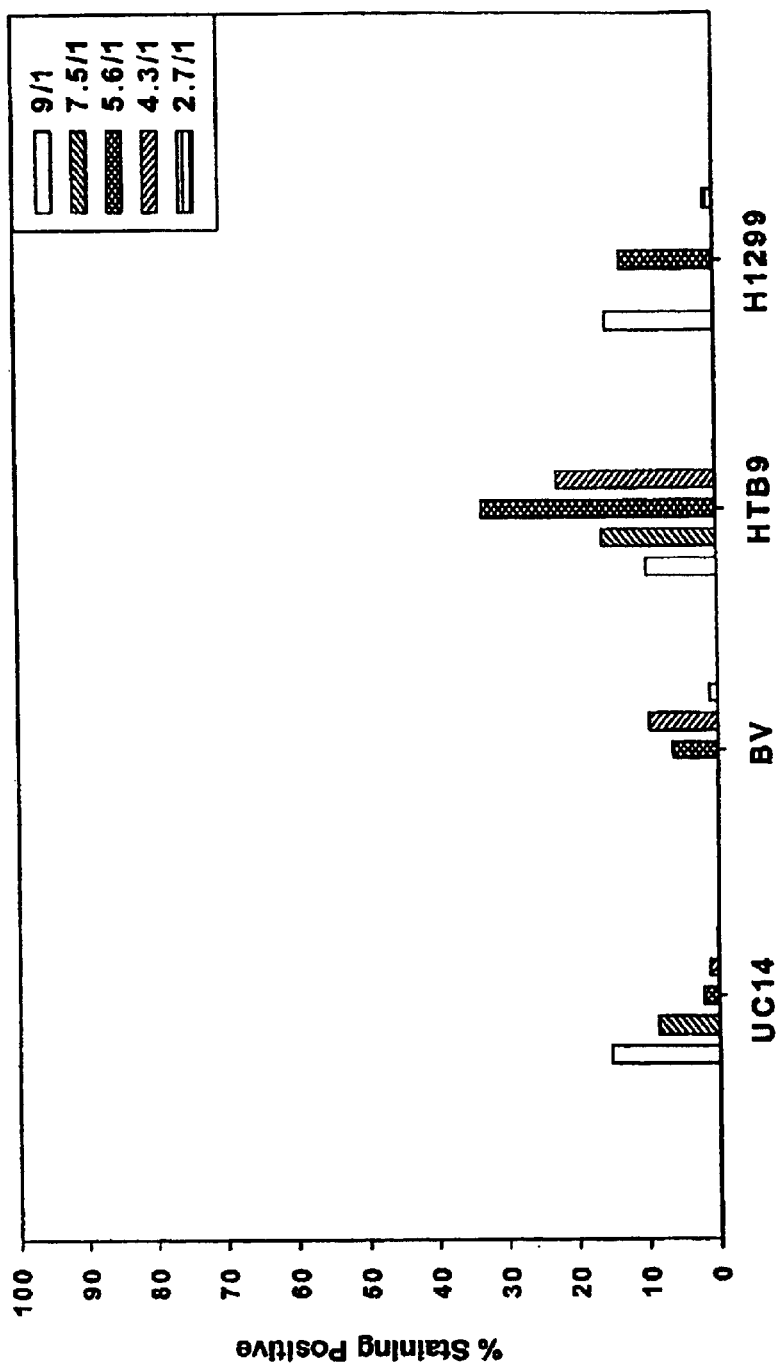
FIG. 1. Transduction analysis of cancer cell lines using the published PEI/DNA vector formulation. Vector preparations were prepared, incubated with cells (2.5 μg DNA/well) for 3 hours, removed, and then transduction was analyzed 24 hours later by histochemical staining for β-gal. DNA isolated with Qiagen kit. The percent staining positive was calculated by dividing the number of blue staining cells by the total number of cells counted in at least 3 areas of each well. The box represents the amine:phosphate ratio used in delivery composition formation.

The transduction efficiency of three bladder cancer and one non-small cell lung cancer cell line was determined using the delivery composition produced with Formulation I (FIG. 1). Transduction only as high as 30% was obtained. More importantly, there was no one optimum concentration of PEI that could be used to produce high level transduction for all the cell lines used, which reduces the utility of this delivery composition formulation in many applications. However, for the most part, higher transduction did occur at amine:phosphate ratio's between 4.3:1 and 9:1. This result is similar to reports in the literature that have observed the highest level of transduction to occur at these ratio's. However, it should be noted that amine:phosphate ratio's in this range are known to produce high cellular toxicity (Boussif et al., 1995; Boussif et al., 1996; Hart, 2000).

Attempts to use higher amine:phosphate ratios (amine:phosphate up to 18) by this method produced much higher toxicity results.

An alternative approach that was contemplated was to stop using the branched form of PEI and switch to a new form of PEI that had been recently developed (Goula et al., 1998). This linear form of PEI had been reported to produce highly efficient nucleic acid delivery to the lung with little or no toxicity (Goula et al., 1998; Rudolph et al., 2000). However, the this form was too cost prohibitive (approximately $250/500 µl) for it to be used economically in the studies or in future clinical applications. These studies were continued using the branched chain PEI, while many other groups moved on to use the linear form of PEI, based upon the lower cost ($67/500 ml or $90/L) and the easy availability of large quantities of the branched chain molecule.

Example 2

Transduction Analysis In Vitro Using Formula 2

Commercially available Qiagen and Clontech kits only produced DNA yields of 1–2 milligrams/liter of culture media. In addition, the Qiagen isolation kit often produced a white precipitate would co-purify with the DNA raising questions related to vector purity.

DNA was tested that was isolated using a new published procedure in which yields of >2–4 milligrams of DNA from 200 milliliters of initial bacterial culture could be obtained (Templeton et al., 1997). Once DNA was isolated using this new procedure, transduction was again examined on the same 4 cell lines.

In several of the studies, a surprising result was observed in which transduction levels in some samples using formulation I with DNA isolated from this new procedure would increase to much higher levels than in other samples. Several studies were performed comparing how the PEI and DNA were combined. One study in particular used the following procedure termed "Formulation II":

Formulation II:

PEI in a small volume (10 µl, various concentrations) was added to DNA in a larger volume (60 µl, 6 µg), either slowly by drop or quickly by a quick addition, both while vortexing for 30 sec.

Following this, the reaction was allowed to incubate for 20 to 30 min at room temperature and then added to cells (30 µl/2.5 µg of DNA) in serum free media and incubated for 3 hrs. The media containing delivery composition was then removed and replaced with media containing the correct FCS concentration.

Twenty-four hours after the initial delivery composition incubation, the cells were stained histochemically for β-gal expression and then the percentage of positive staining cells determined 24 hrs later.

Figure 2:
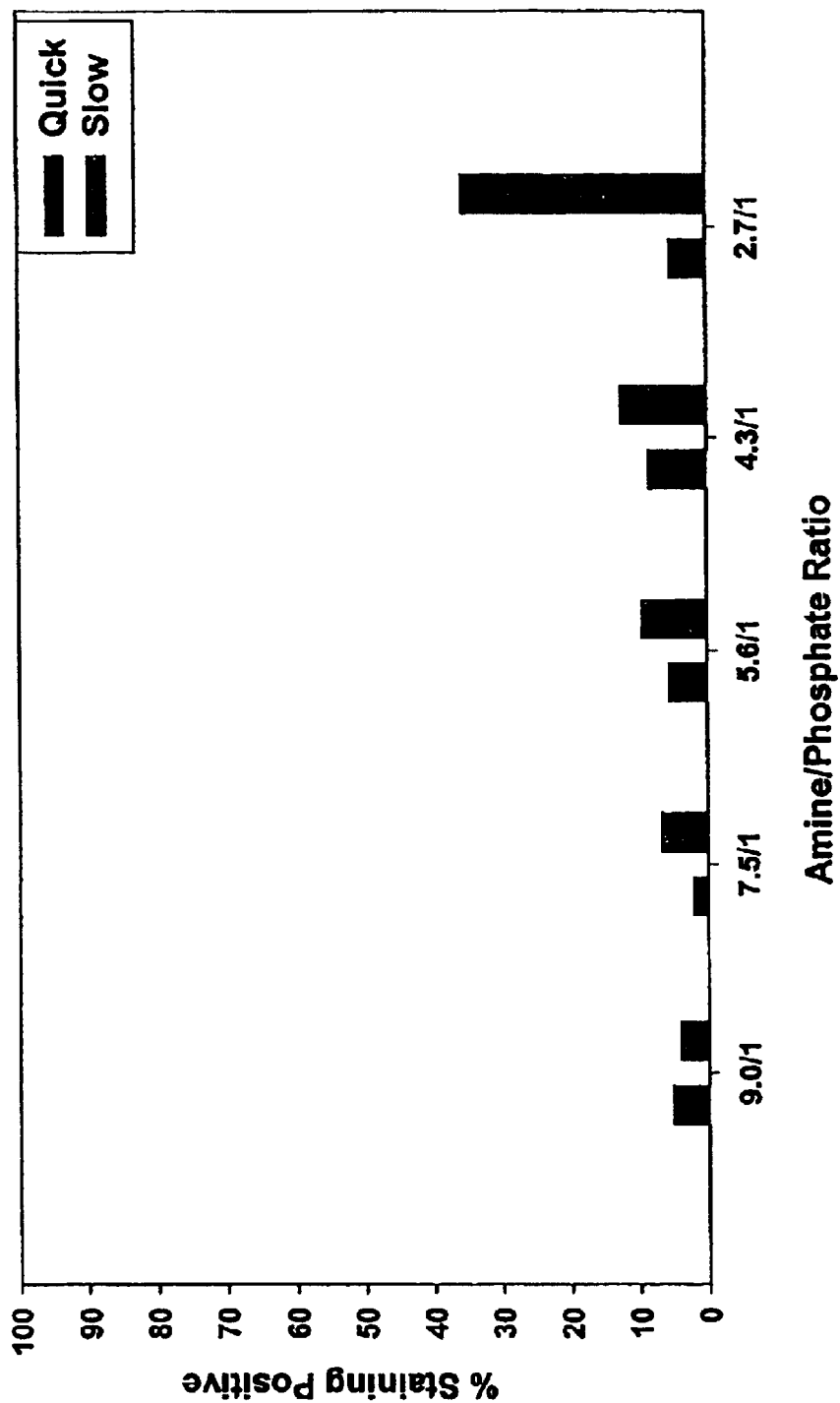
FIG. 2. Comparison of quick vs. slow addition of PEI to DNA. Delivery composition (2.5 µg DNA) was incubated with H1299 cells and analyzed for transduction as outlined in FIG. 1.

A sharp and surprising increase in transduction was observed in a sample comprising an amine:phosphate ratio of 2.7:1 which had used a drop-wise method of adding PEI to DNA (FIG. 2).

Figure 3:
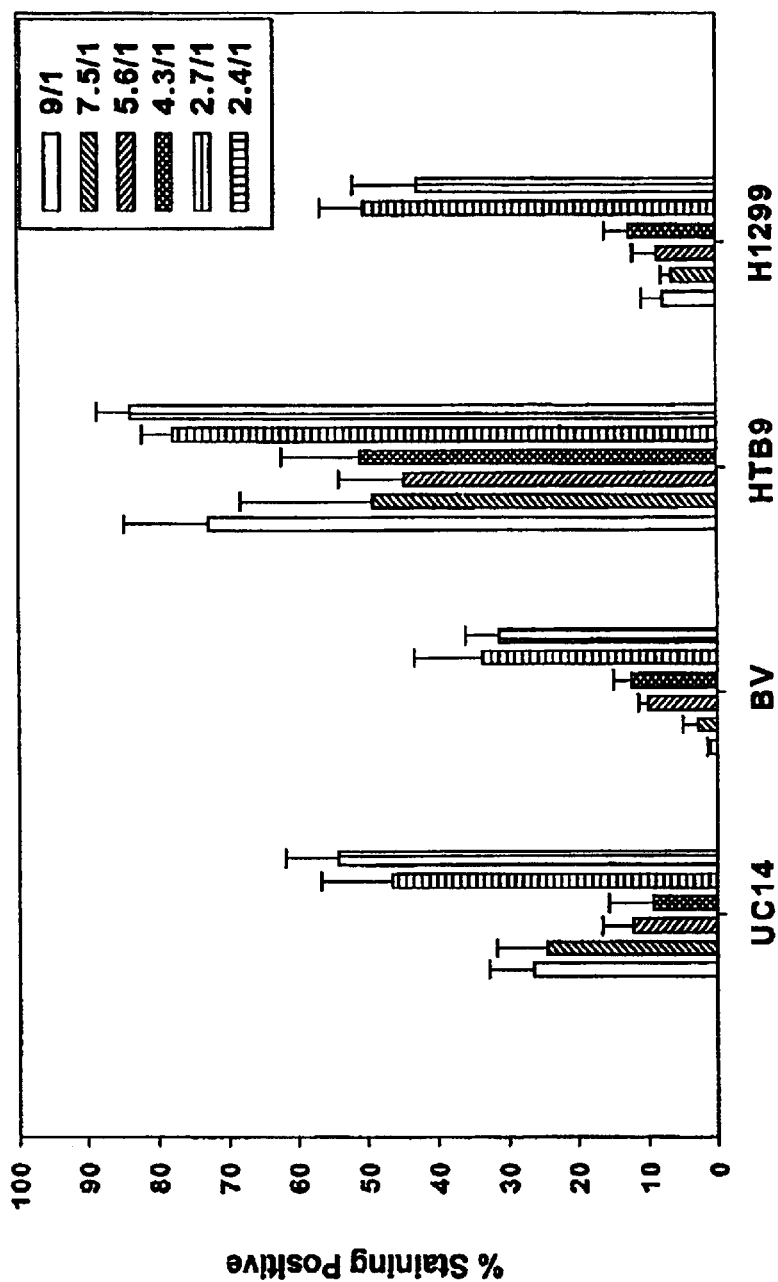
FIG. 3. Transduction analysis of cancer cell lines using the new PEI/DNA vector formulation. Vector was made at various amine:phosphate (a/p) ratios, incubated with cells (2.5 µg DNA/well) for 3 hours, removed, and then transduction was analyzed 24 hours later by histochemical staining for β-gal. The percent staining positive was calculated by dividing the number of blue staining cells by the total number of cells counted in at least 3 areas of each well. The box represents the amine:phosphate ratio used in delivery composition formation.

Formulation II was then tested after preparation by a drop-wise addition of 10 µl PEI while vortexing, using amine:phosphate ratios ranging from 9:1 to 2.4:1 on the 4 cancer cell lines. Transduction efficiencies were vastly increased by this method, approaching 90% in some instances. This high level transduction could be obtained by essentially using an amine:phosphate ratio of 2.7:1 (FIG. 3).

Figure 4:
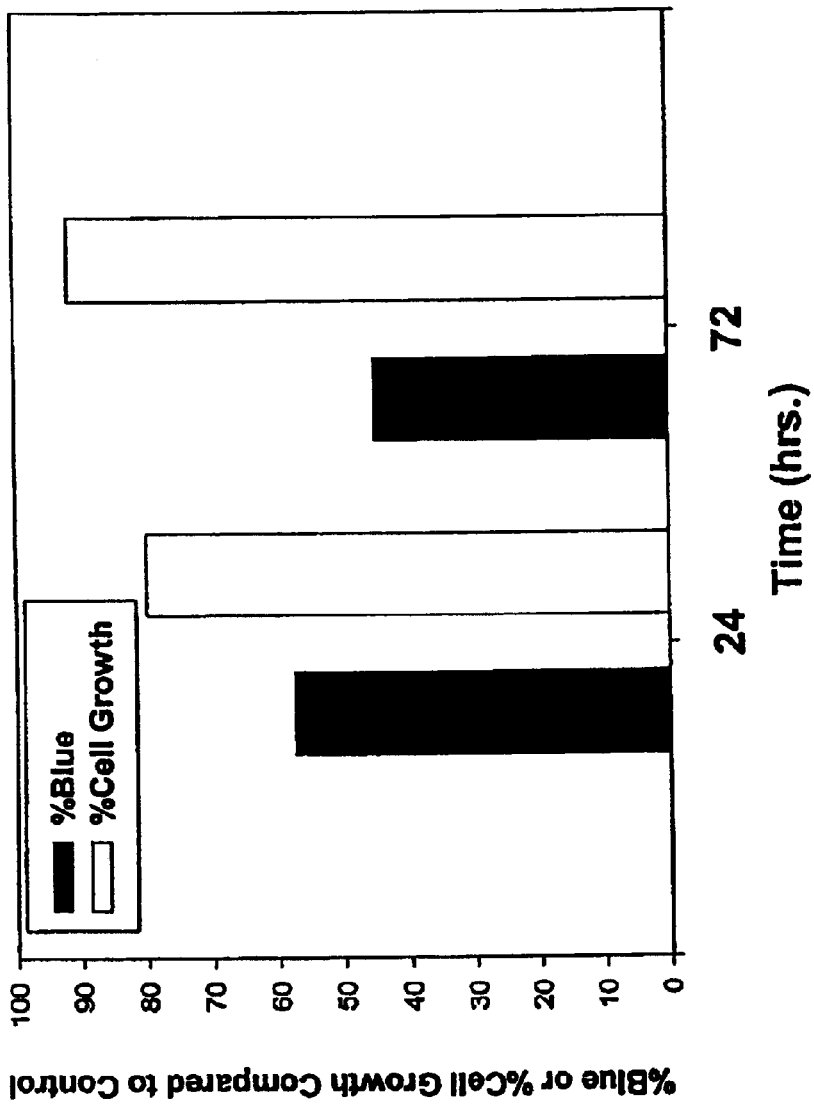
FIG. 4. Toxicity analysis of PEI:DNA delivery composition formulation II. H1299 cells were incubated with PEI:DNA delivery composition formulation II (2.5 µg DNA, amine:phosphate ratio=2.7:1) for 3 hrs. in 0% FCS. The media containing delivery composition was then replaced with media containing the normal FCS concentration. Cells were then incubated at 37° C. with $CO_2$ until analyzed at 24 and 72 hrs. following the initial incubation with delivery composition. At the appropriate time points, cells were either stained for β-gal expression or counted. The percent blue represents the number of cells staining positive divided by the total number of cells counted. The percent cell growth represents the total number of cells counted in the treated wells divided by the number cells counted in the non-treated control.
Figure 5:
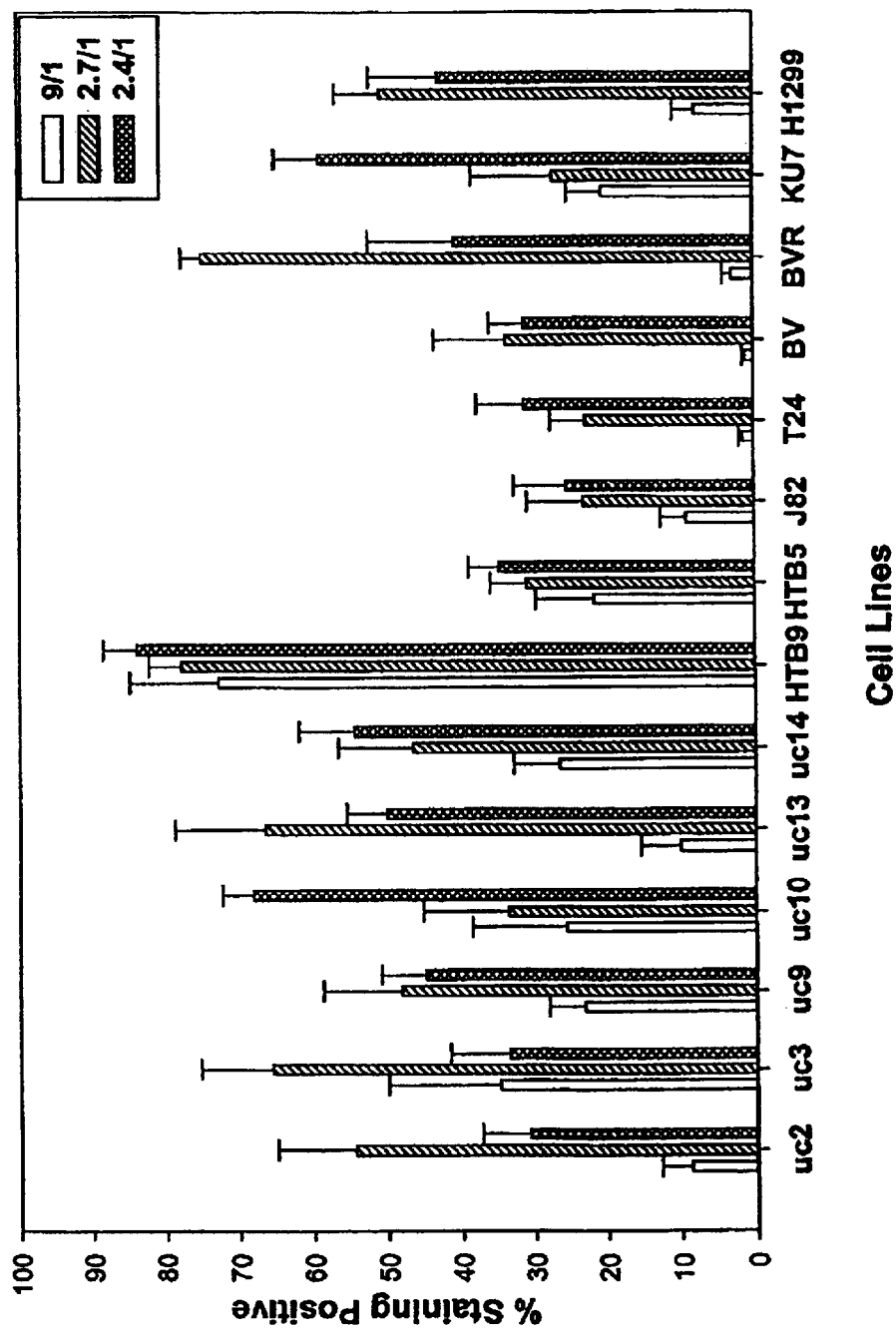
FIG. 5. Transduction analysis of bladder cancer cell lines with PEI:DNA delivery composition formulation II. Delivery composition was incubated with cells and transduction was analyzed as in FIG. 1. The box represents the amine:phosphate ratio.
Figure 6:
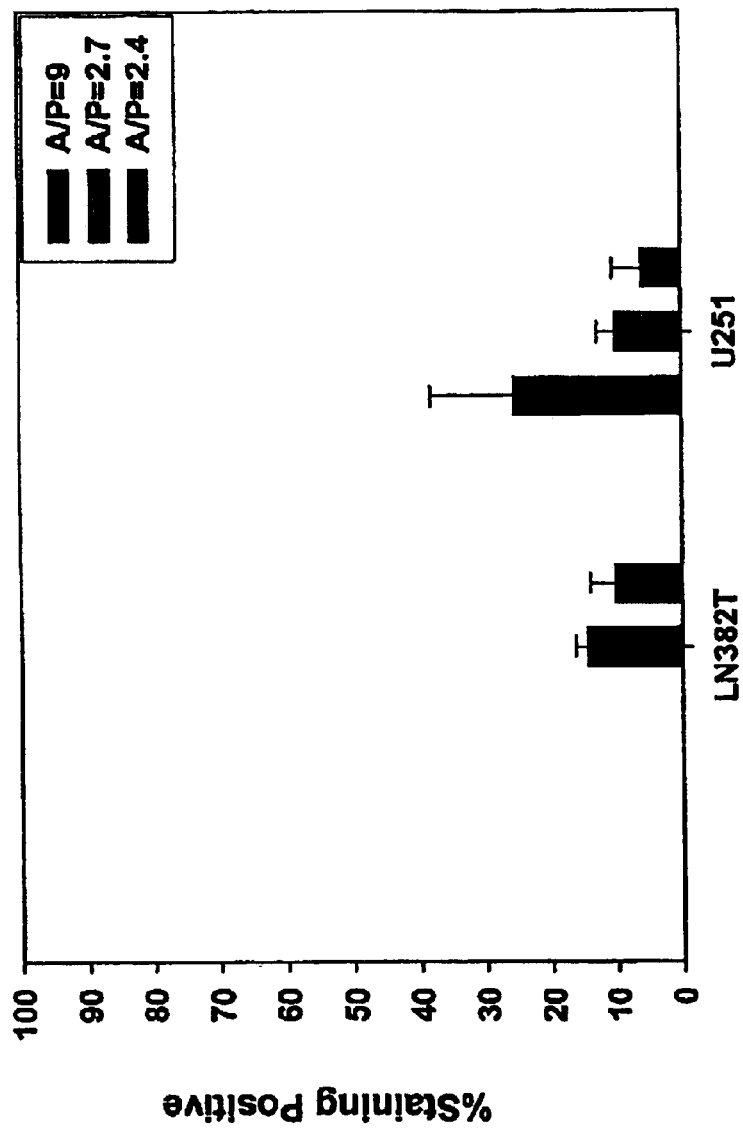
FIG. 6. Transduction analysis of brain cancer cell lines with PEI:DNA delivery composition formulation II. Delivery composition was incubated with cells and transduction was analyzed as in FIG. 1. The box represents the amine:phosphate ratio.
Figure 7:
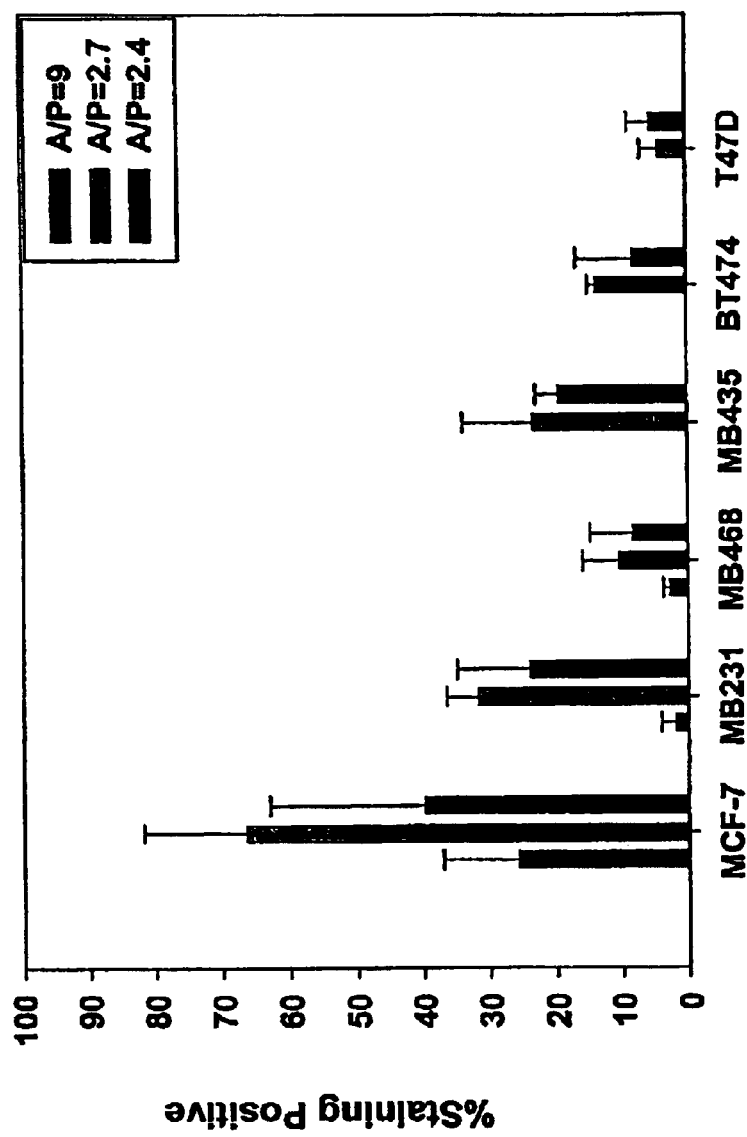
FIG. 7. Transduction analysis of breast cancer cell lines with PEI:DNA delivery composition formulation II. Delivery composition was incubated with cells and transduction was analyzed as in FIG. 1. The box represents the amine:phosphate ratio.
Figure 8:
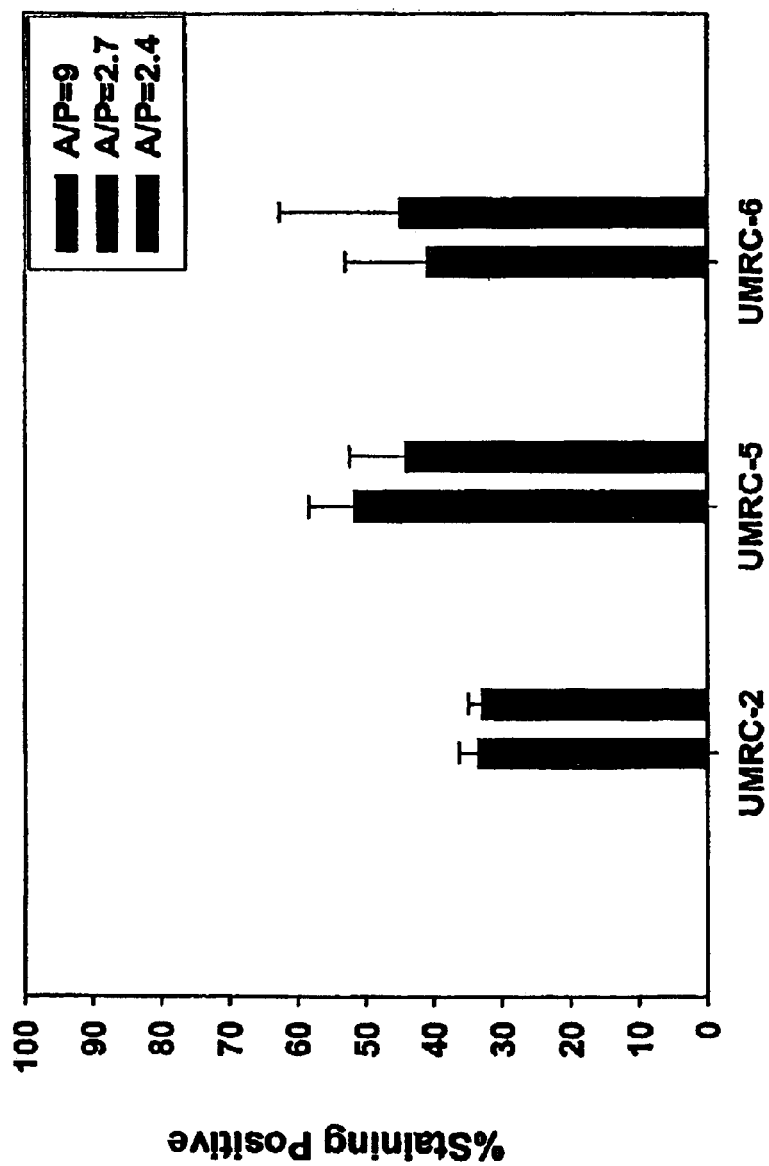
FIG. 8. Transduction analysis of kidney cancer cell lines with PEI:DNA delivery composition formulation II. Delivery composition was incubated with cells and transduction was analyzed as in FIG. 1. The box represents the amine:phosphate ratio.
Figure 9:
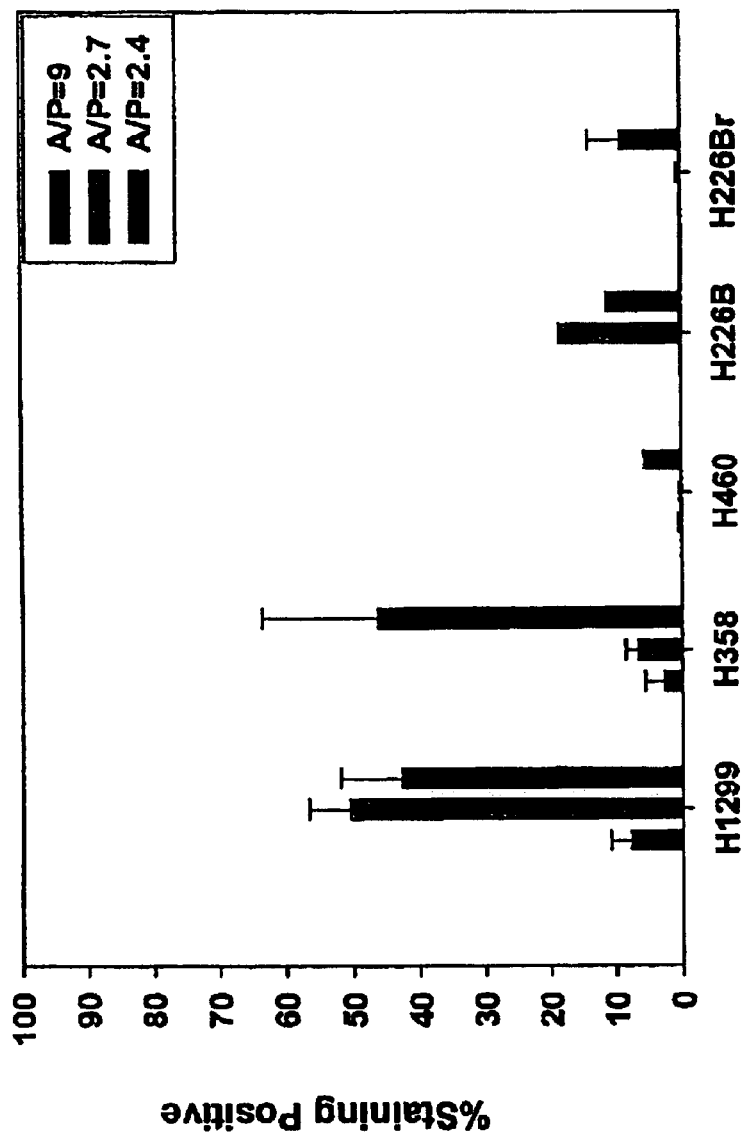
FIG. 9. Transduction analysis of lung cancer cell lines with PEI:DNA delivery composition formulation II. Delivery composition was incubated with cells and transduction was analyzed as in FIG. 1. The box represents the amine:phosphate ratio.
Figure 10:
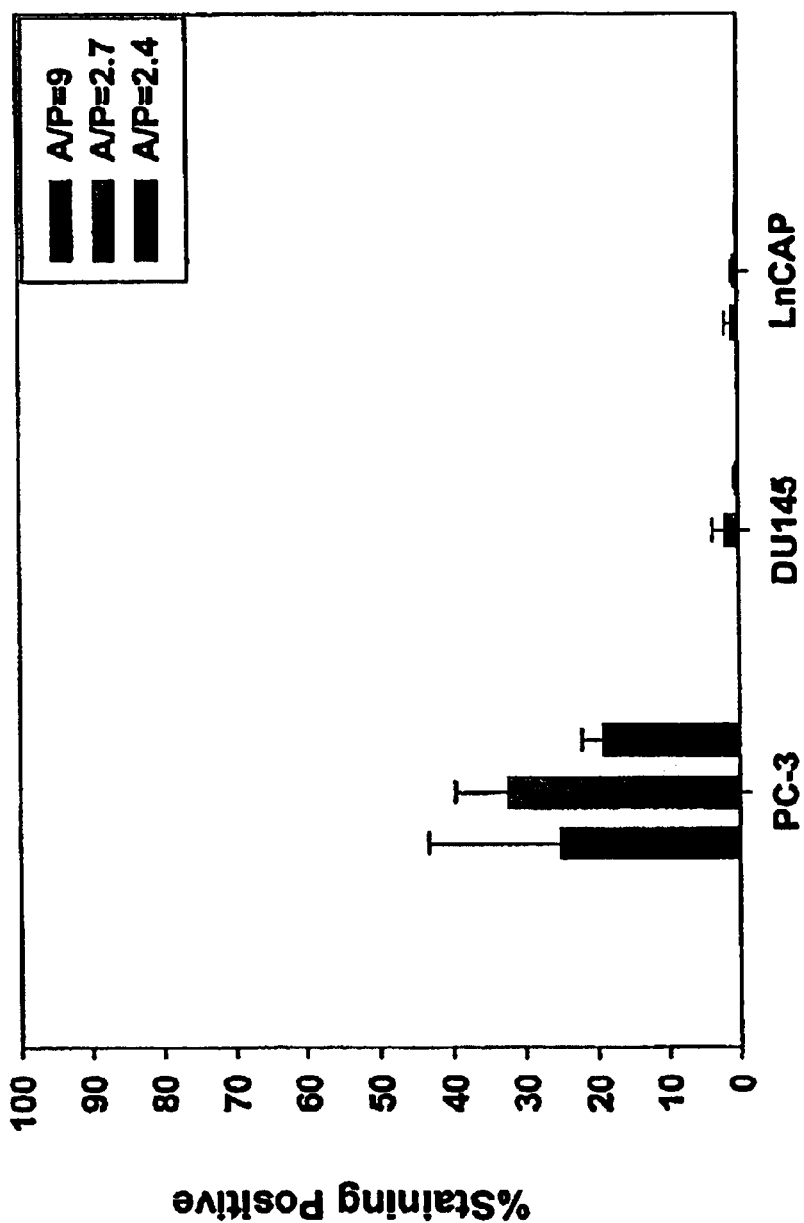
FIG. 10. Transduction analysis of prostate cancer cell lines with PEI:DNA delivery composition formulation II. Delivery composition was incubated with cells and transduction was analyzed as in FIG. 1. The box represents the amine:phosphate ratio.

At this concentration of PEI, it was expected that the amount of toxicity to be very low as it is more than 3× lower than previously used PEI concentrations previously used. This was confirmed by testing the cell line H1299 for transduction (stain/count) and toxicity (by cell counts) 24 and 72 hrs after incubating the delivery composition (formulation II, new procedure DNA, amine:phosphate ratio of 2.7:1) with the cells. Little or no toxicity was seen at 24 and 72 hrs. after the initial incubation of the delivery composition, even when cells were transduced at transduction efficiencies of 40% to 60% (FIG. 4). In contrast, cells transduced with delivery composition made with DNA isolated by the Qiagen or Clontech kits demonstrated higher toxicity and lower transduction.

The "formulation II' procedure was the used to demonstrate that the delivery composition was capable of producing efficient, reproducible transduction using the delivery composition at amine:phosphate ratio's of 9:1, 7.5:1, 5.6:1, 4.3:1, 2.7:1, and 2.4:1 on several different types of cell lines. Panels of cell lines from bladder, brain, breast, kidney, lung, and prostate were tested for transduction (FIGS. 5–10; amine:phosphate ratio's of 9:1, 2.7:1, and 2.4:1 are shown). Transduction efficiencies ranging from 10% to 90% were obtained in a large majority of the cell lines; however, there were several that produced little or no transduction. More importantly, this transduction could be obtained by using essentially a single concentration of PEI (amine:phosphate ratio of approximately 2.7:1). These studies involved the same general transduction conditions for each type of cell line used and did not involve any optimization of transduction for each cell lines such as incubation time, dose of delivery composition etc. The simple nature of this delivery composition should however, afford any user to perform simple changes to these variables to optimize transduction. In addition, it should also be stressed that the determination of transduction was based on β-gal staining which has been identified to severely underestimate the amount of transduced cells by as much as seventy percent (Couffinhal et al., 1997). Thus, many instances, the percentage of transduced cells is probably much higher than estimated by this method.

Figure 11:
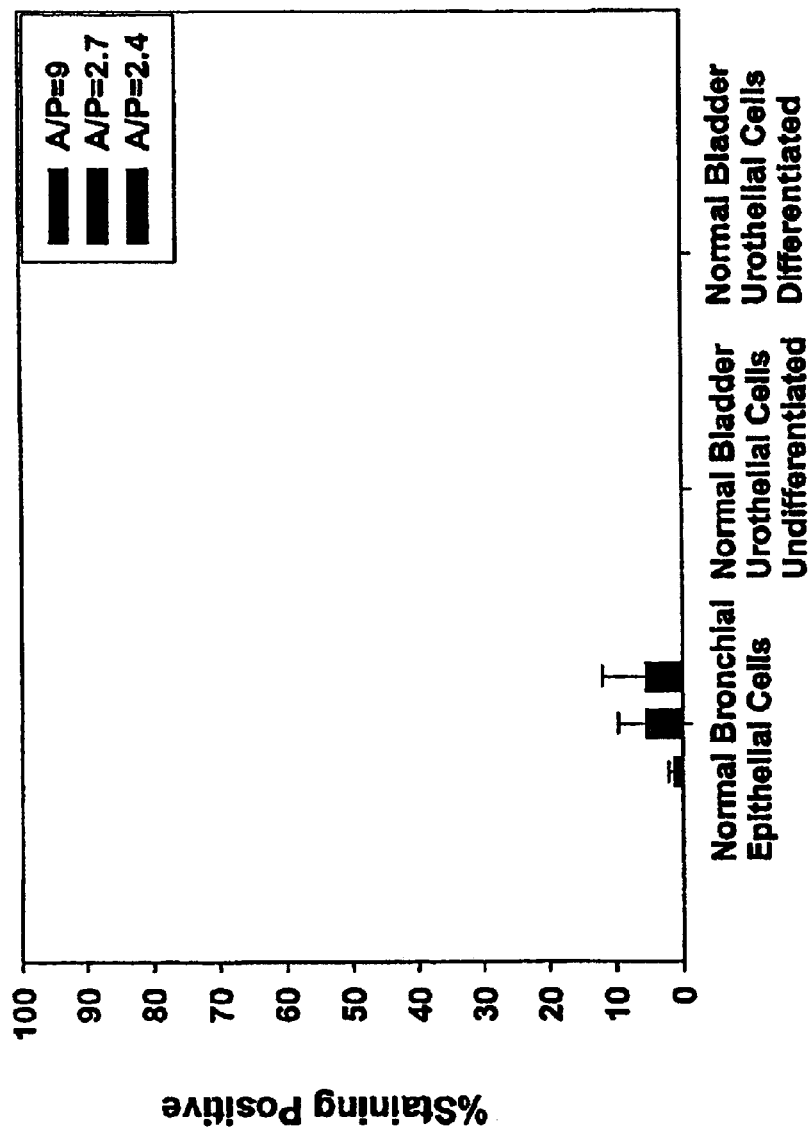
FIG. 11. Transduction analysis of normal cell lines with PEI:DNA delivery composition formulation II. Delivery composition was incubated with cells and transduction was analyzed as in FIG. 1. The box represents the amine:phosphate ratio.

The ability of this delivery composition formulation to transduce normal cells was examined. The same delivery composition transduction conditions were then tested on Normal Human Bronchial Epithelial cells and Normal Human Bladder Urothelial cells (both differentiated and undifferentiated). The results from this analysis demonstrated that this delivery composition formulation produced little or no transduction on these cells, indicating some degree of specificity for transduction of tumor or rapidly dividing cells (FIG. 11).

To determine if incubation of the delivery composition with this mixed cell population would result in any degree of specific transduction of the tumor cells versus the normal bladder cells, UC14 cancer cells were combined with normal bladder urothelial cells that were allowed to differentiate. The PEI:DNA delivery composition (formulation II) was incubated with either differentiated normal human bladder urothelial cells, bladder cancer cell line UC14, or differentiated normal human bladder urothelial cells that were co-plated with the bladder cancer cell line UC14. When delivery composition was incubated with these cells, only the bladder tumor cells, which have a different morphology than the normal cells, demonstrated transduction.

Figure 12:
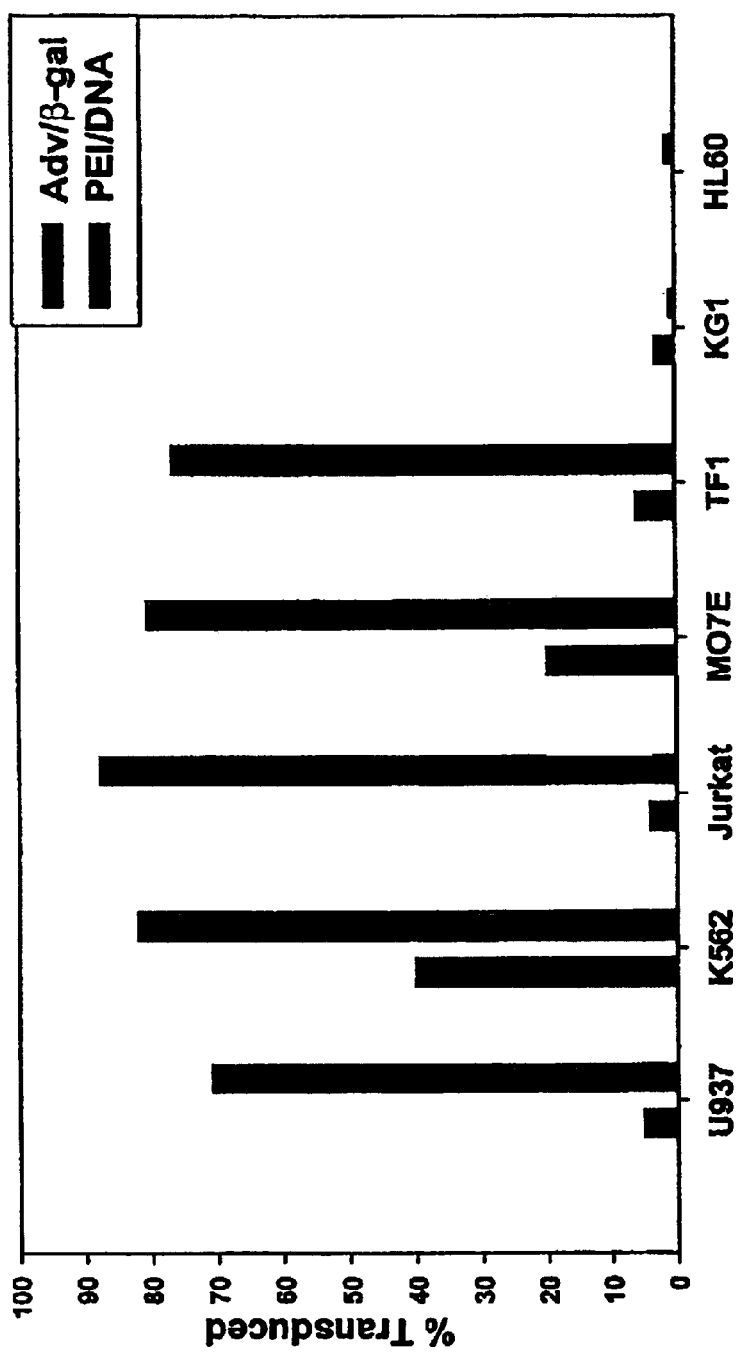
FIG. 12. Transduction analysis o leukemia cell lines with PEI:DNA delivery composition formulation II. Delivery composition was incubated with cells and transduction was analyzed as in FIG. 1.

In addition to testing the transduction of this delivery composition on attached cell lines, the ability of delivery composition formulation II to transduce cells that grow in suspension was examined. The cells were incubated with the construct composition ($1 \times 10^6$ cells incubated with 6 µg of delivery composition for 3 hrs.) and analyzed for transduction 72 hours after the initial delivery composition incubation. The cells were analyzed for β-gal expression using flow assisted cell sorting (FACS) analysis that measures the intensity of nucleic acid's expression on a per cell basis. The results of the analysis demonstrated that this delivery composition formulation (amine:phosphate ratio=2.7:1) could produce transduction efficiencies approaching 100% in five of the seven cell lines tested (FIG. 12). This was a surprising and striking finding in that these cells are very difficult to transduce at high levels by most if not all viral and non-viral delivery compositions. As a comparison, transduction of the same cell lines using a replication defective adenovirus carrying the β-gal gene under the control of the same promoter demonstrated transduction only as high as 40% in one cell line with little or no transduction in the other cell lines tested. The control on this vector is replication defective, E1 deleted adenovirus, carrying the beta-gal gene under the control of the CMV enhancer/promoter. This beta-gal gene is the same components used in the plasmid that was delivered by our PEI/DNA formulation in this study.

Figure 13B:
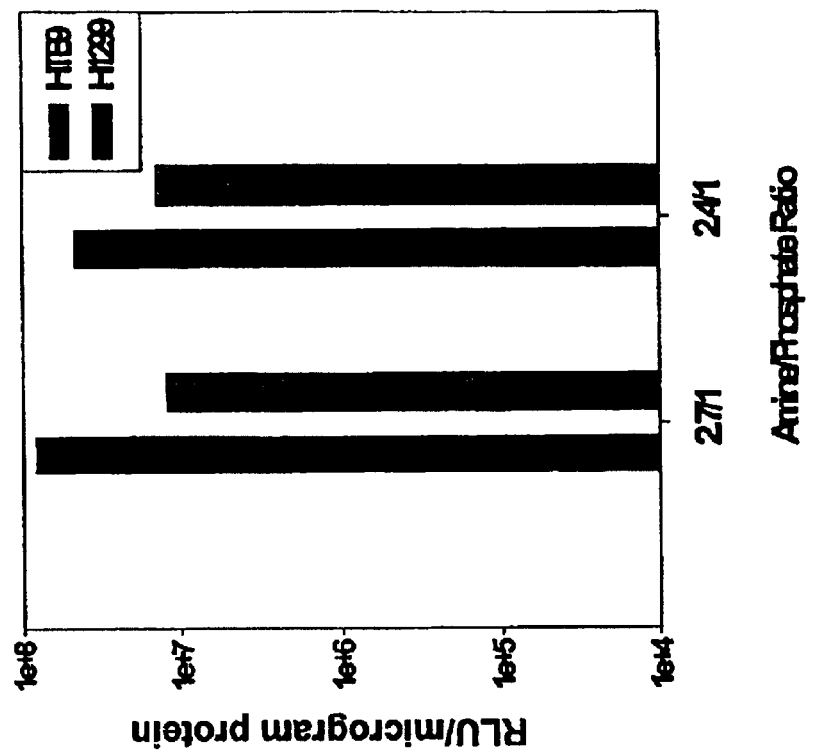
FIGS. 13A–13B. Quantitation of gene expression using the PEI:DNA delivery composition (2.5 µg) to transduce H1299 and HTB9 cells.
Figure 13A:
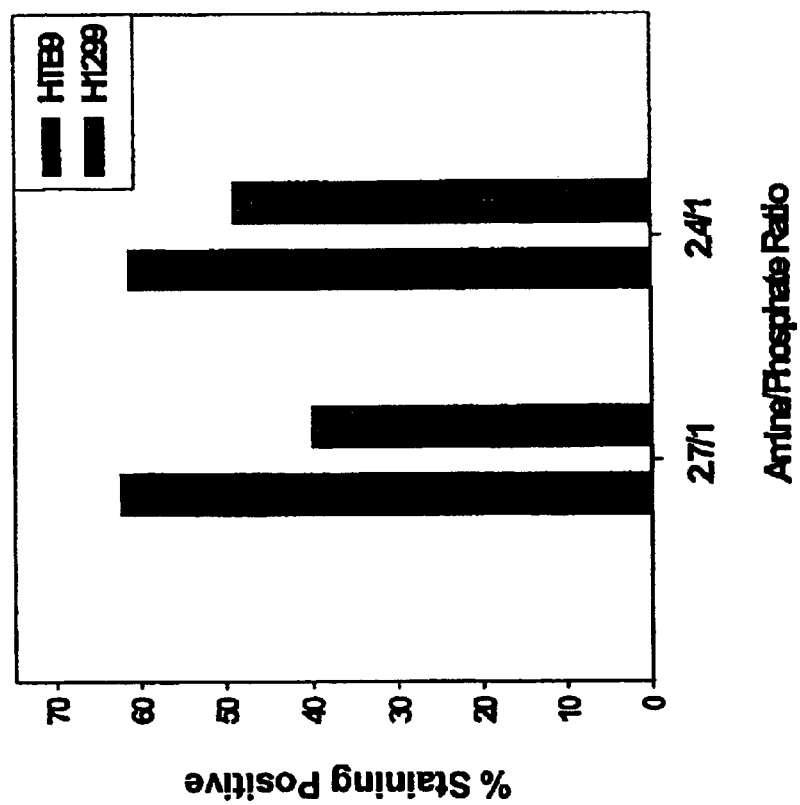

The transduction characteristics of this delivery composition formulation was then analyzed. The first step was to determine how much nucleic acid expression was actually correlated with the levels of transduction obtained. The delivery composition was delivered to the cell lines H1299 and HTB9. Twenty-four hours after the initial delivery composition incubation, the cells were either stained for β-gal expression or lysed and the amount of β-gal expression quantitated. Transduction as high as 40–60% was obtained with both cell lines and little difference occurred when an amine:phosphate ratio of 2.7:1 or 2.4:1 was used (FIG. 13A). In comparison, when β-gal expression was quantitated, expression as high as $10^{7-108}$ RLU/µg protein was obtained for both cell lines (FIG. 13B). This represents an extremely high level of protein expression, which is proportional to the amount of nucleic acid delivery in these cells. In comparison, most PEI delivery composition preparations in the literature have only obtained expression as high as $10^{6-107}$ RLU/µg protein, using luciferase as a reporter gene (Bousiff et al., 1995; Boussif et al., 1996; Densmore et al., 2000; Fronsdal et al., 2000; Boletta et al., 1997; Goula et al., 1998; Coll et al., 1999).

Example 3

Transduction Analysis in vitro Using Formula 3

Formulation II did produce intermittent precipitation of the delivery composition upon delivery composition formation with some subsequent DNA preparations and that other types of plasmids also produced intermittent precipitation even though each had been isolated using the published protocol. DNA isolated from Qiagen and Clontech kits may not be suitable, and is thus less preferred, for this particular delivery composition formulation based on toxicity studies. However, the previous lack of problems associated with DNA isolated with the new procedure and the large DNA yield lead to a reduced number of DNA isolations for DNA production. To further clarify the various embodiments, the exact variable or variables that were needed to form an efficient delivery composition, irrelevant of slight variabilities in DNA quality, was reexamined.

Figure 14B:
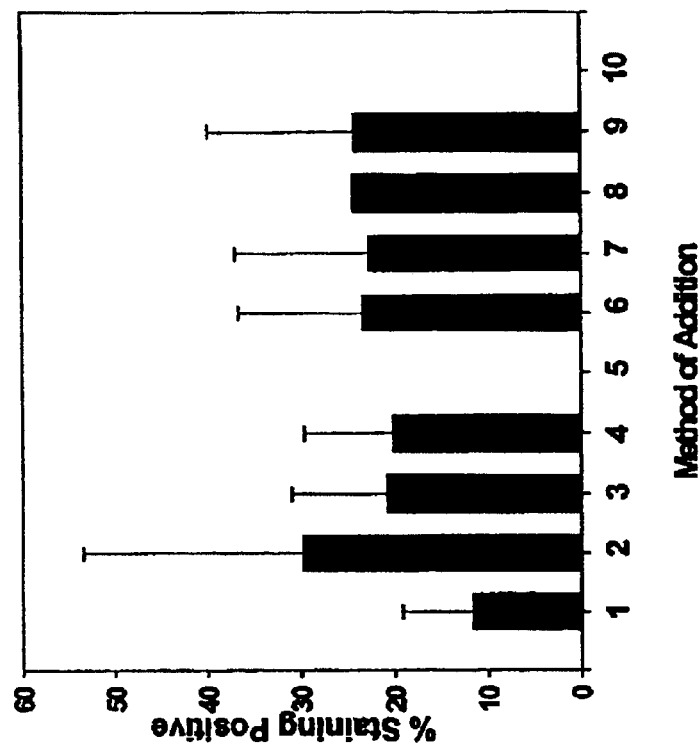
FIGS. 14A–14B. The determination of PEI:DNA delivery composition transduction variables using DNA isolated by Qiagen (FIG. 14A) or modified alkaline lysis isolation (FIG. 14B) protocols. Samples were combined by adding PEI (10 µl) to DNA (60 µl)(a/p=2.7/1) unless noted. Vectors were prepared, incubated with cells (2.5 µg DNA/well) for 3 hours, removed, and transduction was analyzed 24 hours later by histochemical staining for β-gal.
Figure 14A:
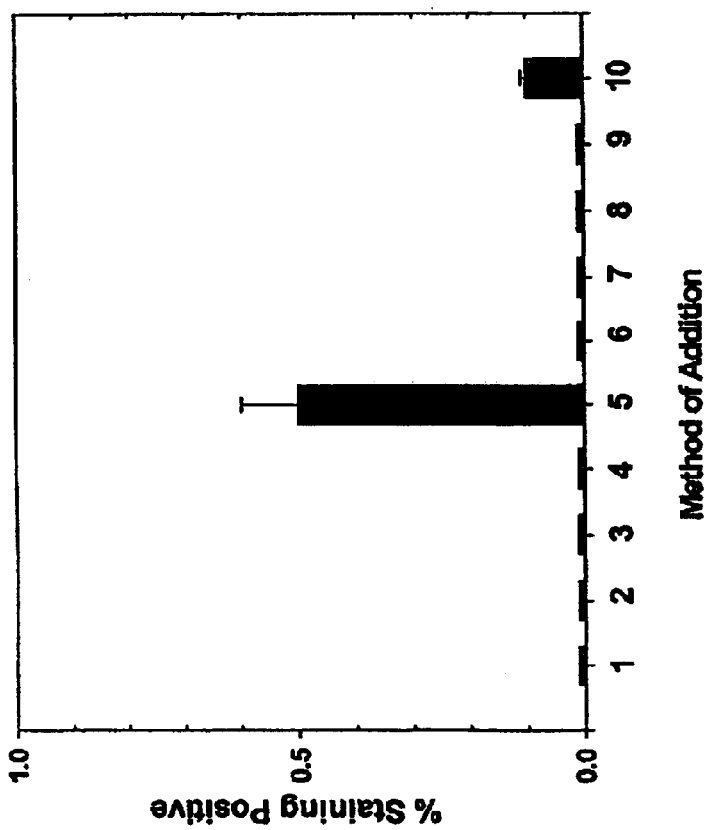

The DNA isolated by Qiagen was compared to the new procedure in the analysis. A total of 10 different methods were used to combine the delivery composition, using formulations I and II as a basis. Transduction on the cell line H1299 was done using PEI at an amine:phosphate ratio of 2.7:1 (FIGS. 14A and 14B). It was demonstrated that only very low levels of transduction could be obtained using the Qiagen DNA (FIG. 14B). Transduction only increased marginally when formulation I (FIG. 14, method 5) was used.

In complete contrast, very efficient transduction was obtained when the DNA isolated by the new procedure was used, but only when PEI in a small volume was added to DNA in a large volume formulation II (FIG. 14B). The importance of adding PEI in a small volume to DNA in a large volume was demonstrated when formulation I (which involved the addition of PEI to DNA in approximately equal volumes) was used for delivery composition preparation with the new DNA (FIG. 14B, method 5); little or no transduction resulted.

These studies demonstrate a surprising result that this method of combining PEI in a small volume with DNA, in combination with DNA isolated from the new DNA isolation procedure, produces an unexpectedly high level transduction.

In addition, a much more simplified method of producing the delivery composition could be used as outlined in FIG. 14, method 9, where neither vortexing nor the addition of PEI to DNA in a single drop was required. This delivery composition formulation is referred to as "Formulation III" and comprises the following:

Formulation m:

PEI in a small volume (10 μl, various concentrations) was added to DNA in a larger volume (60 μl, 6 μg), using a simple quick addition by pipeting PEI directly into the DNA solution with no vortexing or mixing.

Following this, the reaction was allowed to incubate for 2 to 5 minutes at room temperature and then added to cells (30 μl or 2.5 μg of DNA) in serum free media and incubated for 3 hours. The media containing delivery composition was then removed and replaced with media containing the correct FCS concentration.

Twenty-four hours after the initial delivery composition incubation, the cells were stained histochemically for β-gal expression and then the percentage of positive staining cells was determined 24 hours later.

Example 4

Transduction Analysis In Vivo

This example analyzes the in vivo nucleic acid delivery capabilities of the delivery composition formulations. Formulations I and II were used for the majority of the in vivo analyses. An intratumoral injection of delivery composition into a subcutaneous solid tumor generated in nude mice was used as an in vivo model. This model is clinically relevant as current gene therapy clinical trials to treat solid tumors use replication defective adenovirus administered by an intratumoral route into the tumor.

Initial studies to test the PEI:DNA delivery composition utilized formulation I (amine:phosphate ratio of 9:1) with Qiagen DNA. First, this delivery composition formulation was injected at a dose of 6 μg of DNA into a subcutaneous tumor generated with the non-small cell lung cancer cell line H1299. This resulted in little or no nucleic acid expression as determined by quantitation of β-gal expression using the Galactolite assay to measure active β-gal in tumor tissue homogenates.

Figure 15:
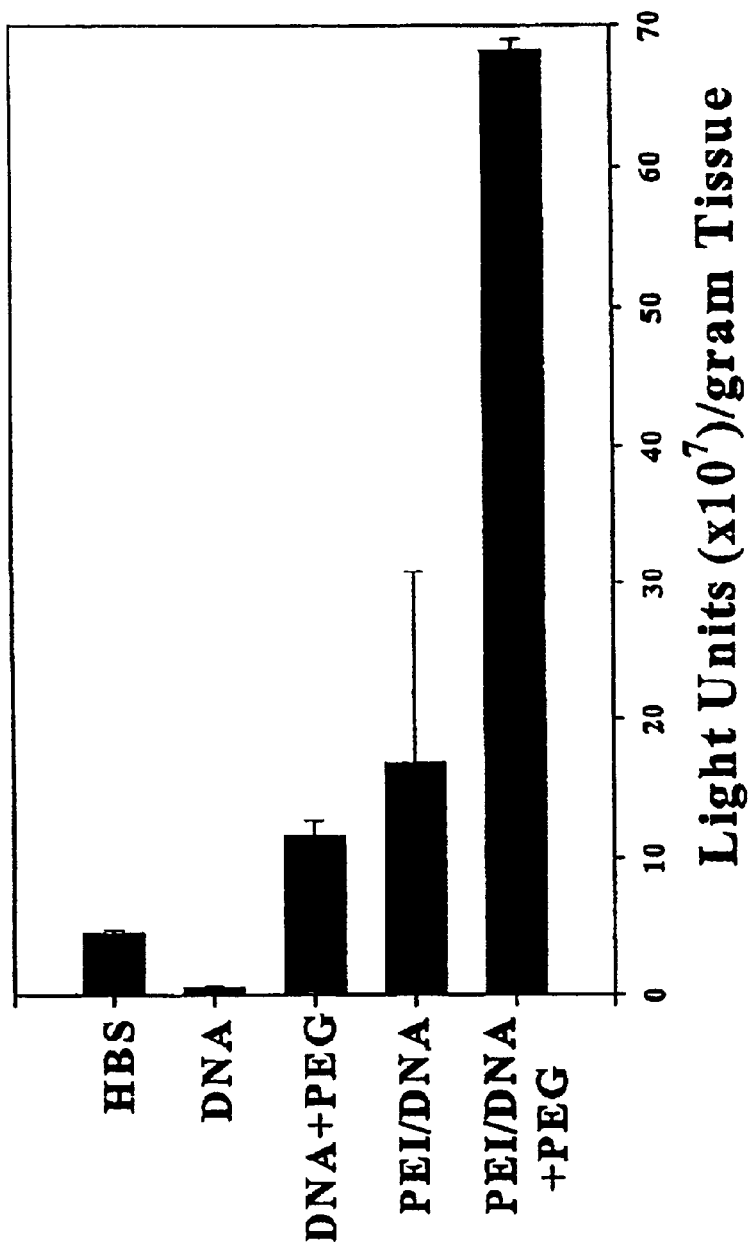
FIG. 15. Quantitation of β-gal expression following an intratumoral injection of PEI:DNA delivery composition formulation I at a dose of 120 µg of DNA.

Whether the amount of nucleic acid delivery (which should be proportional to the amount of nucleic acid expression) should be proportional to the dose was next examined, and whether a higher delivery composition dose would produce higher nucleic acid expression levels. Injection of the delivery composition at a dose of 120 μg of DNA increased nucleic acid expression, however this was marginally higher than DNA or tumor only (FIG. 15).

Whether transduction was being limited by the delivery compositions ability to pass throughout the tumor was then examined, and whether the combination of this delivery composition preparation with an agent that might enhance passage, resulting in higher levels of nucleic acid expression. Various agents ranging from different concentrations of NaCl to dextrose were tested. The addition of polyethylene glycol (PEG) to the delivery composition formulation that worked the best. When PEG was added to the delivery composition preparation to a final concentration of 8%, a >3-fold increase in nucleic acid expression resulted and significant levels of positive staining cells in tumor sections could be seen (FIG. 15). The addition of PEG to the formation resulted in a much more simplified method to increase transduction in vivo in this model. Other attempts to increase transduction have used infusion pumps that produce a marginal increase in transduction, as well as a much more complicated method for delivery composition administration (Coll et al., 1999).

There was a certain degree of toxicity following delivery composition administration. It was contemplated that several factors or combination of factors may contribute to this toxicity: the high amount of PEI used for delivery composition preparation (amine:phosphate ratio of 9:1), the high level of β-gal gene expression, and that the delivery composition preparations were being prepared in water and not a more "physiological appropriate" solution. To remedy this, the delivery composition preparation was changed in two ways: the delivery composition formulation was made in HEPES Buffer instead of water and in addition to adding PEG to the delivery composition following delivery composition formation, glucose was added to a final concentration of 5%. Both changes did not result in any detrimental affects on nucleic acid delivery by this delivery composition formulation, but actually resulted in decreased toxicity.

Figure 16:
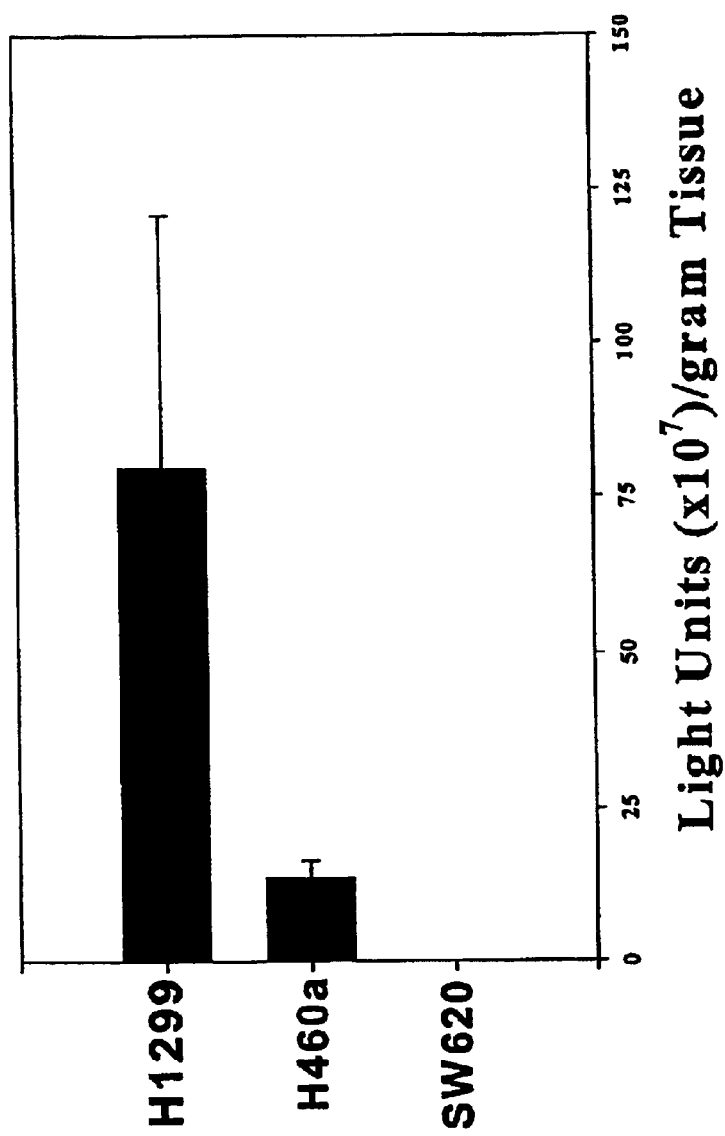
FIG. 16. A comparison of β-gal expression from tumors of different origins injected with PEI:DNA delivery composition formulation I at a dose of 120 µg of DNA.

In addition to testing the ability of this delivery composition preparation to mediate transduction in vivo with an H1299 subcutaneous tumor, the transduction in two other tumor types generated with the cell lines H460 (non-small cell lung cancer cell line) and SW620 (colon carcinoma cell line) was tested. Significant transduction occurred in both H1299 H460 tumors, however, little or no transduction was achieved in the SW620 tumors (FIG. 16).

Figure 17:
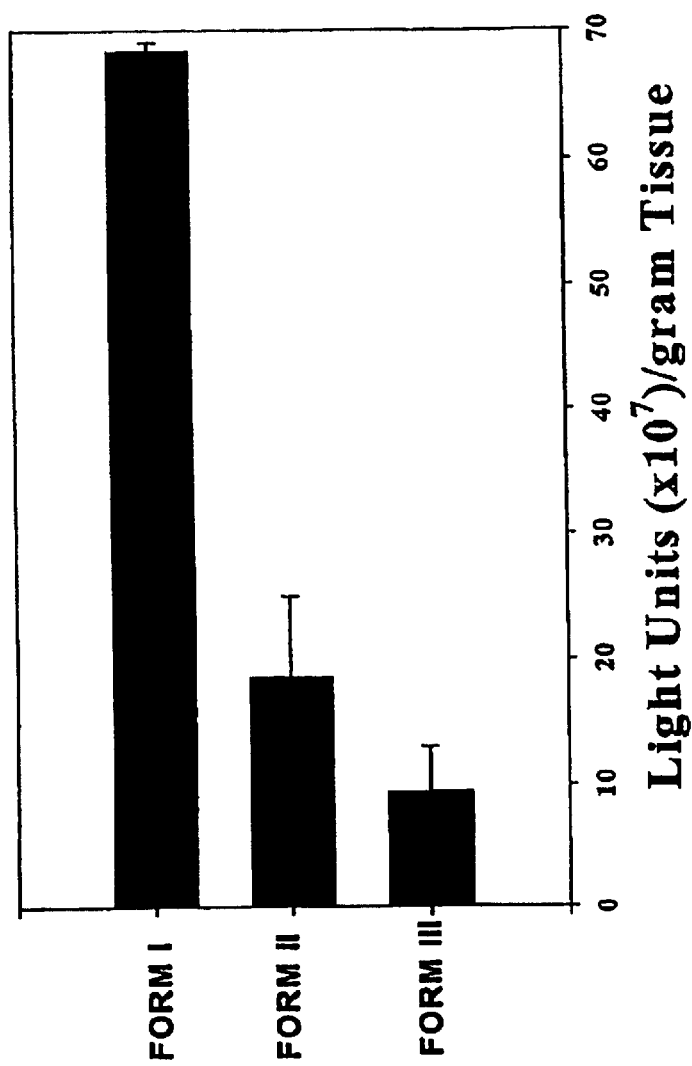
FIG. 17. A comparison of H1299 tumors injected with PEI:DNA delivery composition preparations using formulation I, II, or III. Formulation I involved the use of 120 µg of DNA, while formulation II and III used 6 µg of DNA (injected twice).

During the course of these studies, formulations II and III produced higher levels of transduction in vitro than formulation I. Based on this, formulations II and III were tested in vivo using the solid tumor model and compared transduction levels to the results from using formulations I. Intratumoral injections into H1299 subcutaneous tumors demonstrated that formulations II and III, using a dose of 6 μg DNA injected 2 times, produced almost results to formulation I which used a dose of 120 μg of DNA (FIG. 17). This was demonstrated by the fact that all formulations produced results almost similar to formulation I (β-gal levels in the range of $1 \times 10^8$ RLU/g tissue). It is contemplated that formulation II and III dose of the delivery composition may be increased, to obtain higher levels of nucleic acid transduction. However, with the amount of nucleic acid delivery obtained with formulation II, it is contemplated that enough nucleic acid expression should occur to mediate an effect using a therapeutic genetic construct.

Example 5

In Vitro Analysis of a Novel PEI/DNA Vector Formulation

Studies were carried out for the development of a non-viral vector formulation that is simple, affordable to prepare, and capable of highly efficient in vitro and in vivo gene delivery based on combining the polycation PEI with plasmid DNA. PEI (MW=25,000) was chosen based on its multi-functional ability to bind/compact DNA, serve as a point of ligand attachment, and most importantly, to perform endosome lysis. Initial studies using PEI as a delivery vector consisted of employing components and formulations that were described in published reports. The plasmid pCMV/β-gal (Cytomegalovirus enhancer/promoter driving E. coli β-galactosidase (β-gal) gene expression) was combined in equal volumes with PEI (125 μl DNA+125 μl PEI) at various charge ratio's and then incubated with a non-small cell lung cancer cell line (H1299) and three bladder cancer lines (UC14, BV, HTB9) to determine transduction efficiencies (FIG. 1).

Transduction as high as 33% was obtained with the cell line HTB9, while the rest exhibited maximum transduction between 10 and 20% at a/p ratio's between 4.3/1 and 9/1. This result is similar to reports in the literature, in that the highest level of transduction has been observed at these ratio's. Unfortunately, a/p ratio's in this range are also known to produce high cellular toxicity. An attempt was made to use higher a/p ratios (a/p up to 18) to increase transduction, but much higher toxicity was found to result. Most importantly, the results showed that there was no single concentration of PEI that could be used to produce high level transduction on every cell line. This significantly reduces the application of this published vector formulation in many in vitro and in vivo applications. Further, there would be no simple way to adjust the a/p ratio to obtain efficient tumor cell transduction from patient to patient. Based on the results, a more in-depth examination of the variables related to combining PEI and DNA was carried in order to the identification of a formulation with increased transduction, but lower toxicity.

The simplest method to lower toxicity would be to lower the a/p ratio, but this was found to result in reduced transduction when the current formulations have were used. The inventors hypothesized that the current method to combine PEI and DNA was not fully optimized. In order to take advantage of the self-assembling properties of the vector, the process for developing a formulation that will facilitate the production of vector with much greater gene delivery efficiency and lower toxicity was analyzed. Since the source of DNA may also contribute to toxicity, based on DNA purity, studies were also performed using plasmid DNA isolated by two different methods. The first source of DNA was isolated by a kit from Qiagen, which uses column chromatography to purify DNA. This kit is commonly used for isolating DNA that has been used by others in current PEI and nonviral vector formulations (FIG. 1). The second method utilized a modified alkaline lysis procedure in combination with proteinase K treatment of DNA to enhance DNA purity.

Following the isolation of the DNA using the two methods, endotoxin analysis was performed, indicating that while the DNA isolated by the modified alkaline lysis procedure was endotoxin free, the DNA isolated by the Qiagen kit contained endotoxin. After a further purification to remove endotoxin from the Qiagen DNA, both preparations of DNA were used to test PEI/DNA formulations at a/p ratios 2–3 times lower than published formulations (a/p=9/1). The studies described herein idicated that that when a small volume of PEI (10 μl) was added to DNA (isolated by modified alkaline lysis) in a larger volume (60 μl) (FIG. 1; samples 1–4, 6–9), efficient gene delivery was obtained at an a/p ratio of 2.7/1.

In comparison, current formulations descrinbed in the literature which utilize the addition of components in approximately equal volumes, did not demonstrate any significant transduction at this a/p ratio. This indicated that adding PEI to DNA in a much smaller volume contributed to enhancing gene delivery. To determine whether or not the source of DNA also contributed to this result, the same study was repeated but the DNA was changed to DNA isolated by the Qiagen kit (FIG. 14A). The only samples that produced transduction were 5 and 10, which were combined using the published procedure, but this was at levels less than 1%. To further confirm this observation, the new formulation (PEI (10 μl) added directly to DNA (60 μl) isolated by the modified alkaline lysis procedure) was tested on the same bladder and lung cancer cell lines using the same a/p ratios as outlined in FIG. 1. Gene delivery was found to occurr at levels as much as 4 times higher than previously obtained (FIG. 3). Most importantly, a single a/p ratio (2.7/1) produced the most efficient transduction in all of the cell lines tested.

Figure 20A:
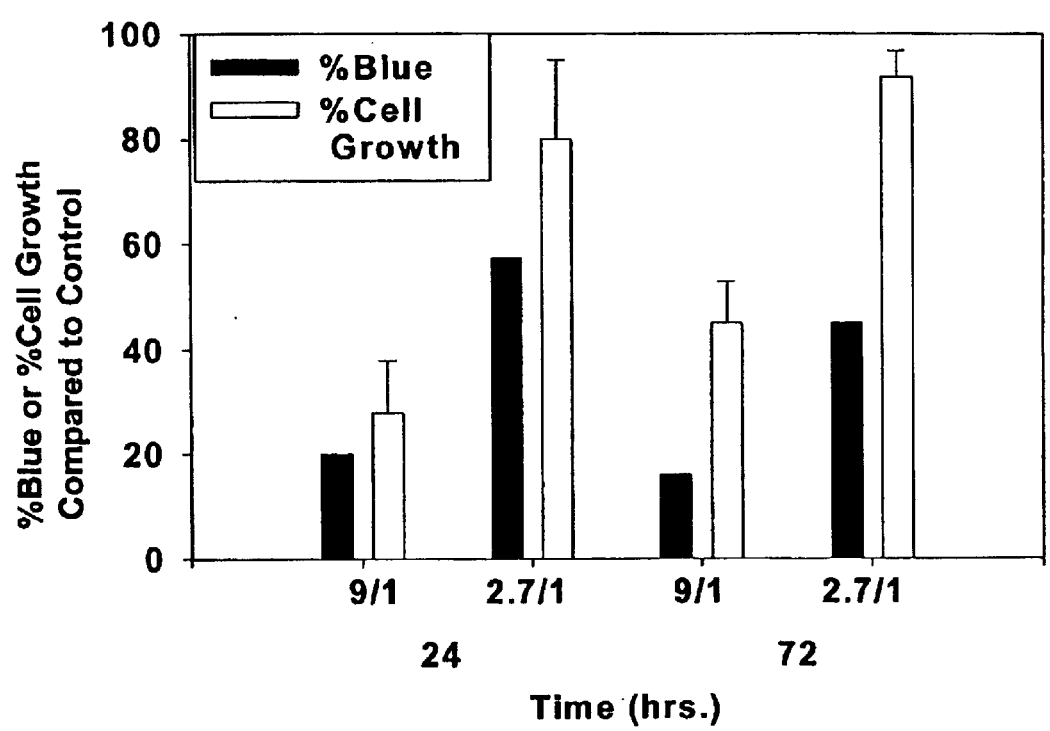
FIGS. 20A–20B. Analysis of toxicity on H1299 cells 24 and 72 hours after initial vector incubation (FIG. 20A) and β-gal expression on the cell lines H1299 and HTB9 (FIG. 20B), 24 hours after the initial incubation with the new vector formulation. Cells were transduced using conditions outlined in FIG. 1.
Figure 20B:
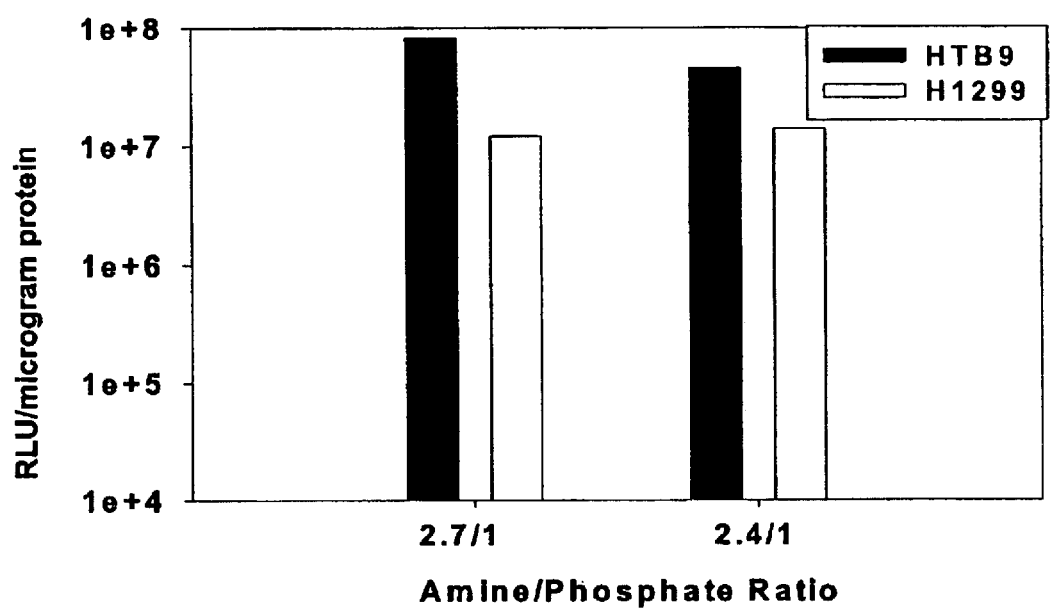

At the concentration of PEI that was analyzed, which is more than 3 times lower than amounts used in published formulations, it was expected that the amount of toxicity to cells would be low. To confirm this, the cell line H1299 was tested for transduction (stain/count) and toxicity (by cell counts) 24 and 72 hours after initial transduction (FIG. 20A). While there was a 20% reduction in cell number after 24 hours, little or no toxicity was noted at 72 hours even when transduction efficiencies as high as 40–60% were obtained (FIG. 20A). In comparison, transduction using the published formulation resulted in a significant reduction in cell growth and transduction only as high as 20% at both 24 and 72 hours after the initial incubation with vector. In the context of the new formulation, it was hypothesized that this toxicity could be due to high-level βgal expression, as this protein has been identified to be toxic when expressed at high levels. To confirm this, the amount of βgal expression in these cells was determined. When H1299 and HTB9 cells were transduced with the vector and gene expression was assayed 24 hours later, βgal levels as high as $10^7$ to $10^8$ RLU/μg protein were obtained with transduction as high as 40–60% (FIG. 20AB). This level of expression is a log higher than levels obtained using other published PEI based vector formulations.

The novel PEI/DNA vector formulation was then used to determine whether efficient transduction could be obtained on a variety of different cell lines as well as normal cells. Vector formulations were prepared using the new formulation (a/p ratio of 2.7/1) and incubated with cancer cell lines from bladder (UC2, UC10, UC13, HTB-9, BVR), lung (H1299, H358), breast (MCF-7, MB231), prostate (PC3, LnCap), and leukemia (MO7E, K562) cell lines, as well as normal cells (Normal Human Bronchial Epithelial Cells (NHBE), Normal Bladder Urothelial Cells, undifferentiated (NBUN) and differentiated (NBDIF) (FIG. 21).

Figure 21:
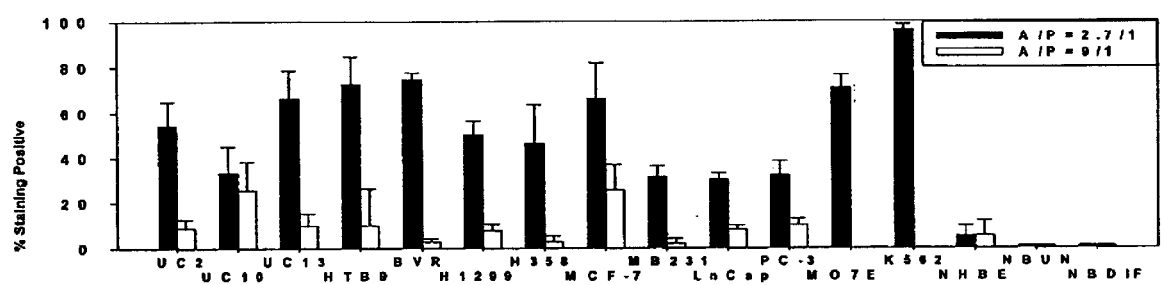
FIG. 21. Transduction analysis of cancer cell lines and normal cells using the new PEI/DNA vector formulation. Cells were transduced using conditions outlined in FIG. 1.

Transduction efficiencies ranging from as low as 24% to as high as 99% were obtained with the new formulation, which were as much as 100 times higher than the same cell lines transduced with vector made using the published procedure at an a/p ratio of 9/1 (FIG. 21). It was also interesting to note that the incubation of the new vector with the leukemia cell lines produced transduction at levels as high as 99%. This is a striking finding in that these cells are very difficult to transduce at any level by most, if not all, viral and non-viral vectors. As a comparison, transduction of the leukemia cell lines using a replication defective adenovirus carrying the βgal gene under the control of the same promoter demonstrated little or no transduction.

It can be anticipated that, as the transduction conditions for each type of cell line described herein were the same, and optimization of transduction such as incubation time, dose of vector, etc. was not carried out, further optimization of transduction conditions should lead to higher levels of gene delivery. The simple, self-assembling nature of the vector should allow any user to perform simple changes to these variables to optimize transduction. In addition, it should also be noted that the determination of transduction described above was based on βgal staining, which has been identified to severely underestimate the amount of transduced cells by as much as seventy percent. As a result, in many instances, the percentage of transduced cells described was probably much higher than the calculated number. Transduction of normal cell lines was also analyzed to develop an initial idea of possible non-specific interaction with normal cells. The same transduction conditions were tested on Normal Human Bronchial Epithelial cells and Normal Human Bladder Urothelial cells (both differentiated and undifferentiated).

The results from this analysis demonstrated that the new vector formulation produced little or no transduction on these cells, indicating some degree of specificity for transduction of tumor or rapidly dividing cells (FIG. 21).

Example 6

Analysis of the PEI/DNA Vector Formulation In Vivo

Studies were also directed towards analyzing the in vivo gene delivery capabilities of the novel vector formulation. The initial studies utilized a simple model involving an intratumoral injection of vector into a subcutaneous solid tumor generated in nude mice. This procedure/model is clinically relevant as current gene therapy clinical trials designed to treat solid tumors use replication defective adenovirus administered by an intratumoral route. In the initial studies to test the PEI/DNA vector formulation, only DNA was injected at a dose of 6 µg into a subcutaneous tumor generated with the NSCLC cell line H1299. This resulted in little or no gene expression as determined by quantitation of βgal gene expression using the Galactolite assay to measure active βgal in tumor tissue homogenates (FIG. 15).

The new PEI/DNA vector formulation was then injected at the same dose. A >10-fold increase in gene expression resulted, but this level was still lower than reports in the literature, which have obtained >$10^8$ RLU/g tissue when PEI/DNA vector formulations were slowly infused directly into tumors. To address this issue, it was hypothesized that the vector must be limited by its ability to pass throughout the tumor and that combining the vector formulation with an agent that enhances dissemination in the tumor would result in higher levels of gene delivery and expression. Various agents were tested, ranging from different concentrations of NaCl to dextrose. However, it was the addition of polyethylene glycol (PEG) to the vector formulation that was found to function the best. When PEG was added to the vector preparation to a final concentration of 8%, a >3-fold increase in gene expression over the PEI/DNA vector and an over 30-fold increase in gene expression over DNA alone resulted (FIG. 15). The addition of PEG to the formulation also resulted in significant levels of positive staining cells in sections from vector injected tumors. The ability of PEG to enhance transduction by the new vector formulation represents a much more simplified method to increase transduction in this model. Other attempts to increase transduction have used complicated methods for vector administration using infusion pumps to decrease the rate of vector administration, but this produces only a marginal increase. In addition to allowing for rapid vector administration, the results described herein provide a basis for further investigating the direct attachment of PEG to the vector. It is contemplated that if PEG is directly attached to the PEI/DNA vector, then increased transduction will result as well as providing a new attachment point for targeting ligands.

Figure 22:
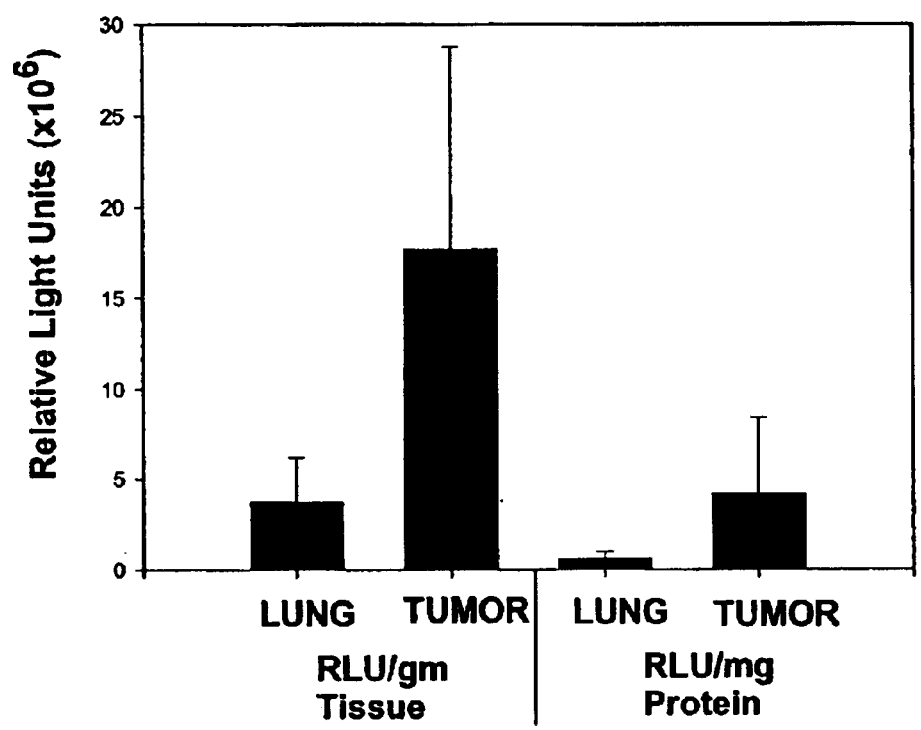
FIG. 22. Quantitation of β-gal expression in tumor and lung from H1299 tumor bearing mice injected intravenously with the PEI/DNA vector. Results were determined either on a per gram tissue or per milligram protein basis.

In addition to testing vector administration by an intratumoral route, vector administration by an intravenous route was also tested in animals bearing subcutaneous tumors. These experiments were designed to create a baseline for comparing tissue deposition of non-targeted PEIDNA vector to targeted vector. The PEI/DNA vector (dose=6 µg DNA) plus PEG was injected via the tail vein into mice bearing a single subcutaneous H1299 tumor. Twenty-four hours following a single injection, the tumor and lung were removed from animals and frozen. Analysis of βgal expression in homogenates of equal amounts of tissue showed significantly more expression in tumor than lung (FIG. 22). To ensure that equal amounts were analyzed, expression was also corrected based on protein quantitation. This still demonstrated that greater gene expression occurred in tumor than lung.

This surprising result allowed testing of the hypothesis that if a tumor specific ligand is attached to the PEI/DNA vector, then an even greater degree of tumor specific uptake of vector should occur. In addition, the results obtained for both routes of administration indicate that if a PEI/DNA vector carrying the p53 gene were administered by these routes, then gene expression might be sufficiently high to elicit an antitumor affect.

Example 7

Analysis of PEI/DNA Vector Mediated Delivery of the P53 Gene

To test the delivery efficiency of the new PEI/DNA vector formulations in the context of a therapeutic gene, studies were initiated using the p53 tumor suppressor gene. This gene is commonly mutated in lung cancer and metastatic cells and is a good choice for developing a gene therapy approach to treat lung cancer. To initiate testing of the ability of the new vector formulation to deliver the p53 gene, it was first determined whether the current vector formulation at an a/p ratio of 2.7/1 was appropriate for delivering the p53 expressing plasmid since this plasmid is larger than the pCMVβ-gal plasmid (7 kb). This 11.7 kb plasmid has the p53 gene under the control of the CMV enhancer/promoter. The new vector formulation was produced at a/p ratios ranging from 9/1 down to 2.4/1 to transduce H1299 cells, which have deleted p53 expression. Twenty-four hours after the initial incubation, the cells were collected, lysed, and then cell lysates were electrophoresed on an SDS-PAGE gel, transferred to a membrane and then probed with either the p53 specific antibody 1801 or a β-actin specific antibody (to serve as loading control). Lysates from non-treated H1299 cells and from the cell line UC14 served as a negative and positive control (size marker) respectively for p53. Low-level p53 expression was observed with vector made at an a/p ratio of 7.5/1; however, the amount of p53 expression increased to maximum levels when an a/p ratio of 2.7/1 was used.

Based on these results, it was indictaed that the formulation at an a/p ratio of 2.7/1 could be used to efficiently deliver the p53 gene. To ensure that high level p53 expression was occurring in the tumor cells prior to performing tumor growth experiments in animals, the PEI/DNA vector at an a/p ratio=2.7/1 was incubated with H1299 cells and then fixed 24 hours following transduction. The cells were then analyzed by immunohistochemistry (using ab 1801) to determine p53 expression. Significant levels of p53 positive cells were identified in comparison to control cells. Based on the western and in vitro data, it was then possible to test whether this level of gene expression/delivery had an effect on tumor growth in an animal model.

Figure 18A:
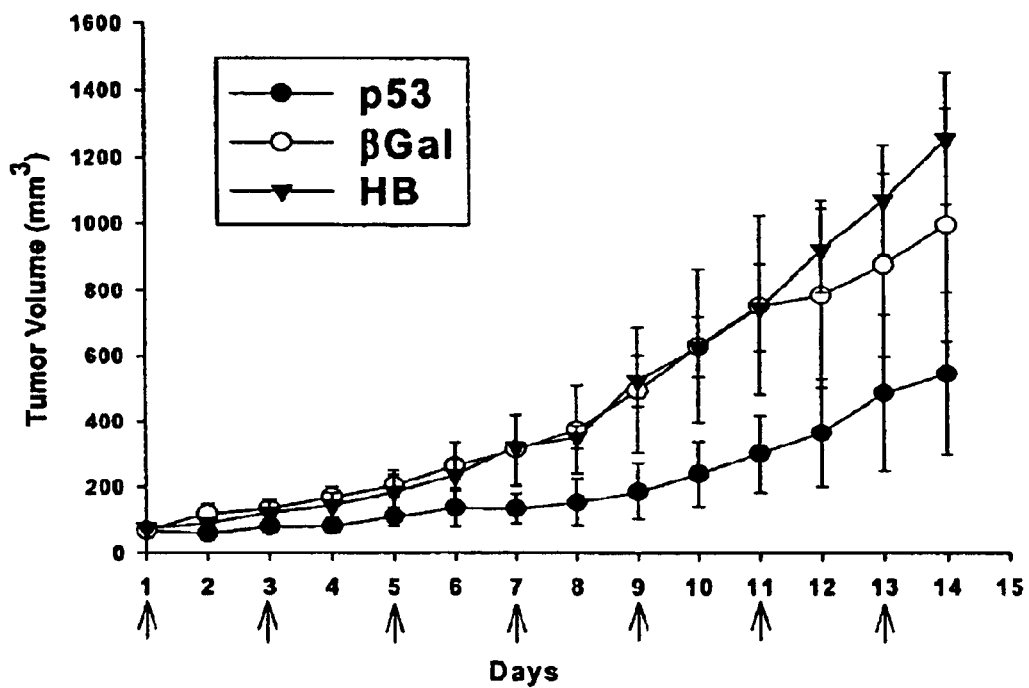
FIGS. 18A–18B. Analysis of the affect of p53 gene expression on H1299 (-p53) tumor growth following injections of PEI:DNA delivery composition formulation II by either intratumoral (FIG. 18A) or intravenous (FIG. 18B) injection. Injections (with either HEPES Buffer, p53 plasmid, or β-gal plasmid) were performed every other day for 2 weeks at a dose of 6 µg DNA/injection×2.

To test this formulation, subcutaneous tumors (5 mm in size) generated with the cell line H1299 were initially injected with the PEI/DNA vector using the vector formulation at a dose of 6 µg of DNA per injection in two directions for a total dose of 12 µg DNA. A transient inhibition of tumor growth occurred for 1–3 days as compared to control treated tumors (non-treated or treated with a vector carrying the pCMVβ-gal plasmid at a dose of 12 µg DNA). Based on this observation, it was hypothesized that if multiple injections of the vector were made at 2 day intervals, the growth of the tumors should be greatly reduced in comparison to control treated tumors. To test this, the vector was injected at a dose of 6 µg/injection in two directions (total dose=12 µg) every other day for a total of 7 injections over 14 days. Tumor growth was greatly reduced and in some instances regressed after the initial few injections were made and this inhibition could be maintained during the majority of the study (FIG. 18A). There was found to be a slight increase in tumor size during the second week of injections and since the vector dose was not correspondingly increased, tumor growth accelerated. Overall however, the results of the studies indicated that the vector could be used to deliver a therapeutic gene containing plasmid and that p53 was expressed at sufficient levels to inhibit tumor cell growth, albeit transiently. More importantly, there was little or no indication of vector related toxicity during the course of the experiment even when 7 injections were performed.

Figure 18B:
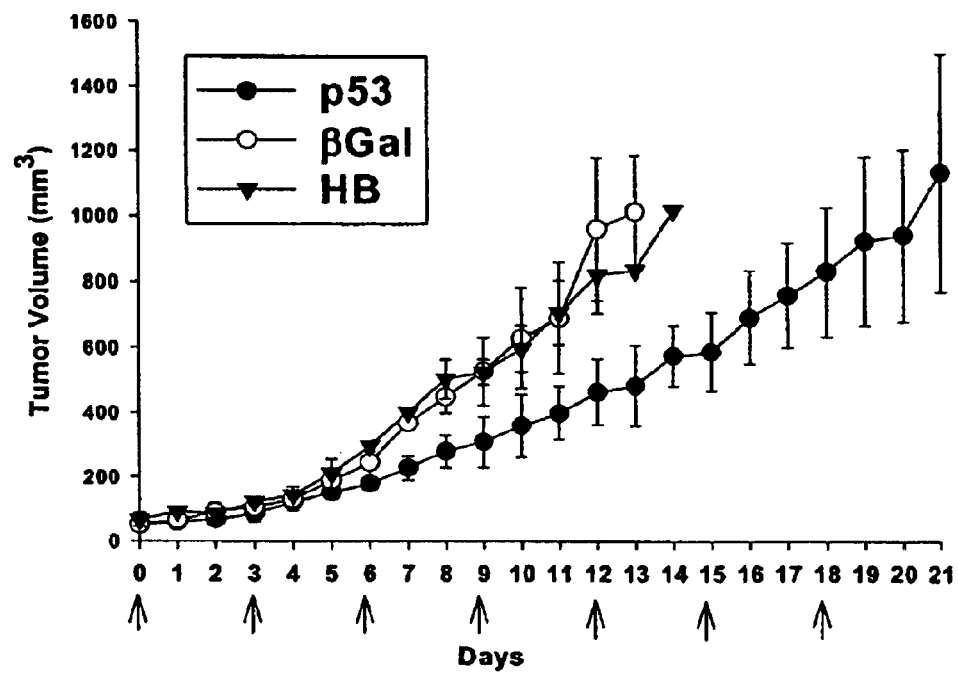
Figure 23:
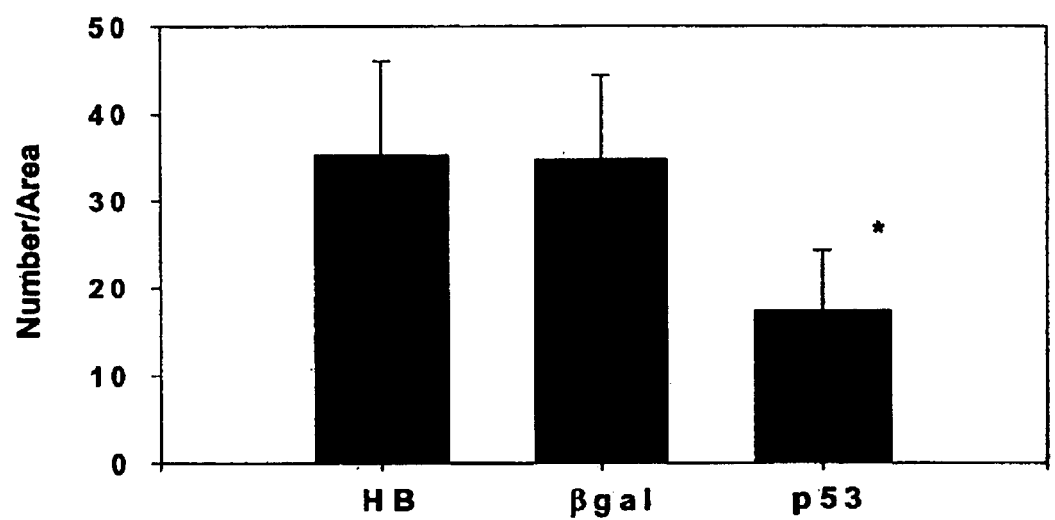
FIG. 23. Analysis of micro-vessel (MVD) density in H1299 tumors following p53 delivery. A total of 2 samples (5 areas per sample) were analyzed to determine MVD. *p>0.001p53 vs. HB or β-gal.

It was reasoned that if tumor growth inhibition could be obtained via an intratumoral administration, then an intravenous administration may result in growth inhibition as well. Therefore, the p53 gene-containing vector was administered via the tail vein every three days to H1299 tumor bearing animals. This interval was chosen as the minimal amount of time to allow for the vein to recover from the injection. When vector was administered intravenously every three days for a period of 21 days, a >40% reduction in tumor size occurred (FIG. 18B). It was hypothesized that p53 was affecting tumor growth through either inducing growth arrest, apoptosis, antiangiogenesis, or some combination of these affects. The tumors from animals treated with the p53 gene-containing vector demonstrated significantly less blood vessel formation than tumor treated with HEPES Buffer or βgal gene containing vector (FIG. 23). To further confirm this antiangiogenic affect, tumor sections were also stained for VEGF expression. While control treated animals demonstrated high level VEGF expression, those animals treated with p53 gene containing vector demonstrated little or no VEGF staining. These tumors are being analyzed further.

Example 8

Targeting of the Novel PEI/DNA Vector Formulation

In addition to analyzing the "generic" or non-targeted PEI/DNA vector formulation, studies were also pursued to target this vector. As the vector formulations were new, the affect of the addition of targeting ligands to the vector on vector integrity and other characteristics such as vector charge, size, and gene delivery efficiency was unknown. It was hypothesized that if a vector formulation containing all appropriate components and a targeting ligand was correctly formulated, then efficient and specific gene delivery would be obtained. EGF was chosen as a targeting ligand and the EGF receptor was chosen for targeting, as this receptor is over-expressed on many types of tumor cells such as in lung tumors and metastasis, and also based on the fact that the small peptide nature of EGF should allow easy manipulation for coupling.

Initial studies using epidermal growth factor (EGF) to target the vector to tumor cells were not promising. The direct attachment of EGF to the PEIDNA vector demonstrated no increase in specific gene delivery. It was hypothesized that the close proximity of EGF to the vector causes steric hindrance and inefficient interactions between EGF and EGFr. It may also be that the high, general gene delivery efficiency of the generic vector formulations may be too difficult to overcome. To address these limiting factors, a biotinylated form of PEI that has one biotin per PEI molecule was used. This would allow the attachment of an anti-biotin antibody to the vector that would serve several purposes: (1) a FITC labeled version of the antibody would allow attachment of a FITC label to the vector and thus vector visualization in future delivery studies to determine the nature of gene delivery associated with this vector, (2) the antibody could serve as a simple point of attachment for the ligand by chemically attaching EGF to the antibody and reducing steric hindrance in relation to the vector, and (3) the antibody could be used to not only stabilize the vector but also decrease the non-specific interaction of the vector with the cells, resulting in increased, targeted gene delivery by the vector. In addition to labeling the PEI with FITC, the PEI/DNA vector formulation containing a Rhodamine tagged plasmid has been tested. This was attached to the plasmid using a peptide nucleic acid purchased from Gene Therapy Systems (California). The presence of both of these tags in the vector will allow initiation of studies to determine vector localization in the cell as well as the gene delivery mechanism behind the nontargeted and targeted versions of the vector.

Figure 24A:
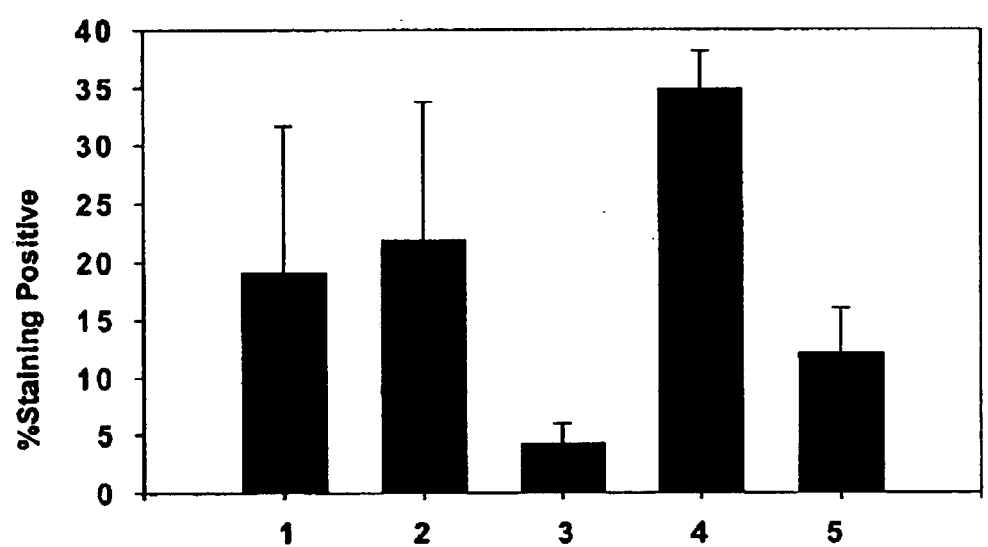
FIGS. 24A, B. Targeting of the PEI/DNA vector (2.5 µg) formulation through EGF attachment. The cell lines H1299 (FIG. 24A) and A549 (FIG. 24B) were incubated with the following: 1) PEI/DNA vector, 2) B-PEI/DNA vector, 3)
Figure 24B:
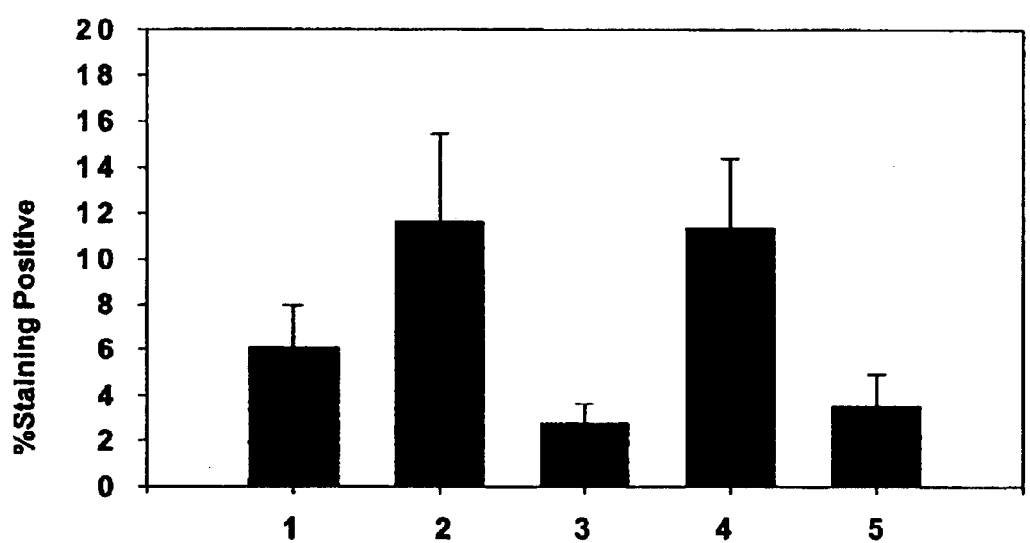

To test the targetability of the EGF/PEI/DNA vector, various vector combinations were incubated with H1299 and A549 cells (both Non-Small Cell Lung Cancer cell lines). Incubation of cells with either PEI/DNA of Biotin-PEI/DNA resulted in normal levels of transduction, while the addition of the anti-biotin antibody to the vector formulation resulted in a sharp decrease in gene delivery on both cell lines (FIGS. 24A–24B). Interestingly, when the EGF attached antibiotin antibody was incubated with the cells, transduction increased back to original levels and even higher. While this may reflect a change in vector charge due to the presence of EGF on the antibody or just an increase in non-specific vector interaction with the cells, gene delivery specificity was tested by co-incubating the targeted vector with a 100-fold molar excess of EGF (FIGS. 24A–24B). This resulted in a reduction in transduction back to levels achieved with PEI/DNA or B-PEI/DNA vectors. These studies provide strong evidence that there is a basis for developing the vector formulation as a targeted vector and can now be used as a starting point to further optimize targeted gene delivery by this vector.

Example 9

Analysis of PEI/DNA Vector Mediated Delivery of the P53 Gene in an Orthotopic Bladder Tumor Model A preliminary experiment was carried out to assess the ability of the novel non-targetedPEI/DNA vector formulation to deliver the p53 gene to the bladder tumor cell line UC3 in the context of an orthotopic tumor model. Transduction was already tested with this cell line, with observed transduction as high as 56%. The UC3 cell line also is "null for p53 expression," although some studies have shown low level expression, making it a good choice for p53 gene therapy studies. In the experiment to test the ability of the PEI/DNA vector carrying the p53 gene to inhibit tumor growth, 50,000 UC3 tumor cells were injected into the outer bladder wall of 30 nude mice. Four days later, the animals were randomized into three groups of ten animals, with one group receiving an intravenous administration of HEPES Buffer (HB), the second group receiving 6 µg of the PEI/

DNA vector carrying the βgal gene under the control of the CMV enhancer/promoter, and the third group receiving 6 μg of the PEI/DNA vector carrying the p53 gene under the control of the same promoter. These same injections were then performed every three days for a period of three weeks, at which time, the animals were euthanized and the bladders with tumors were removed and weighed. The total weight of the bladder (with tumor) was measured, since tumor removal was too difficult due to tumor invasion into the bladder. When the weights of the bladder/tumors were compared between the HB and PEI/DNA-βgal treated groups, no difference was observed (FIG. 25). In contrast, a 70% reduction in tumor weight was observed in the PEI/DNA-p53 group as compared to either the HB or PEI/DNA-βgal injected groups (FIG. 25).

This result confirms the findings observed using the intravenous route of administration of vector to animals bearing subcutaneous solid tumors, indicating that the novel PEI/DNA vector formulation is mediating gene delivery to orthotopic bladder tumors following an intravenous administration. The bladder/tumors as well as the lungs, liver, and kidney are now being examined in these animals to determine the level and location of βgal expression using βgal quantitation and RT-PCR (βgal specific primers). Also, analysis is being done of tumor specific changes in p53 and p21 expression, as well as changes in VEGF (angiogenesis), CD31 (angiogenesis), and TUNEL staining (apoptosis). The results of this study will allow further pursuit of the analysis of the delivery mechanism associated with this novel vector as well as improving the delivery mediated by this vector through targeting.

Example 10

Further Analyses of the PEI/DNA Vector

Further analysis of aspects of the vector formulation were contemnplated by the inventors as follows:

1) Analyze vector localization in the animal by PCR, reverse transcriptase PCR and β-gal expression quantitation in tumor, blood, lung, liver, and kidney. These studies are designed to determine vector localization in these organs and tumor as it relates to half-life in the blood versus tissue deposition. Determinatyion is also made whether the inclusion of polyethylene glycol into the formulation increases the half-life of the vector in vivo.

2) Determine the affect of therapeutic gene expression in tumors. Analysis is carried out for changes in p53 and p21 expression in the animals bearing H1299 tumors to determine the level and duration of expression in tumors. These studies will be correlated with apoptosis analysis (TUNEL assay) to determine the affect of p53 expression on inducing this pathway.

3) Develop the interaction between PDBA and SHA as a simple means to link ligands to the vector that will ensure vector integrity, but at the same time increase gene delivery specificity.

4) Continue studies to use fluorescently labeled vector to determine the mechanism of gene delivery into both high and low transduced cells.

5) Further analyze the transduction characteristics of the PEI/DNA vector based on use of DNA isolated from the modified alkaline lysis procedure and the Qiagen method. It is contamplated that the purity of the DNA contributes to the ability to form efficient vector using the novel method of vector formulation.

6) Determine vector characteristics based on particle charge and particle size and correlate these variables with in vitro and in vivo transduction efficiencies.

7) Analyze the ability of the PEI/DNA vector to deliver other therapeutic genes such as the Herpes Simplex Thymidine Kinase gene.

Example 11

Therapeutic Genetic Construct Delivery In Vitro and In Vivo

The ability of the delivery composition formulations to deliver a genetic construct comprising the p53 gene (Spitz et al., 1996; Spitz et al., 1996; Nguyen et al., 1996; Nguyen et al., 1997), and its affect on tumor cell growth was examined. First, it was determined whether formulation II using amine:phosphate ratio of 2.7:1 was appropriate for delivering the p53 expressing plasmid since this plasmid is larger than the pCMVβ-gal plasmid (7 kb). This 11.7 kb plasmid has the p53 gene under the control of the CMV enhancer/promoter. The delivery composition formulation II were used and produced delivery composition at amine:phosphate ratios ranging from 9:1 to 2.4:1.

Twenty-four hours after the initial incubation, the cells were collected, lysed, and then cell lysates were electrophoresed on an SDS PAGE gel, transferred to a membrane and then probed with either the p53 specific antibody 1801, or a β-actin specific antibody to detect β-actin levels which served as a loading control. A lysate from non-treated H1299 cells, which are deleted for p53, served as a negative control, while a lysate from the cell line UC14 served as a positive control/size marker for p53.

H1299 cells are deleted for p53 expression while UC14 express normal p53. Western blot analysis of p53 expression following p53 gene delivery into H1299 tumor cells using PEI:DNA delivery composition formulation II demonstrated low-level p53 expression with delivery composition made at an amine:phosphate ratio of 7.5:1; however, the amount of p53 expression increased to maximum levels when an amine:phosphate ratio of 2.7:1 was used. These results demonstrate that formulation II at an amine:phosphate ratio of 2.7:1 could be used to efficiently deliver the p53 gene.

The examine whether this level of nucleic acid expression/delivery had an effect on tumor growth in an animal model, subcutaneous tumors (5 mm in size) generated with the cell line H1299 were injected with the PEI:DNA delivery composition using formulation II/PEG/Dex at a dose of 6 μg of DNA per injection. A transient inhibition of tumor growth occurred for 1 to 3 days as compared to control treated tumors (non-treated or treated with a delivery composition carrying the pCMVβ-gal plasmid at a dose of 6 μg DNA). Irrelevant of how the delivery composition was injected, the maximum affect on tumor growth inhibition was about 1 to 3 days.

It was contemplated that multiple injections of the delivery composition made at 2 day intervals may greatly reduce the growth of the tumors in comparison to control treated tumors. The delivery composition was injected at a dose of 6 μg/injection in two directions (e.g., injections made by inserting the second needle into the tumor at a 90 degree angle from the first injected needle, total dose=12 μg) every other day for a total of 7 injections over 14 days. Tumor growth was greatly reduced and in some instances regressed after the initial few injections were made and this inhibition could be maintained during the majority of the study (FIG. 18). There was a slight increase in tumor size during the second week of injections and since the delivery composition dose was not correspondingly increased, tumor growth accelerated. Overall though, these results demonstrate that this delivery composition could be used to deliver a therapeutic nucleic acid containing plasmid and that p53 was expressed at sufficient levels to inhibit tumor cell growth. More importantly, there was little or no indication of delivery composition related toxicity during the course of the study even when 7 injections were performed. It is contemplated that other formulations described herein, particularly formulation III, will allow higher doses of the delivery composition to be injected to produce an improved affect on inhibiting tumor growth.

Example 12

PEI:DNA Delivery Composition Targeting

In addition to developing the PEI:DNA delivery composition formulations as "generic" delivery compositions that are not targeted and capable of nucleic acid delivery to many different cell types, it was contemplated that a targeting agent may be added to the composition. It was contemplated a targeting ligand may improve efficient and specific delivery of a genetic construct to a target cell.

Since these are new and unique delivery composition formulations, the addition of a targeting ligand to the delivery composition affect on delivery composition integrity and other delivery composition characteristics such as delivery composition charge, size, and nucleic acid delivery efficiency was examined for some targeting agents. EGF was chosen as a targeting ligand to the EGF receptor. This receptor is over-expressed on many types of tumor cells such as in breast and bladder tumors. The small peptide nature of EGF should allow easy manipulation for coupling.

However, the direct attachment of EGF to the PEI:DNA delivery composition demonstrated no increase in specific nucleic acid delivery. It is possible that the close proximity of EGF to the delivery composition may cause steric hindrance and inefficient interactions between EGF and EGFr. It could also be that the high, general gene delivery efficiency of the generic delivery composition formulations may be too difficult to overcome.

To address these factors, a biotinylated form of PEI that has one biotin per PEI molecule was used. This allowed the attachment of an anti-biotin antibody to the delivery composition that would serve several purposes: a FITC labeled version of the antibody would allow attachment of a FITC label to the delivery composition and thus delivery composition visualization in delivery studies to determine the nature of nucleic acid delivery associated with this delivery composition; the antibody could serve as a simple point of attachment for the ligand by chemically attaching EGF to the antibody and thus reducing steric hindrance in relation to the delivery composition; and the antibody could be used to not only stabilize the delivery composition but also decrease the non-specific interaction of the delivery composition with the cells, resulting in increased, targeted nucleic acid delivery by the delivery composition.

Figure 19:
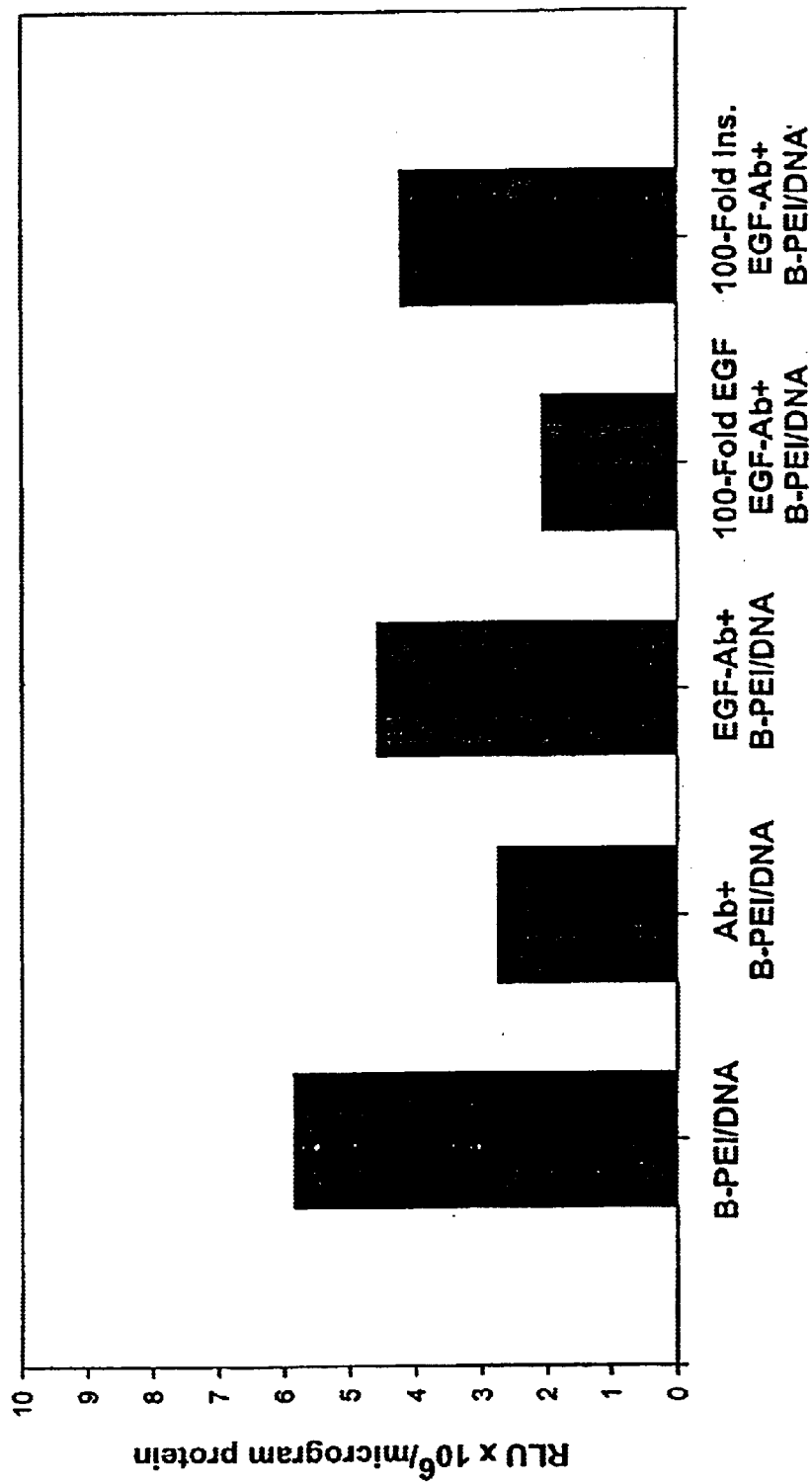
FIG. 19. The effect of adding EGF to PEI:DNA delivery composition formulation II. Delivery composition (2.5 µg DNA) was added to BV cells and incubated as in FIG. 1. Twenty-four hrs. after the initial incubation, the cells were lysed and β-gal expression quantitated by the Galactolite assay.

This delivery composition was made and incubated with the non-modified anti-biotin antibody. However, nucleic acid delivery, as assessed by β-gal quantitation, was decreased as much as 50% on the cell line BV, a bladder cancer cell line that over-expresses the EGFr (FIG. 19). When EGF was coupled to the anti-biotin antibody and then attached to the PEI:DNA delivery composition, nucleic acid delivery increased back to levels similar to those obtained with the original PEI:DNA delivery composition (FIG. 19).

To determine if delivery mediated by the EGF targeted delivery composition was occurring specifically through the EGFr and not through non-specific uptake pathways, the same nucleic acid delivery study with the EGF targeted delivery composition, but additionally included a 100-fold molar excess of either free EGF or insulin. Interestingly, there was only a sharp decrease in nucleic acid expression when EGF was used as a competitor and not when insulin was used as a non-specific competitor (FIG. 19). These studies demonstrate that these delivery composition formulations can be comprised as targeted delivery compositions.

Example 13

PEI/DNA Vector Formulation Use

Further investigation of the use of PEI/DNA vector formulations was carried out in several different areas, including: 1) New Applications of the Vector Formulation, 2) Further Identification of Vector Formation Parameters, and 3) Identification of Gene Delivery Mechanism In Vivo.

1) New Applications of the Vector Formulations:

In an attempt to demonstrate vector formulation use in delivery of nucleic acids containing other therapeutic genes, studies were initiated using a plasmid that expresses the Herpes Simplex Thymidine Kinase (HSV-TK) gene in developing a prodrug approach to killing tumor cells. An initial study was designed to determine if the novel PEI/DNA vector formulation could obtain sufficient gene delivery and tumor cell kill when cells were treated with gancyclovir (GCV) following gene delivery. The breast cancer cell line, MCF-7 was incubated with vector (2.5 $\mu$g DNA) for 3 hrs. after which vector containing media was replaced with fresh media. Following a 24 hrs. incubation, the media was then replaced with media containing GCV ([ ]=15 $\mu$M) for 24 hrs. The GCV containing media was then removed and cell counts were performed every 24 hr following GCV removal. Treatment of the cells with the PEI/DNA vector containing the HSV-TK gene (TK) in combination with GCV (PEI/DNA-TK+GCV) resulted in a greater than 50% reduction in tumor cell number as compared to control cells (no treatment), cells treated with GCV only, or PEI/DNA vector carrying the HSV-TK gene (TK) (FIG. 26).

Based on this analysis, optimization of both vector and GCV dose is being optimized to obtain an improved affect as well as pursuing this observation further in breast, prostate, bladder, and lung cancer orthotopic animal models.

2) Further Identification of Vector Formation Parameters:

To continue the analysis of the parameters for vector formation, the affect of overall reaction volume was further explored as it related to vector formation. This was based on the hypothesis that since vector formation in the formulations described herein is truly self-assembling, in that vector components can be combined without mixing; e.g., the addition of one volume (PEI) into another (DNA) results in diffusion of components. Thus, PEI passing into solution containing DNA results in mixing and resultss in vector formation. As a result, if the overall vector formation volume is increased as well as the volume of the components, then the rate of vector formation or self-assembly will be significantly slowed to cause a decrease in vector formation. To test this, a vector formed by using PEI, DNA, and overall vector volume in several different volumes was incubated. When PEI (10 $\mu$l) was added directly into DNA (60 $\mu$l), transduction efficiencies as high as 36% were achieved (FIG. 27, column 1). This formulation corresponds to formulation III. When this same reaction was formed and then brought up to a volume of 560 $\mu$l, with 280 $\mu$l/well, transduction was reduced in half, which was probably due to the volume of vector added to cells (FIG. 27, column 2). However, when PEI in 10 μl was added to DNA in 270 μl and then 280 μl/well was added to cells, the transduction decreased even further (FIG. 27, column 3) and was reduced even more when the volume of DNA was increase to 550 μl (FIG. 27, column 4). This indicated that even while PEI is added to DNA in a small volume, the volume in which the DNA is in or the local concentration of DNA can affect vector formation. It is possible that incubating these components together under these conditions for a longer period of time would result in more efficient vector formation. To further test this affect, PEI was combined in 40 μl with DNA in 240 μl using formulation III conditions and then increased the reaction volume to 560 μl and 280 μl/well was added (FIG. 27, column 5). Transduction increased back up to levels similar to sample 2. However, when PEI in 80 μl was added to DNA in 480 μl, the transduction decreased again (FIG. 27, column 6). This was further checked by adding PEI to DNA in equal volumes of 140 μl and then adding in 280 μl of buffer, using 280 μl/well. Transduction increased slightly (FIG. 27, column 7). However, when the volume of PEI and DNA was raised to 280 μl each, transduction decreased again (FIG. 27, column 8). The reuslts indicated that the volumes of DNA and PEI can be changed but that relative concentration of the DNA was important. Further, vector formation is not limited to the addition of PEI to DNA, as the reverse approach can be used. The most important aspect is that interaction of the components is allowed. This could be done by vortexing, such as in formulation II described above for exemplary purposes, it was noticed that the vector had a tendency to adhere to objects, resulting in variability. This lead to further studies of formulation III, where components are combined and allowed to mix by diffusion. The reuslts indicated that anything that may affect that rate at which mixing occurs, such as overall reaction volume or the concentration of the components, will affect vector formation.

3) Identification of Gene Delivery Mechanism in vivo:

Studies were also pursued regarding the novel observation that the PEI/DNA vector formulation were capable of mediating efficient gene delivery in vivo by an intravenous route. As addition of polyethylene glycol (PEG) to the vector formulation was found to be beneficial, ity was hypothesized that PEG enhances the half-life of the vector in the circulation and may contribute to increased vector deposition in the tumor with time. To test this, nude mice bearing subcutaneous tumors were injected by an intravenous route with various vector components followed by measuring of βgal expression (βgal expressing plasmid) in tumor homogenates 24 and 72 hrs after vector administration. Twenty-four hours after vector administration (total of 6 μg DNA), animals injected with the PEI/DNA vector+PEG demonstrated the highest amount of expression as compared to animals injected with DNA only, DNA+PEG, or the PEI+DNA vector (FIG. 28). Seventy-two hours after sample administration, the overall level of gene expression dropped, however; the highest amount of expression was still in the animals injected with the PEI/DNA vector+PEG. This provided further evidence that PEG enhances the half-life and/or deposition of PEI/DNA vector in tumor following an intravenous administration.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766
U.S. Pat. No. 4,661,913
U.S. Pat. No. 4,680,338
U.S. Pat. No. 4,714,682
U.S. Pat. No. 4,767,206
U.S. Pat. No. 4,774,189
U.S. Pat. No. 4,857,451
U.S. Pat. No. 4,989,977
U.S. Pat. No. 5,141,648
U.S. Pat. No. 5,160,974
U.S. Pat. No. 5,362,831
U.S. Pat. No. 5,478,722
U.S. Pat. No. 5,563,250
U.S. Pat. No. 5,856,456
U.S. Pat. No. 5,880,270
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251

Almendro et al., "Cloning of the human platelet endothelial cell adhesion molecule-1 promoter and its tissue-specific expression. Structural and functional characterization," *J Immunol.* 157(12):5411–5421, 1996.

Bendas et al., "Targetability of novel immunoliposomes prepared by a new antibody conjugation technique," *Int. J Pharm.*, 181:79–93, 1999.

Bernard et al, "HIV-specific cytotoxic T-lymphocyte activity in immunologically normal HIV-infected persons," *AIDS*, 12(16):2125–2139, 1998.

Blomer et al., "Highly efficient and sustained gene transfer in adult neurons with a lentivirus vector," *J. Virol.*, 71(9):6641–6649, 1997.

Boletta et al., "Nonviral gene delivery to the rat kidney with polyethylenimine," *Human Gene Therapy*, 8:1243–1251, 1997.

Bousiffet al., "Polyethylenimine: A versatile vector for gene and oligonucleotide transfer into cells in culture and in vivo," *Proc. Natl. Acad. Sci. USA*, 92:7297–7301, 1995.

Boussif et al., "Optimized galenics improve in vitro gene transfer with cationic molecules up to 1000-fold," *Gene Therapy*, 3:1074–1080, 1996.

Chen et al., "Enhancement of DNA vaccine potency by linkage of antigen gene to an HSP70 gene," *Cancer Research*, 60(4):1035–1042, 2000.

Cleary et al., "Cloning and structural analysis of cDNAs for bcl-2 and a hybrid bcl-2/immunoglobulin transcript resulting from the t(14;18) translocation," *Cell*, 47(1):19–28, 1986.

Coll et al., "In vivo delivery to tumors of DNA complexed with linear polyethylenimine," *Human Gene Therapy*, 10(10):1659–66, 1999.

Couffinhal et al., "Histochemical staining following LacZ gene transfer underestimates transfection efficiency," *Human Gene Therapy*, 8(8):929–34, 1997.

Cristiano and Roth, "Epidermal growth factor mediated DNA delivery into lung cancer cells via the epidermal growth factor receptor," *Cancer Gene Therapy*, 3:4–10, 1996.

Cristiano and Roth, "Molecular conjugates: a targeted gene delivery vector for molecular medicine," *J. Mol. Med.*, 73:479–486, 1995.

Densmore et al., "Aerosol delivery of robust polyethylenimine-DNA complexes for gene therapy and genetic immunization," *Molecular Therapy*, 1:180–188, 2000.

Fronsdal et al., "Efficient DNA-mediated gene transfer into prostate cancer cell line LNCaP," *Prostate*, 43(2): 111–117, 2000.

Gao et al., "Direct in vivo gene transfer to airway epithelium employing adenovirus-polylysine-DNA complexes," *Human Gene Therapy*, 4: 17–23, 1993.

Goula et al., "Polyethylenimine-based intravenous delivery of transgenes to mouse lung," *Gene Therapy*, 5(9):1291–5, 1998.

Greenwald, et al., "Drug delivery systems: Water soluble taxol 2'-poly(ethylene glycol) ester prodrugs-design and in vivo effectiveness," *J. Med Chem.*, 39:424–431, 1996.

Haensler and Szoka, Bioconj. Chem. 4: 372–79 (1993).

Hart, "Synthetic vectors for gene therapy," *Expert Opin. Therapeutic Patents*, 10(2):199–208, 2000.

Hirano et al., "Polymeric derivatives of activated cyclophosphamide as drug delivery systems in antitumor therapy", *Macromol. Chem.*, 180:1125–1130, 1979.

Hoes et al., "Optimization of macromolecular prodrugs of the antitumor antibiotic adriamycin", *J. Controlled Release*, 2:205–213, 1985.

Kafri et al., "Cellular immune response to adenoviral vector infected cells does not require de novo viral gene expression: implications for gene therapy," *Proc. Natl. Acad. Sci. USA*, 95(19):11377–82, 1998.

Kato, et al., "Antitumor activity of 1-barabinofuranosylcytosine conjugated with polyglutamic acid and its derivative," *Cancer Res.*, 44:25–30, 1984.

Kerr et al., "Apoptosis: a basic biological phenomenon with wide-ranging implications in tissue kinetics," *Br J Cancer.*, 26(4):239–257, 1972.

Kircheis et al., "Coupling of cell binding ligands to polyethylenimine for targeted gene delivery," *Gene Therapy*, 4:409–418, 1997.

Kraus et al., "Alternative promoter usage and tissue specific expression of the mouse somatostatin receptor 2 gene," *FEBS Lett.*, 428(3):165–170, 1998.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol Chem.*, 274(12):8282–8290, 1999.

Lee et al., "Activation of beta3-adrenoceptors by exogenous dopamine to lower glucose uptake into rat adipocytes," *J Auton Nerv Syst*. 74(2–3):86–90, 1997.????

Lemaitre et al., 1987, Proc. Natl. Acad. Sci. USA, 84:648–652.

Li et al., "Assesment of recombinant adenoviral vectors for hepatic gene therapy," *Hum Gene Ther.*, 4:403–409, 1993.

Li, et al., "Synthesis and evaluation of water-soluble polyethylene glycol paclitaxel conjugate as a paclitaxel prodrug," *Anti-Cancer Drugs*, 7:642–648, 1996.

Marshall, "Clinical trials—Gene therapy death prompts review of adenovirus vector," *Science*, 286(5448):2244–2245, 1999.

Mitchell et al, "Active-specific immunotherapy for melanoma," *J Clin Oncol.* 8(5):856-869, 1990.

Morimoto "Antitumor agent poly (amino acid) conjugates as a drug carrier in cancer chemotherapy," *J Pharmacobiodyn.* 7(9):688–698, 1984.

Naldini et al, "In vivo gene delivery and stable transduction of nondividing cells by a lentiviral vector," Science, 272(5259):263–267, 1996.

Nguyen et al., "Delivery of the p53 tumor suppressor gene into lung cancer cells by an adenovirus/DNA complex," *Cancer Gene Therapy,* 4:191–198, 1997.

Nguyen et al., "Gene therapy for lung cancer: enhancement of tumor suppression by a combination of sequential systemic cisplatin and adenovirus-mediated p53 gene transfer," *J. Thoracic Cardiovas. Surg.*, 112(5):1372–1377, 1996.

Nomoto et al, "Cloning and characterization of the alternative promoter regions of the human LIMK2 gene responsible for alternative transcripts with tissue-specific expression," *Gene*, 236(2):259–271, 1999.

Plum et al., Biopolymers 30: 631–643 (1990)).

Ravindranath et al., "Quantitation of the density of cell surface carbohydrate antigens on cancer cells with a sensitive cell-suspension ELISA," *J Immunol Methods.* 16;197(1–2):51–67, 1996.

Remington's Pharmaceutical Sciences, 18th Ed. Mack Printing Company, 1990.

Roelvink et al., "Identification of a conserved receptor-binding site on the fiber proteins of CAR-recognizing adenoviridae," *Science,* 286(5444):1568–1571, 1999.

Rosenberg et al., "Human gene marker/therapy clinical protocols," *Human Gene Therapy,* 11(6):919–79, 2000.

Roth and Cristiano, "Gene therapy for cancer: What have the inventors done and where are the inventors going?" *J Natl. Can. Inst.*, 89(1):21–39, 1997.

Rudolph et al., "In vivo gene delivery to the lung using polyethylenimine and fractured polyamidoamine dendrimers," *J. Gene Med.*, 2(4):269–278, 2000.

Spitz et al., "Adenoviral-mediated wild-type p53 gene expression sensitizes colorectal cancer cells to ionizing radiation," *Clin. Cancer Res.*, 2:1665–1671, 1996.

Spitz et al., "In vivo adenovirus mediated p53 tumor suppressor gene therapy in colorectal cancer," *Anticancer Res.*, 16:3415–3422, 1996.

Stevenson et al., 1989, J. Gen. Virol., 70:2673–2682.

Templeton et al., "Improved DNA: liposome complexes for increased systemic delivery and gene expression," *Nature Biotech.*, 15(7):647–52, 1997.

Tomalia et al., *Angew. Chem. Int. Ed. Engl.* 29:138–175, 1990.

Tsumaki et al., "Modular arrangement of cartilage- and neural tissue-specific cis-elements in the mouse alpha2 (XI) collagen promoter," *J Biol Chem.* 273(36):22861–22864, 1998.

van Heeswijk et al., "The synthesis and characterization of polypeptide-adriamycin conjugate and its complexes with adriamycin. Part 1", *J. Controlled Release*, 1:301–315, 1985.

Wawrzynczak & Thorpe, 1987

Wu et al., "Promoter-dependent tissue-specific expressive nature of imprinting gene, insulin-like growth factor II, in human tissues," *Biochem Biophys Res Commun.* 233(1):221–226, 1997.

Wu et al., "Promoter-dependent tissue-specific expressive nature of imprinting gene, insulin-like growth factor II, in human tissues," *Biochem Biophys Res Commun.* 233(1):221–226, 1997.

Xu et al., "The contribution of poly-L-lysine, streptavidin, and epidermal growth factor to EGF/PLL/DNA polyplex formation," *Gene Therapy*, 5:1235–1243, 1998.

Yang et al., "Cellular immunity to viral antigens limits E1-deleted adenoviruses for gene therapy," *Proc. Natl. Acad. Sci., USA*, 91(10):4407–11, 1994.

Zhao-Emonet et al., "The equine herpes virus 4 thymidine kinase is a better suicide gene than the human herpes virus 1 thymidine kinase," *Gene Ther.* 6(9):1638–1642, 1999.

Zhao-Emonet et al., "The equine herpes virus 4 thymidine kinase is a better suicide gene than the human herpes virus 1 thymidine kinase," *Gene Ther.* 6(9):1638–1642, 1999.

What is claimed is:

1. A method of preparing a liquid transfection composition, comprising
   (a) providing a liquid medium comprising a polycation, wherein the polycation is PEI;
   (b) providing a solution comprising a purified nucleic acid, wherein said purified nucleic acid was purified by a method comprising alkaline lysis and RNA removal, protein removal or a combination thereof; and
   (c) combining said liquid medium and said solution to produce a liquid transfection composition comprising said polycation and said nucleic acid, wherein said solution comprises a larger volume than said liquid medium and wherein the liquid transfection composition comprises a molar ratio of polycation moieties to anionic moieties of from about 1:1 to 1,000,000:1.

2. The method of claim 1, wherein said larger volume comprises a ratio greater than 1:1.2 of said liquid medium to said solution.

3. The method of claim 2, wherein said ratio is from about 1:1.2 to about 1:1,000,000.

4. The method of claim 2, wherein said ratio is about 1:3.

5. The method of claim 4, wherein said ratio is about 1:5.

6. The method of claim 5, wherein said ratio is about 1:6.

7. The method of claim 6, wherein said ratio is about 1:7.

8. The method of claim 7, wherein said ratio is about 1:9.

9. The method of claim 8, wherein said ratio is about 1:10.

10. The method of claim 1, wherein said ratio is from about 1:1 to about 6:1.

11. The method of claim 1, wherein said ratio is from about 2.4:1 to 2.7:1.

12. The method of claim 1, wherein said ratio is from about 1.5:1 to 6:1.

13. The method of claim 1, wherein said ratio is about 2.7:1.

14. The method of claim 1, wherein said polycation moieties are amines.

15. The method of claim 1, wherein said anionic moieties are phosphates.

16. The method of claim 1, wherein the liquid transfection composition comprises PEG.

17. The method of claim 1, wherein the liquid transfection composition comprises from about 1% to about 10% PEG.

18. The method of claim 1, wherein the liquid transfection composition comprises from about 5% to about 9% PEG.

19. The method of claim 1, wherein the liquid transfection composition comprises about 8% PEG.

20. The method of claim 16, wherein the PEG is added to the liquid transfection composition following said combining.

21. The method of claim 1, wherein said combining comprises a drop-wise addition of said liquid medium to said solution.

22. The method of claim 1, wherein said combining comprises substantially simultaneous addition of said liquid medium to said solution.

23. The method of claim 1, wherein said RNA removal comprises lithium chloride purification, RNAse digestion or a combination thereof.

24. The method of claim 1, wherein said protein removal comprises protease digestion, organic solvent extraction or a combination thereof.

25. The method of claim 24, wherein said proteinase digestion comprises digestion with proteinase K.

26. The method of claim 1, wherein said polycation is branched.

27. The method of claim 1, wherein said polycation is linear.

28. The method of claim 1, wherein said polycation binds DNA.

29. The method of claim 1, wherein said polycation is attached to a ligand.

30. The method of claim 29, wherein said ligand is a targeting agent.

31. The method of claim 1, wherein the purified nucleic acid is attached to a ligand.

32. The method of claim 1, wherein said polycation is an endosome lysis agent.

33. The method of claim 1, wherein the polycation binds hydrogen ions.

34. The method of claim 1, wherein said polycation comprises a plurality of amine groups.

35. The method of claim 34, wherein said amine groups comprise primary amines, secondary amines, tertiary amines or a combination thereof.

36. The method of claim 35, wherein the amine groups comprise a combination of primary amines, secondary amines and tertiary amines.

37. The method of claim 36, wherein said combination comprises a 1:2:1 ratio of primary: secondary:tertiary amines.

38. The method of claim 1, further comprising the step of admixing said liquid transfection composition.

39. The method of claim 38, wherein said admixing comprises vortexing, tapping or a combination thereof.

40. The method of claim 38, wherein said admixing is carried out for about 0.5 second to about 10 minutes.

41. The method of claim 40, wherein said admixing is for about 30 seconds.

42. The method of claim 38, wherein admixing comprises incubating the composition.

43. The method of claim 42, wherein said incubating is at room temperature for about 2 to about 5 minutes.

44. The method of claim 42, wherein said incubating is up to about 30 minutes.

45. The method of claim 1, wherein the liquid transfection composition further comprises glucose, a buffer, a lipid, an additional nucleic acid, an additional polycation, a proteinaceous composition, a linker/coupling agent, a nucleic acid binding agent, a nucleic acid compacting agent, an endosome lysis agent, a targeting agent, an anti-cancer agent, a vaccine component, a pharmaceutical carrier or a combination thereof.

46. A method of preparing a liquid transfection composition, comprising
   (a) providing a liquid medium comprising a polycation, wherein the polycation is PEI;

(b) providing a solution comprising a purified nucleic acid, wherein the nucleic acid is isolated by a method comprising lithium chloride purification; and (c) combining said liquid medium and said solution comprising a purified nucleic acid to produce a liquid transfection composition comprising said polycation and a nucleic acid, wherein the molar ratio of polycation moieties to anionic moieties is from about 1:1 to 1,000,000:1, wherein said solution comprises a larger volume than said liquid medium.

47. The method of claim 46, wherein the nucleic acid is isolated by a method comprising RNAse digestion.

48. The method of claim 46, wherein the nucleic acid is isolated by a method comprising RNA removal, protein removal or a combination thereof.

49. The method of claim 48, wherein said protein removal comprises protease digestion, organic solvent extraction or a combination thereof.

50. The method of claim 49, wherein said proteinase digestion comprises digestion with proteinase K.

51. The method of claim 46, wherein said larger volume comprises a ratio greater than 1:1.2 of said liquid medium to said solution.

52. The method of claim 51, wherein said ratio is from about 1:1.2 to about 1:1,000,000.

53. The method of claim 51, wherein said ratio is about 1:3.

54. The method of claim 51, wherein said ratio is about 1:5.

55. The method of claim 51, wherein said ratio is about 1:6.

56. The method of claim 51, wherein said ratio is about1:7.

57. The method of claim 51, wherein said ratio is about 1:9.

58. The method of claim 51, wherein said ratio is about 1:10.

59. The method of claim 46, wherein said ratio is from about 1:1 to about 6:1.

60. The method of claim 46, wherein said ratio is from about 2.4:1 to 2.7:1.

61. The method of claim 46, wherein said ratio is from about 1.5:1 to 6:1.

62. The method of claim 46, wherein said ratio is about 2.7:1.

63. The method of claim 46, wherein said polycation moieties are amines.

64. The method of claim 46, wherein said anionic moieties are phosphates.

65. The method of claim 46, wherein the liquid transfection composition comprises PEG.

66. The method of claim 46, wherein said polycation binds DNA.

67. The method of claim 46, further comprising the step of admixing said liquid transfection composition.

68. A method of transfecting a cell, comprising the steps of:

(a) providing a liquid medium comprising a polycation, wherein the polycation is PEI;

(b) providing a solution comprising a purified nucleic acid, wherein said purified nucleic acid was purified by a method comprising alkaline lysis and RNA removal, protein removal or a combination thereof;

(c) combining said liquid medium and said solution comprising a nucleic acid, wherein said solution comprises a larger volume than said liquid medium and wherein the liquid transfection composition comprises a molar ratio of polycation moieties to anionic moieties of from about 1:1 to 1,000,000:1, to produce a liquid transfection composition comprising said polycation and said nucleic acid; and (d) contacting a cell with said liquid transfection composition.

69. The method of claim 68, wherein the transduction efficiency is greater than 30%.

70. The method of claim 68, wherein the transduction efficiency is greater than 50%.

71. The method of claim 68, wherein the transduction efficiency is greater than 70%.

72. The method of claim 68, wherein the transduction efficiency is greater than 80%.

73. The method of claim 68, wherein the transduction efficiency is greater than 90%.

74. The method of claim 68, wherein the transduction efficiency is about 99%.

75. The method of claim 68, wherein the transfection composition further comprises PEG, glucose, a buffer, a lipid, an additional nucleic acid, an additional polycation, a proteinaceous composition, a linker/coupling agent, a nucleic acid binding agent, a nucleic acid compacting agent, an endosome lysis agent, a targeting agent, an anti-cancer agent, a vaccine component, a pharmaceutical carrier or a combination thereof.

76. The method of claim 75, wherein the transfection composition comprises PEG.

77. The method of claim 75, wherein the transfection composition comprises from about 1% to about 10% PEG.

78. The method of claim 75, wherein the transfection composition comprises from about 5% to about 9% PEG.

79. The method of claim 75, wherein the transfection composition comprises about 8% PEG.

80. The method of claim 68, wherein said contacting produces expression of a RNA encoded by said nucleic acid.

81. The method of claim 75, wherein the targeting agent is EGF.

82. The method of claim 80, wherein a proteinaceous sequence is translated from said RNA.

83. The method of claim 82, wherein said proteinaceous sequence comprises a sequence of a reporter gene.

84. The method of claim 68, wherein the transfection composition kills less than about 20% of contacted cells or does not reduce cell number beyond 24 hrs after administration of the transfection composition.

85. A method of reducing the growth of cancer cells, comprising the steps of:

(a) providing a liquid medium comprising a polycation, wherein the polycation is PEI;

(b) providing a solution comprising a purified nucleic acid, wherein said purified nucleic acid was purified by lithium chloride purification and wherein said nucleic acid encodes an anti-cancer nucleic acid or proteinaceous sequence;

(c) combining said liquid medium and said solution, wherein said solution comprises a larger volume than said liquid medium and wherein the liquid transfection composition comprises a molar ratio of polycation moieties to anionic moieties of from about 1:1 to 1,000,000:1, to produce a liquid transfection composition comprising said polycation and said nucleic acid; and (d) directly contacting tissue comprising cancer cells with said liquid transfection composition to transfect the cells with the nucleic acid.

86. The method of claim 85, wherein said nucleic acid sequence comprises a sequence of a tumor suppressor gene.

87. The method of claim 85, said cancer cells are rapidly dividing.

88. The method of claim 85, wherein said cells are contained in an organism.

89. The method of claim 88, wherein said organism is a human.

90. A transfection composition, comprising a polycation and a nucleic acid, prepared by the steps of:
   (a) providing a liquid medium comprising a polycation, wherein the polycation is PEI;
   (b) providing a solution comprising a purified nucleic acid, wherein said purified nucleic acid was purified by a method comprising alkaline lysis and RNA removal, protein removal or a combination thereof; and
   (c) adding said liquid medium to said solution comprising a nucleic acid, wherein said solution comprises a larger volume than said liquid medium, to produce a liquid transfection composition, wherein the liquid transfection composition comprises a molar ratio of polycation moieties to anionic moieties of from about 1:1 to 1,000,000:1.

91. The method of claim 68, wherein said RNA removal comprises lithium chloride purification, RNAse digestion or a combination thereof.

92. The method of claim 91, wherein said protein removal comprises protease digestion, organic solvent extraction or a combination thereof.

93. The method of claim 92, wherein the purified nucleic acid was purified by lithium chloride purification.

94. The method of claim 68, wherein the ratio of polycation moieties to anionic moieties is from about 1:1 to about 6:1.

95. The method of claim 85, wherein the ratio of polycation moieties to anionic moieties is from about 1:1 to about 6:1.

96. The transfection composition of claim 90, wherein said RNA removal comprises lithium chloride purification, RNAse digestion or a combination thereof.

97. The transfection composition of claim 90, wherein said protein removal comprises protease digestion, organic solvent extraction or a combination thereof.

98. The transfection composition of claim 90, wherein the purified nucleic acid was purified by alkaline lysis.

99. The transfection composition of claim 90, wherein the ratio of polycation moeities to anionic moeities is from about 1:1 to about 6:1.

100. A method of reducing the growth of cancer cells, comprising the steps of:
   (a) providing a liquid medium comprising a polycation, wherein the polycation is PEI;
   (b) providing a solution comprising a purified nucleic acid, wherein said purified nucleic acid was purified by lithium chloride purification and wherein said nucleic acid encodes an anti-cancer nucleic acid or proteinaceous sequence;
   (c) combining said liquid medium and said solution, wherein said solution comprises a larger volume than said liquid medium and wherein the liquid transfection composition comprises a molar ratio of polycation moieties to anionic moieties of from about 9:1 to 2.4:1, to produce a liquid transfection composition comprising said polycation and said nucleic acid; and
   (d) contacting cancer cells with said liquid transfection composition to transfect the cells with the nucleic acid.

101. The method of claim 100, wherein said nucleic acid sequence comprises a sequence of a tumor suppressor gene.

102. The method of claim 100, wherein said cells are contained in an organism.

103. The method of claim 102, wherein said organism is a human.

* * * * *